(12) United States Patent
Wands et al.

(10) Patent No.: US 9,308,198 B2
(45) Date of Patent: Apr. 12, 2016

(54) TREATMENT, PREVENTION, AND REVERSAL OF ALCOHOL-INDUCED BRAIN DISEASE

(75) Inventors: Jack R. Wands, East Greenwich, RI (US); Suzanne Marie de la Monte, East Greenwich, RI (US)

(73) Assignee: RHODE ISLAND HOSPITAL, Providence, RI (US)

(*) Notice: Subject to any disclaimer, the term of this patent is extended or adjusted under 35 U.S.C. 154(b) by 791 days.

(21) Appl. No.: 12/310,831

(22) PCT Filed: Sep. 10, 2007

(86) PCT No.: PCT/US2007/019626
§ 371 (c)(1),
(2), (4) Date: Nov. 9, 2009

(87) PCT Pub. No.: WO2008/030604
PCT Pub. Date: Mar. 13, 2008

(65) Prior Publication Data
US 2010/0055037 A1    Mar. 4, 2010

Related U.S. Application Data

(60) Provisional application No. 60/842,988, filed on Sep. 8, 2006.

(51) Int. Cl.
C07C 15/12    (2006.01)
A61K 31/425    (2006.01)
A61K 31/47    (2006.01)

(52) U.S. Cl.
CPC .............. A61K 31/425 (2013.01); A61K 31/47 (2013.01)

(58) Field of Classification Search
CPC ....................................................... C07C 15/12
See application file for complete search history.

(56) References Cited

U.S. PATENT DOCUMENTS

| | | |
|---|---|---|
| 4,902,505 A | 2/1990 | Pardridge et al. |
| 5,166,320 A | 11/1992 | Wu et al. |
| 5,223,242 A | 6/1993 | Khaw et al. |
| 5,260,308 A | 11/1993 | Poduslo et al. |
| 5,326,770 A | 7/1994 | Wilkerson |
| 5,482,698 A | 1/1996 | Griffiths |
| 5,525,338 A | 6/1996 | Goldenberg |
| 5,547,932 A | 8/1996 | Curiel et al. |
| 5,620,675 A | 4/1997 | McBride et al. |
| 5,690,907 A | 11/1997 | Lanza et al. |
| 5,693,509 A | 12/1997 | Cotten et al. |
| 5,780,010 A | 7/1998 | Lanza et al. |
| 5,902,726 A | 5/1999 | Kliewer et al. |
| 5,925,657 A | 7/1999 | Seed et al. |
| 5,939,442 A | 8/1999 | Evans et al. |
| 5,958,371 A | 9/1999 | Lanza et al. |
| 5,965,404 A | 10/1999 | Buschle et al. |
| 5,989,520 A | 11/1999 | Lanza et al. |
| 5,994,554 A | 11/1999 | Kliewer et al. |
| 6,022,897 A | 2/2000 | Evans et al. |
| 6,028,109 A | 2/2000 | Willson |
| 6,060,515 A | 5/2000 | Elias et al. |
| 6,083,486 A | 7/2000 | Weissleder et al. |
| 6,200,955 B1 | 3/2001 | Harris et al. |
| 6,207,690 B1 | 3/2001 | Urban et al. |
| 6,214,850 B1 | 4/2001 | Evans et al. |
| 6,242,196 B1 | 6/2001 | Spiegelman et al. |
| 6,294,559 B1 | 9/2001 | Smith |
| 6,294,580 B1 | 9/2001 | Willson et al. |
| 6,306,854 B1 | 10/2001 | Brown et al. |
| 6,372,250 B1 | 4/2002 | Pardridge |
| 6,376,512 B1 | 4/2002 | Jayyosi et al. |
| 6,413,994 B1 | 7/2002 | Evans et al. |
| 6,462,046 B2 | 10/2002 | Lou et al. |
| 6,506,797 B1 | 1/2003 | Nomura et al. |
| 6,525,083 B2 | 2/2003 | Acton, III et al. |
| 6,541,492 B1 | 4/2003 | Collins et al. |
| 6,548,538 B2 | 4/2003 | Urbahns et al. |
| 6,555,536 B2 | 4/2003 | Burris et al. |
| 6,579,893 B1 | 6/2003 | Urban et al. |
| 6,599,899 B2 | 7/2003 | Burris et al. |
| 6,605,627 B2 | 8/2003 | Evans et al. |
| 6,646,008 B1 | 11/2003 | Evans et al. |
| 6,673,823 B2 | 1/2004 | Heaney et al. |
| 6,676,926 B2 | 1/2004 | Hilger et al. |
| 6,677,298 B2 | 1/2004 | Hariharan |
| 6,699,904 B2 | 3/2004 | Hayward et al. |
| 6,710,053 B2 | 3/2004 | Naicker et al. |

(Continued)

FOREIGN PATENT DOCUMENTS

| | | |
|---|---|---|
| EP | 1586573 A1 | 10/2005 |
| KR | 10-1081977 | 11/2011 |
| KR | 10-1174726 | 8/2012 |
| WO | WO-2005049572 A1 | 6/2005 |
| WO | WO 2008/036678 | 3/2008 |
| WO | WO 2008/128126 | 10/2008 |

OTHER PUBLICATIONS

De La Monte et al. In Cellular and Molecular Life Science 59 (2002) 882-893.*
Syapin et al. In Alcoholism: Clinical and Experimental Research 29(6), 2005: pp. 1080-1089.*
Korbo, L. In Alcoholism: Clinical and Experimental Research 25(1) 164-168.*
Rasgon et al. In Journal of Gerontology, 2004, 59A(2), 178-183.*
Harper et al. (Current Opinion in Pharmacology 2005, 5:73-78.*
Definition of Reverse (/www.merriam-webster.com/dictionary/reverse).*
Definition of Prevent (/www.merriam-webster.com/dictionary/prevent).*
Pfefferbaum et al. In American Journal of Psychiatry 2004; 161:1190-1196.*

(Continued)

*Primary Examiner* — Brian McDowell
(74) *Attorney, Agent, or Firm* — Mintz Levin Cohn Ferris Glovsky and Popeo, P.C.; Ingrid A. Beattie; Linyu L. Mitra

(57) ABSTRACT

This invention relates to methods for treating, preventing, or reversing brain disease or damage produced by chronic alcohol intake by administering a peroxisome proliferator activated receptor (PPAR) agonist.

8 Claims, 19 Drawing Sheets

(56) References Cited

U.S. PATENT DOCUMENTS

Figures 3A, 3B, 3C, 3D, 3E, 3F, 3G, 3H, 3I, 3J, 3K, 3L:
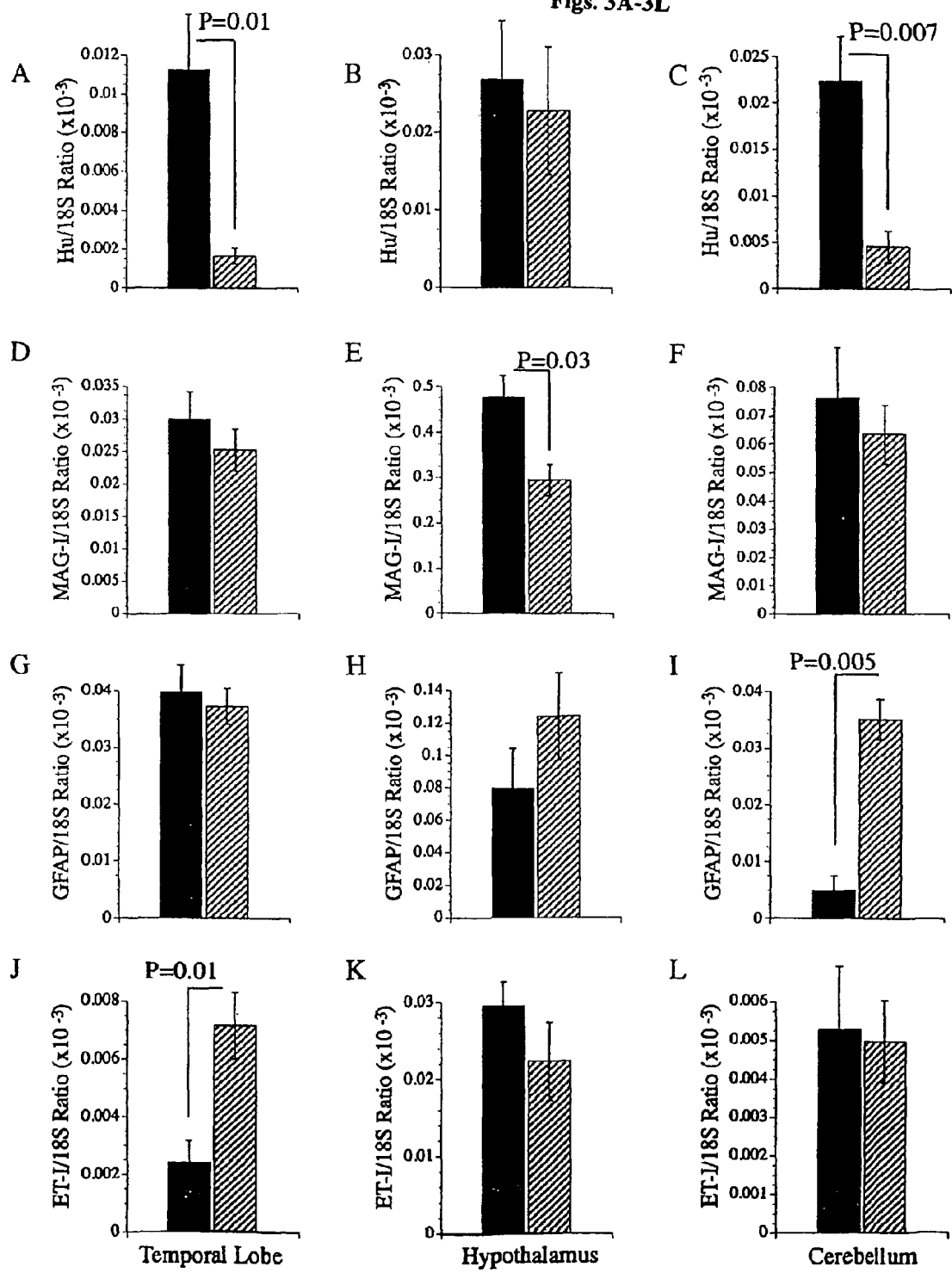

| | | | |
|---|---|---|---|
| 6,713,514 B1 | 3/2004 | Kolb et al. |
| 6,723,740 B2 | 4/2004 | Chao et al. |
| 6,737,247 B2 | 5/2004 | Bogdanov et al. |
| 6,750,236 B2 | 6/2004 | Urbahns et al. |
| 6,787,552 B2 | 9/2004 | Sakuma et al. |
| 6,787,556 B1 | 9/2004 | Hargreaves et al. |
| 6,787,651 B2 | 9/2004 | Stolle et al. |
| 6,852,738 B2 | 2/2005 | Jones et al. |
| 6,869,967 B2 | 3/2005 | Jeppesen et al. |
| 6,897,235 B2 | 5/2005 | Pisano et al. |
| 6,908,908 B2 | 6/2005 | Burris et al. |
| 6,987,118 B2 | 1/2006 | Chang |
| 7,015,329 B2 | 3/2006 | Kuo et al. |
| 7,049,342 B2 | 5/2006 | Miyachi et al. |
| 7,060,530 B2 | 6/2006 | Kanatake |
| 7,090,874 B2 | 8/2006 | Mae et al. |
| 7,091,225 B2 | 8/2006 | Sierra |
| 7,091,230 B2 | 8/2006 | Adams et al. |
| 7,091,245 B2 | 8/2006 | Jeppesen et al. |
| 2004/0115127 A1 | 6/2004 | Wright et al. |
| 2004/0224995 A1 | 11/2004 | Simpkins et al. |
| 2005/0245589 A1 | 11/2005 | Ackermann et al. |

OTHER PUBLICATIONS

Watson et al. In American Journal of Geriatric Psychiatry 13(11), 950-958 (2005).*

Savage et al. "Alcohol-Induced Brain Pathology and Behavioral Dysfunction: Using an Animal Model to Examine Sex Differences." *Alcohol Clin. Exp. Res.* 24.4(2000):465-475.

Burd et al.,. "Fetal alcohol syndrome: neuropsychiatric phenomics", *Neurotoxicol. Teratol.*, 25:697-705 (2003).

Burd et al., "Recognition and management of fetal alcohol syndrome", *Neurotoxicol. Teratol.*, 25:681-688 (2003).

Clarren et al., "Brain malformations related to prenatal exposure to ethanol", *J. Pediatr.*, 92:64-67 (1978).

de la Monte et al., "Partial Rescue of Ethanol-Induced Neuronal Apoptosis by Growth Factor Activation of Phosphoinositol-3-Kinase", *Alcohol Clin. Exp. Res.*, 24(5):716-726 (2000).

de la Monte et al., "Mitochondrial DNA Damage and Impaired Mitochondrial Function Contribute to Apoptosis of Insulin-Stimulated Ethanol-Exposed Neuronal Cells", *Alcohol Clin. Exp. Res.*, 25(6):898-906 (2001).

de la Monte et al., "Ethanol impairs insulin-stimulated mitochondrial function in cerebellar granule neurons", *Cell. Mol. Life Sci.*, 58:1950-1960 (2001).

de la Monte et al., "Chronic gestational exposure to ethanol impairs insulin-stimulated survival and mitochondrial function in cerebellar neurons", *Cell. Mol. Life Sci.*, 59:882-893 (2002).

Gammeltoft et al., "Insulin receptors in the mammalian central nervous system : binding characteristics and subunit structure", *Biochimie*, 67:1147-1153 (1985).

Goodyear et al., "Characterization of Insulin-Like Growth Factor Receptors in Rat Anterior Pituitary, Hypothalamus, and Brain", *Endocrinol.*, 114(4):1187-1195 (1984).

Hallak et al., "Inhibition of Insulin-Like Growth Factor-I Signaling by Ethanol in Neuronal Cells", *Alcohol Clin. Exp. Res.*, 25(7):1058-1064 (2001).

Hill et al., "Autoradiographic Localization of Insulin Receptors in Rat Brain: Prominence in Olfactory and Limbic Areas", *Neuroscience*, 17(4):1127-1138 (1986).

Ikonomidou et al., "Ethanol-Induced Apoptotic Neurodegeneration and Fetal Alcohol Syndrome", *Science*, 287:1056-1060 (2000).

Liesi et al., "Ethanol-Exposed Central Neurons Fail to Migrate and Undergo Apoptosis", *J. Neurosci. Res.*, 48:439-448 (1997).

Maier et al., "Regional differences in cell loss associated with binge-like alcohol exposure during the first two trimesters equivalent in the rat", *Alcohol*, 23:49-57 (2001).

Mattson et al., "Teratogenic Effects of Alcohol on Brain and Behavior", *Alcohol Res. Health*, 25(3):185-191 (2001).

Minana et al., "Alcohol Exposure Alters the Expression Pattern of Neural Cell Adhesion Molecules During Brain Development", *J. Neurochem.*, 75:954-964 (2000).

O'Malley et al., "Clinical Implications of a Link Between Fetal Alcohol Spectrum Disorder and Attention-Deficit Hyperactivity Disorder", *Can. J. Psychiatry*, 47(4):349-354 (2002).

Olney et al., "Ethanol-induced apoptotic neurodegeneration in the developing brain", *Apoptosis*, 5:515-521 (2000).

Ramachandran et al., "In Utero Ethanol Exposure Causes Mitochondrial Dysfunction, Which Can Result in Apoptotic Cell Death in Fetal Brain: A Potential Role for 4-Hydroxynonenal", *Alcohol Clin. Exp. Res.*, 25(6):862-871 (2001).

Soscia et al., "Chronic gestational exposure to ethanol causes insulin and IGF resistance and impairs acetylcholine homeostasis in the brain", *Cell. Mol. Life Sci.*, 63:2039-2056 (2006).

Swanson et al., "Chronic Prenatal Ethanol Exposure Alters the Normal Ontogeny of Choline Acetyltransferase Activity in the Rat Septohippocampal System", *Alcohol Clin. Exp. Res.*, 19:1252 (1995).

Yanni et al., "Ethanol inhibits development of dendrites and synapses in rat hippocampal pyramidal neuron cultures", *Brain Res. Dev. Brain Res.*, 120:233-243 (2000).

Zhang et al., "Ethanol Induces Apoptosis in Cerebellar Granule Neurons by Inhibiting Insulin-Like Growth Factor 1 Signaling", *J Neurochem.*, 71:196-204 (1998).

Besson et al., "Fenofibrate, a peroxisome proliferator-activated receptor alpha agonist, exerts neuroprotective effects in traumatic brain injury", Neuroscience Letters, 388:7-12 (2005).

de la Monte et al., "Ethanol inhibits insulin expression and actions in the developing brain", CMLS, Cell Mol. Life Sci., 62:1131-1145 (2005).

de la Monte et al. "Molecular indices of oxidative stress and mitochondrial dysfunction occur early and often progress with severity of Alzheimer's disease", Journal of Alzheimer's Disease, 9:167-181 (2006).

Dembele et al., "Intrauterine ethanol exposure results in hypothalamic oxidative stress and neuroendocrine alterations in adult rat offspring", Am. J. Physiol. Regul. Integr. Comp. Physiol., 291:R796-R802 (2006).

Etkind et al., "Cocaine and Alcohol Synergism in Taste Aversion Learning", Pharmacology Biochemistry and Behavior, 59:649-655 (1998).

Korbo, Lise, "Glial Cell Loss in the Hippocampus of Alcoholics", Alcohol Clin. Exp. Res., 23:164-168 (1999).

Leisewitz et al., "Ethanol specifically decreases peroxisome proliferator activated receptor beta in B12 oligodendrocyte-like cells", Journal of Neurochemistry, 85:135-141 (2003).

Polak et al., "Protective effects of a peroxisome proliferator-activated receptor-β/δ agonist in experimental autoimmune encephalomyelitis", Journal of Neuroimmunology, 168:65-75 (2005).

Ramachandran et al., "Ethanol-Induced or Oxidative Stress Precedes Mitochondrially Mediated Apoptotic Death of Cultured Fetal Cortical Neurons", Journal of Neuroscience Research, 74:577-588 (2003).

Syapin et al., "Alcohol Brain Damage and Neuroinflammation: Is There a Connection?", Alcohol Clin. Exp. Res., 29:1080-1089 (2005).

Valles et al.; Chronic ethanol treatment enhances inflammatory mediators and cell death in the brain and in astrocytes; Brain Pathol. 14:365-371 (Abstract) (2004).

Soscia et al., "Chronic gestational exposure to ethanol causes insulin and IGF resistance and impairs acetylcholine homeostasis in the brain", Cell. Mol. Life Sci., 1-13 (2006).

Arnt et al. "Synthetic Smac/DIABLO Peptides Enhance the Effects of Chemotherapeutic Agents by Binding XIAP and cIAP1 in Situ." *J. Biol. Chem.* 277.46(2002):44236-44243.

Baltensperger et al. "Binding of the Ras Activator Son of Sevenless to Insulin Receptor Substrate-1 Signaling Complexes." *Science*. 260. 5116(1993):1950-1952.

Barish et al., PPAR delta: a dagger in the heart of the metabolic syndrome. J Clin Invest. Mar. 2006;116(3):590-7.

Berger et al., PPARs: therapeutic targets for metabolic disease. Trends Pharmacol Sci. May 2005;26(5):244-51.

(56) References Cited

OTHER PUBLICATIONS

Blessed et al. "The Association Between Quantitative Measures of Dementia and of Senile Change in the Cerebral Grey Matter of Eldery Subjects." *Br. J. Psychiat.* 114.512(1968):797-811.

Cockrell et al. "Mini-Mental State Examination (MMSE)." *Psychopharmacol. Bull.* 24.4(1988):689-692.

Combs et al. "Inflammatory Mechanisms in Alzheimer's Disease: Inhibition of β-Amyloid-Stimulated Proinflammatory Responses and Neurotoxicity by PPARy Agonists." *J. Neurosci.* 20.2(2000):558-567.

Condorelli et al. "Caspase Cleavage Enhances the Apoptosis-Inducing Effects of BAD." *Mol. Cell. Biol.* 21.9(2001):3025-3036.

Crum et al. "Population-Based Norms for the Mini-Mental State Examination by Age and Educational Level." *JAMA.* 269.18(1993):2386-2391.

Dahia et al. "*PTEN* is Inversely Correlated with the Cell Survival Factor Akt/PKB and is Inactivated via Multiple Mechanisms Haematological Malignancies." *Hum. Mol. Genet.* 8.2(1999):185-193.

Datta et al. "Akt Phosphorylation of BAD Couples Survival Signals to the Cell-Intrinsic Death Machinery." *Cell.* 91.2(1997):231-241.

de la Monte et al. "Oxygen Free Radical Injury is Sufficient to Cause Some Alzheimer-Type Molecule Abnormalities in Human CNS Neuronal Cells." *J. Alzheimers Dis.* 2.3-4(2000):261-281.

Dudek et al. "Regulation of Neuronal Survival by the Serine-Threonine Protein Kinase Akt." *Science.* 275.5300(1997):661-665.

Eves et al. "Akt, a Target of Phosphatidylinositol 3-Kinase, Inhibits Apoptosis in a Differentiating Neuronal Cell Line." *Mol. Cell. Biol.* 18.4(1998):2143-2152.

Fulda et al. "Smac Agonists Sensitize for Apo2L/TRAIL- or Anticancer Drug-Induced Apoptosis and Induce Regression of Malignant Glioma in vivo." *Nat. Med.* 8.8(2002):808-815.

Fulop et al., Plasma lactate and 3-hydroxybutyrate levels in patients with acute ethanol intoxication. Am J Med. Feb. 1986;80(2):191-4.

Gershon et al. "Methods for the Evaluation of Pharmacologic Agents in the Treatment of Cognitive and Other Deficits in Dementia." *Clinical Evaluation of Psychotropic Drugs: Principles and Guidelines.* Prien et al., eds. New York: Raven Press, Ltd. (1994):467-499.

Halestrap et al. "Mitochondria and Cell Death." *Biochem. Soc. Trans.* 28.2(2000):170-177.

Hetman et al. "Role of Glycogen Synthase Kinase-3β in Neuronal Apoptosis Induced by Trophic Withdrawal." *J. Neurosci.* 20.7(2000):2567-2574.

Hirsch et al. "Mitochondrial Permeability Transition in Apoptosis and Necrosis." *Cell. Biol. Toxicol.* 14.2(1998):141-145.

Jagger et al., Effect of alcohol intoxication on the diagnosis and apparent severity of brain injury. Neurosurgery. Sep. 1984;15(3):303-6.

Katzman et al. "Validation of a Short Orientation-Memory-Concentration Test of Cognitive Impairment." *Am. J. Psychiatry.* 140.6(1983):734-749.

Kokmen et al. "A Short Test of Mental Status: Description and Preliminary Results." *Mayo Clin. Proc.* 62.4(1987):281-288.

Lam et al. "The Phosphatidylinositol 3-Kinase Serine Kinase Phosphorylates IRS-1: Stimulation by Insulin and Inhibition by Wortmannin." *J. Biol. Chem.* 269.32(1994):20648-20652.

Luquet et al., Roles of PPAR delta in lipid absorption and metabolism: a new target for the treatment of type 2 diabetes. Biochim Biophys Acta. May 30, 2005;1740(2):313-7. Epub Dec. 8, 2004.

Myers et al. "The IRS-1 Signaling System." *Trends Biochem. Sci.* 19.7(1994):289-293.

Nolan et al. "Improvement in Glucose Tolerance and Insulin Resistance in Obese Subjects Treated with Troglitazone." *N. Engl. J. Med.* 331.18(1994):1188-1193.

Pfeffer et al. "Measurement of Functional Activities in Older Adults in the Community." *J. Gerontol.* 37.3(1982):323-329.

Seimandi et al., Differential responses of PPARalpha, PPARdelta, and PPARgamma reporter cell lines to selective PPAR synthetic ligands. Anal Biochem. Sep. 1, 2005;344(1):8-15.

Tanaka T et al., Activation of peroxisome proliferator-activated receptor delta induces fatty acid beta-oxidation in skeletal muscle and attenuates metabolic syndrome. Proc Natl Acad Sci U S A. Dec. 23, 2003;100(26):15924-9. Epub Dec. 15, 2003.

Urso et al. "Blood Ethanol Levels in Sober Alcohol Users Seen in an Emergency Room." *Life Sci.* 28.9(1981):1053-1056.

Wang et al. "Regulation of Muscle Fiber Type and Running Endurance by PPARδ." *PLoS Biol.* 2.10(2004):e294.

Xu et al. "Ethanol Impairs Insulin-Stimulated Neuronal Survival in the Developing Brain: Role of PTEN Phosphatase." *J. Biol. Chem.* 278.29(2003):26929-26937.

Yang et al. "Predominant Suppression of Apoptosome by Inhibitor of Apoptosis Protein in Non-Small Cell Lung Cancer H460 Cells: Therapeutic Effect of a Novel Polyarginine-Conjugated Smac Peptide." *Cancer Res.* 63.4(2003):831-837.

Yeon et al. "Potential Role of PTEN Phosphatase in Ethanol-Impaired Survival Signaling in the Liver." *Hepatol.* 38.3(2003):703-714.

\* cited by examiner

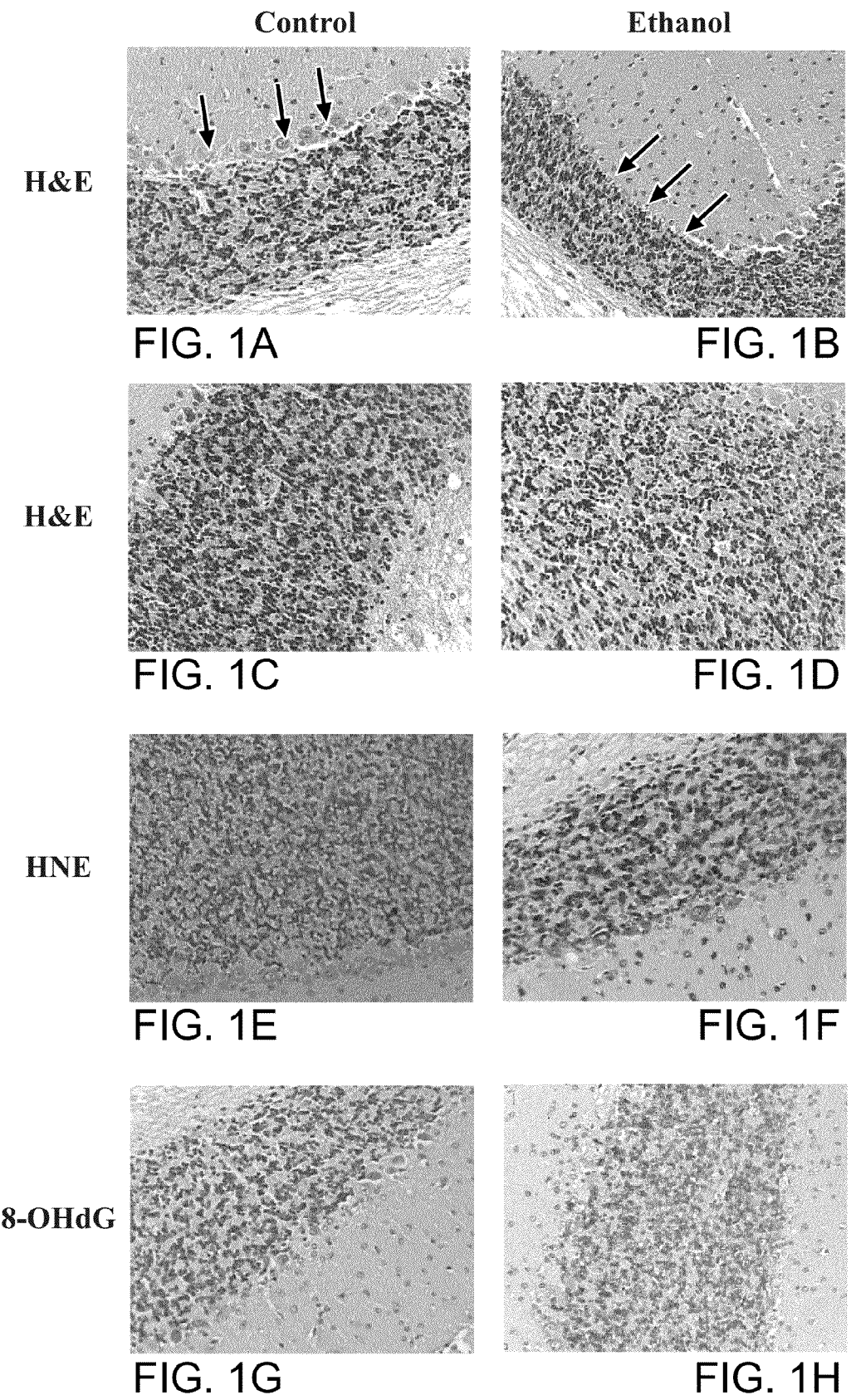

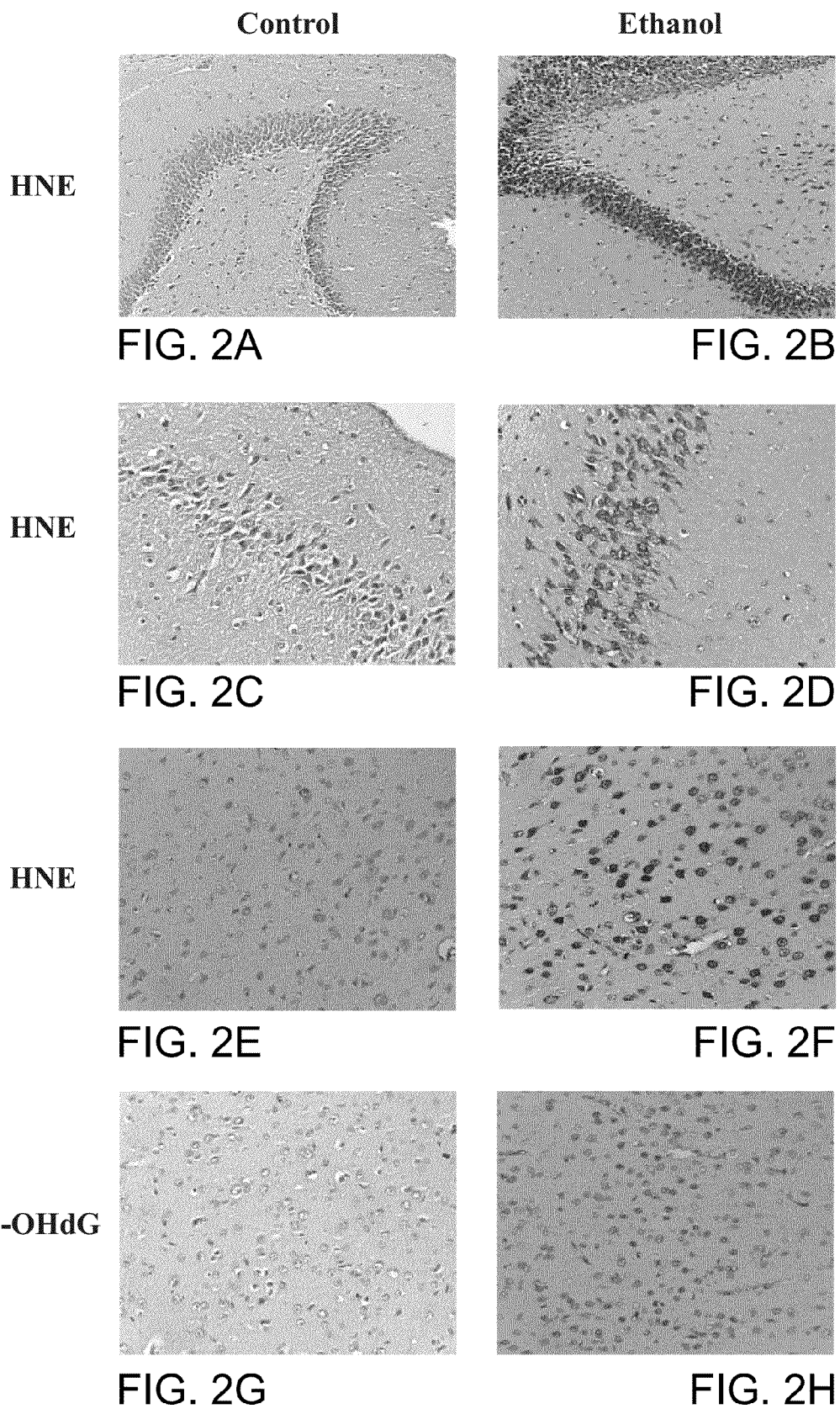

TREATMENT, PREVENTION, AND REVERSAL OF ALCOHOL-INDUCED BRAIN DISEASE

RELATED APPLICATIONS

This application is a national stage application, filed under 35 U.S.C. §371, of International Application No. PCT/US2007/019626, filed on Sep. 10, 2007, which claims the benefit of U.S. Ser. No. 60/842,988 filed Sep. 8, 2006.

INCORPORATION-BY-REFERENCE OF SEQUENCE LISTING

The contents of the text file named "21486-092N01US_ST25.txt", which was created on Jan. 4, 2016 and is 11 KB in size, are hereby incorporated by reference in their entireties.

BACKGROUND OF THE INVENTION

1. Field of the Invention

This invention is in the field of medical therapy. In particular, the invention relates to methods for treating, preventing, or reversing brain disease or damage produced by chronic alcohol intake or fetal exposure to alcohol by administering a peroxisome proliferator activated receptor (PPAR) agonist.

2. Related Art

Alcohol dependence and abuse are among the most costly healthcare problems in the world, and their impact continues to grow due to the rising incidence of heavy alcohol drinking among women and young people in general. Excessive drinking can cause cognitive dysfunction and permanent structural damage to the brain. Although Wernicke-Korsakoff syndrome is one of the most devastating and clinically significant forms of alcohol-associated neurodegeneration, its etiology is largely related to thiamine deficiency which is preventable. In contrast, the pathogenesis of more prevalent alcohol-associated brain lesions, including white matter attrition, ventriculomegaly, cerebellar degeneration, and neuronal loss within the superior frontal association cortex, anterior cingulate region, and hypothalamus, which result in cognitive and motor deficits, has not been determined.

In the central nervous system (CNS), neuronal survival, energy metabolism, and plasticity, which are critical for maintaining cognitive and motor functions, are regulated through the actions of insulin and insulin-like growth factors (IGF) types I and II. Insulin, IGF-I and IGF-II, and their corresponding receptors are abundantly expressed in various cell types throughout the brain, including neurons (Goodyer et al., *Endocrinology* 114:1187 (1984); Gammeltoft et al., *Biochimie* 67:1147 (1985); Hill et al., *Neuroscience* 17:1127 (1986)). In vitro and in vivo experiments demonstrated that insulin and IGF signaling pathways utilized by CNS neurons are virtually identical to those characterized in peripheral organs such as liver. The highest levels of insulin and IGF polypeptide and receptor gene expression in the brain are distributed in the hypothalamus, temporal lobe, and cerebellum, which notably represent major targets of ethanol neurotoxicity.

Studies involving the immature brain showed that ethanol inhibition of insulin and IGF signaling (Zhang et al., *J. Neurochem.* 71:196 (1998); de la Monte et al., *Cell. Mol. Life Sci.* 58:1950 (2001); de la Monte et al., *Alcohol Clin. Exp. Res.* 24:716 (2000); Hallak et al., *Alcohol Clin. Exp. Res.* 25:1058 (2001)) downstream through the PI3 kinase-Akt pathway (Zhang et al., *J. Neurochem.* 71:196 (1998); de la Monte et al., *Cell. Mol. Life Sci.* 58:1950 (2001); de la Monte et al., *Cell. Mol. Life Sci.* 59:882 (2002); Ramachandran et al., *Alcohol Clin. Exp. Res.* 25:862 (2001)) results in increased apoptosis (Ikonomidou et al. *Science* 287:1056 (2000); Zhang et al., *J. Neurochem.* 71:196 (1998); de la Monte et al., *Cell. Mol. Life Sci.* 58:1950 (2001)) and mitochondrial dysfunction (de la Monte et al., *Cell. Mol. Life Sci.* 58:1950 (2001); de la Monte et al., *Cell. Mol. Life Sci.* 59:882 (2002); Ramachandran et al., *Alcohol Clin. Exp. Res.* 25:862 (2001)). Ethanol inhibition of insulin signaling in the brain is mediated by insulin depletion and insulin/IGF resistance (Soscia et al., *Cell. Mol. Life Sci.*, in press (2006)). Ethanol-induced insulin/IGF resistance is manifested by impaired ligand binding to the corresponding receptors, reduced activation of the receptor tyrosine kinases, and reduced signaling downstream through cell survival pathways. However, little is known about the effects of chronic ethanol abuse on insulin and IGF signaling mechanisms in the adult human brain.

Ethanol exposure during development is the leading preventable cause of mental retardation in Europe and North America. Heavy or chronic gestational exposure to ethanol causes fetal alcohol syndrome (FAS), which encompasses a broad array of neurological and systemic lesions including CNS malformations such as microencephaly, reduced cerebral white matter volume, ventriculomegaly, cerebellar hypoplasia, and disorders of neuronal migration (Clarren et al. *J. Pediatr.* 92:64 (1978); Mattson et al., *Alcohol Res. Health* 25:185 (2001)). However, much less is known about the full range of human CNS disease produced by lower levels of ethanol exposure due to the lack of accurate clinicopathological correlative data. Experimental models of FAS have provided insight about the range of ethanol-induced CNS abnormalities by demonstrating that gestational exposure to ethanol impairs neuronal survival, growth, migration, synaptogenesis, maturation, neurotransmitter function, and intracellular adhesion (Maier et al., *Alcohol* 23:49 (2001); Minana et al., *J. Neurochem.* 75:954 (2000); Olney et al., *Apoptosis* 5:515 (2000); Swanson et al., *Alcohol Clin. Exp. Res.* 19:1252 (1995); Yanni et al., *Brain Res. Dev. Brain Res.* 120:233 (2000); Liesi et al., *J. Neurosci. Res.* 48:439 (1997)). In addition, experimental models of FAS have provided evidence that ethanol can exert neurotoxic effects on the developing CNS, even after relatively short durations or low levels of exposure (Maier et al., *Alcohol* 23:49 (2001)). Therefore, with regard to human beings, there is concern that low or moderate levels of in utero ethanol exposure can have significant adverse effects on the developing brain, and may be responsible for the growing incidence of attention deficit/hyperactivity disorders (O'Malley et al., *Can. J. Psychiatry* 47:349 (2002); Burd et al., *Neurotoxicol. Teratol.* 25:697 (2003); Burd et al., *Neurotoxicol. Teratol.* 25:681 (2003)).

Neuronal genesis, differentiation, and migration are critical on-going processes likely to be perturbed by gestational exposure to ethanol. In the developing CNS, insulin, IGF-I, and IGF-II receptors are abundantly expressed (Goodyer et al., *Endocrinology* 114:1187 (1984); Gammeltoft et al., *Biochimie* 67:1147 (1985); Hill et al., *Neuroscience* 17:1127 (1986)), and their corresponding growth factors mediate neuronal growth, survival, energy metabolism, and synapse formation. In addition, there is growing evidence that insulin and IGF signaling mechanisms are key targets of ethanol-mediated neurotoxicity in the immature CNS (Zhang et al. *J. Neurochem.* 71:196 (1998); de la Monte et al. *Cell. Mol. Life Sci.* 58:1950 (2001); de la Monte et al., *Alcohol Clin. Exp. Res.* 24:716 (2000); Hallak et al., *Alcohol Clin. Exp. Res.* 25:1058 (2001)). Neuronal loss that is associated with ethanol-induced microencephaly is mediated by inhibition of insulin/IGF-I-stimulated survival signaling (Zhang et al., *J. Neurochem.* 0.71:196 (1998); de la Monte et al., *Cell. Mol. Life Sci.* 58:1950 (2001); de La Monte et al., *Cell. Mol. Life Sci.* 59:882 (2002); Ramachandran et al., *Alcohol Clin. Exp. Res.* 25:862 (2001)), and attendant increased apoptosis (Zhang et al., *J. Neurochem.* 71:196 (1998); de la Monte et al., *Cell. Mol. Life Sci.* 58:1950 (2001); Ikonomidou et al., *Science* 287:1056 (2000)) and mitochondrial dysfunction (de la Monte et al., *Cell. Mol. Life Sci.* 58:1950 (2001); de la Monte et al., *Cell. Mol. Life Sci.* 59:882 (2002); Ramachandran et al., *Alcohol Clin. Exp. Res.* 25:862 (2001); de la Monte et al. *Alcohol Clin. Exp. Res.* 25:898 (2001)).

Recent studies designed to divulge the mechanisms of ethanol-impaired insulin/IGF signaling in the developing brain demonstrated that chronic gestational exposure to relatively high levels of ethanol inhibit insulin gene expression, but produce only modest alterations in the expression of insulin and IGF-I receptors (de la Monte et al., *Cell. Mol. Life Sci.* 62:1131 (2005)). Although those results suggest that cell loss in ethanol-exposed developing brains may be mediated by a local deficiency of brain-derived insulin, the finding of reduced levels of insulin and IGF-I receptor tyrosine kinase activities following exogenous growth factor stimulation, suggests additional abnormalities contribute to the impairments in CNS development. Moreover, in vitro experiments demonstrated ethanol-inhibition of IGF-I and IGF-II, but not insulin receptor expression, yet insulin and IGF-I stimulated glucose uptake and ATP synthesis were similarly impaired (de la Monte et al., *Cell. Mol. Life Sci.* 62:1131 (2005)). Therefore, the mechanisms by which ethanol adversely affects insulin and IGF-I responsiveness in neurons require further investigation.

SUMMARY OF THE INVENTION

A relationship between alcohol-induced brain damage and insulin resistance has been demonstrated by the finding of impaired insulin response and alterations in the insulin/IGF pathways in the brain of animals with chronic alcohol intake and in the brain of fetal animals exposed to alcohol. These findings define a connection between both alcohol-induced brain damage in adults and Fetal Alcohol Syndrome (FAS) and the insulin/IGF signaling pathway that may be exploited for therapeutic purposes.

This invention relates to the surprising discovery that administration of certain peroxisome proliferator activated receptor (PPAR) agonists strikingly inhibit oxidative stress and DNA damage in the brain using animal models of alcohol-induced brain damage. The net effect is to attenuate or prevent ongoing brain injury produced by ethanol. This invention has major implications for the treatment of alcohol-related adult and fetal brain damage.

Thus, one aspect of the present invention is directed to methods for treating, preventing, or reversing alcohol-induced brain disease in an animal, comprising administering to said animal a therapeutically effective amount of a PPAR agonist.

Another aspect of the invention is directed to methods for treating, preventing, or reversing brain damage produced by chronic alcohol intake in an animal, comprising administering to said animal a therapeutically effective amount of a PPAR agonist.

In one embodiment, the invention relates to methods for treating, preventing, or reversing cognitive impairment produced by chronic alcohol intake in an animal, comprising administering to said animal a therapeutically effective amount of a PPAR agonist.

In one embodiment, the invention relates to methods for treating, preventing, or reversing insulin resistance in the brain of an animal produced by chronic alcohol intake, comprising administering to said animal a therapeutically effective amount of a PPAR agonist.

In a further embodiment, the invention relates to methods for treating, preventing, or reversing brain damage produced in the brain of a fetal animal by chronic alcohol intake by the parent, comprising administering to said animal or to said parent a therapeutically effective amount of a PPAR agonist.

Surprisingly, it has been discovered that PPAR agonists are particularly effective for treatment and prevention of brain damage in chronic ethanol-fed animals. Thus, it is expected that human subjects who are chronic alcohol drinkers or who suffer from alcohol-induced brain damage or brain disease may be administered PPAR agonists to prevent or slow down further brain damage and to treat or ameliorate the symptoms of brain damage or brain disease. Further, it is expected that pregnant women who are chronic alcohol drinkers may be administered PPAR agonists to prevent or slow down further brain damage to the fetuses they are carrying and to treat or ameliorate the symptoms of brain damage or brain disease exhibited by the fetuses.

The invention further provides an animal model of alcohol-induced brain damage and disease produced by chronically feeding ethanol to Long-Evans rats. Surprisingly, it has been discovered that Long-Evans rats exhibit a robust response to ethanol feeding compared to other rat strains that make the rats ideally suited for the study of the effects of chronic alcohol intake. In one embodiment, ethanol is included in the daily diet of Long-Evans rats. For example, ethanol may comprise about 0%, 2%, 4.5%, 6.5%, 9.25% (v/v) (equivalent to 0%, 8%, 18%, 26%, or 37% of the caloric content) or more of the daily diet.

The invention further relates to a method for screening for an agent that is potentially useful for the treatment, prevention or reversal of alcohol-induced brain damage or disease, comprising administering an agent to the animal model produced by chronically feeding ethanol to Long-Evans rats and determining the level of brain damage, cognitive impairment, and/or insulin resistance relative to the level in a control animal that has not had the agent administered, wherein an improvement in the level of brain damage, cognitive impairment, and/or insulin resistance relative to the level in a control animal that has not had the agent administered indicates that the agent is potentially useful for the treatment, prevention or reversal of alcohol-induced brain damage or disease.

The invention additionally provides a method for testing a potential treatment for treatment, prevention or reversal of alcohol-induced brain damage or disease, comprising administering the potential treatment to the animal model produced by chronically feeding ethanol to Long-Evans rats and determining the level of brain damage, cognitive impairment, and/or insulin resistance relative to the level in a control animal that has not had the potential treatment administered, wherein an improvement in the level of brain damage, cognitive impairment, and/or insulin resistance relative to the level in a control animal that has not had the potential treatment administered indicates that the treatment is potentially useful for the treatment, prevention or reversal of alcohol-induced brain damage or disease.

BRIEF DESCRIPTION OF THE DRAWINGS/FIGURES

FIGS. 1A-1H show that chronic ethanol feeding causes cerebellar degeneration in adult rats (control: A, C, E, G; 37% ethanol diet: B, D, F, H). A-D: Histological sections stained with hematoxylin and eosin. E, F: Adjacent sections immunostained with monoclonal antibodies to HNE to detect lipid peroxidation. G, H: Adjacent sections immunostained with monoclonal antibodies to 8-OHdG to detect DNA damage. A, B: Low magnification (100×) images demonstrate the effects of ethanol on the cytoarchitecture of the cerebellar cortex (arrows point to the Purkinje cell layer; ML=molecular layer; GC=granule cell layer; wm=white matter). C, D: Higher magnification (450×) images illustrate ethanol-associated reductions in cell density within the granule cell layer.

FIGS. 2A-2H show increased lipid peroxidation and DNA damage in the hippocampus and temporal cortex of ethanol-fed adult rats (control: A, C, E, G; 37% ethanol diet: B, D, F, H). A-F: Histological sections immunostained with monoclonal antibodies to HNE to detect lipid peroxidation. G, H: Histological sections immunostained with monoclonal antibodies to 8-OHdG to detect DNA damage. A, B: HNE immunoreactivity in the dentate region (CA4) of the hippocampus. C, D: HNE immunoreactivity in the CA1 region of Ammon's horn of the hippocampal formation. Note labeling of pyramidal neurons in the ethanol-fed rat brain. E, F: HNE immunoreactivity in the temporal cortex adjacent to the hippocampus. G, H: 8-OHdG immunoreactivity in the temporal cortex adjacent to the hippocampus.

FIGS. 3A-3L show pathological shifts in brain cell populations following chronic ethanol exposure. Cell specific gene expression was measured in samples of temporal cortex (A, D, G, J), hypothalamus (B, E, H, K), and cerebellum (C, F, I, L). The mRNA transcript levels corresponding to Hu neuronal RNA binding protein (A-C), myelin-associated glucoprotein-1 (D-F), astrocytic glial fibrillary acidic protein (G-D), and endothelin-1 (J-L) were used to detect pathological shifts in brain cell types. Graphs depict the mean±S.D. of results. Data were analyzed statistically using Student t-tests. Significant P-values are indicated over the bar graphs.

FIGS. 4A-4I show alterations in insulin, IGF-I, and IGF-II gene expression in brains of chronic ethanol-fed adult male rats. mRNA transcript levels corresponding to insulin (A-C), IGF-I (D-F), and IGF-II (G-I) were measured in the temporal cortex (A, D, G), hypothalamus (B, E, H), and cerebellum (C, F, I). Graphs depict the mean±S.D. of results. Data were analyzed statistically using Student t-tests. Significant P-values are indicated over the bar graphs.

FIGS. 5A-5I show alterations in insulin, IGF-I, and IGF-II receptor gene expression in brains of chronic ethanol-fed adult male rats. mRNA transcript levels corresponding to insulin receptor (A-C), IGF-IR (D-F), and IGF-IIR (G-I) were measured in the temporal cortex (A, D, G), hypothalamus (B, E, H), and cerebellum (C, F, I). Graphs depict the mean±S.D. of results. Data were analyzed statistically using Student t-tests. Significant P-values are indicated over the bar graphs.

FIGS. 6A-6I show that chronic ethanol feeding impairs insulin, IGF-I, and IGF-II receptor binding in the brain. Equilibrium binding assays were performed on protein extracts from temporal cortex (A, C, E), hypothalamus (B, D, F), or cerebellar membrane (C, F, I). Graphs depict the mean±S.D. of results obtained for insulin (A-C), IGF-I (D-F), and IGF-II (G-I) specific binding. Data were analyzed statistically using Student T-tests. Significant P-values are indicated over the bar graphs.

FIGS. 7A-7F show the effects of chronic ethanol feeding on acetylcholine homeostasis. mRNA transcripts for choline acetyltransferase (A-C) and acetyl cholinesterase (D-F) were measured in the temporal cortex (A, D), hypothalamus (B, E), and cerebellum (C, F) of control and chronic ethanol-fed rats. Graphs depict the mean±S.D. of results. Data were analyzed statistically using Student t-tests. Significant P-values are indicated over the bar graphs.

FIGS. 8A-8F show alterations in insulin, IGF-I, and IGF-II gene expression in brains of chronic alcoholics. Cingulate gyrus (A, C, E) and cerebellar vermis (B, D, F) expression levels of insulin (A, B), IGF-I (C, D), and IGF-II (E, F) mRNA transcripts were measured. The graphs depict the mean±S.D. of results from 6 subjects per group. Data were analyzed statistically using Student T-tests. Significant P-values are indicated over the bar graphs.

FIGS. 9A-9F show alterations in insulin, IGF-I, and IGF-II receptor gene expression in brains of chronic alcoholics. Cingulate gyrus (A, C, E) and cerebellar vermis (B, D, F) expression levels of insulin receptor (A, B), IGF-I receptor (C, D), and IGF-II receptor (E, F) mRNA transcripts were measured. The graphs depict the mean±S.D. of results from 6 subjects per group. Data were analyzed statistically using Student T-tests. Significant P-values are indicated over the bar graphs.

FIGS. 10A-10F show the effects of chronic alcohol abuse on insulin receptor substrate (IRS) gene expression. Cingulate gyrus (A, C, E) and cerebellar vermis (B, D, F) expression levels of IRS-1 (A, B), IRS-2 (C, D), and IRS-4 (E, F) mRNA transcripts were measured. The graphs depict the mean±S.D. of results from 6 subjects per group. Data were analyzed statistically using Student T-tests. Significant P-values are indicated over the bar graphs.

FIGS. 11A-11F show that chronic alcohol abuse impairs insulin, IGF-I, and IGF-II receptor binding in the human brain. Equilibrium binding assays were performed on membrane protein extracts from cingulate gyrus (A, C, E) or cerebellum (B, D, F). Graphs depict the mean±S.D. of results obtained for insulin (A, B), IGF-I (C, D), and IGF-II (E, F) specific binding. Data were analyzed statistically using Student T-tests. Significant P-values are indicated over the bar graphs.

FIGS. 12A-12D show the effects of chronic alcohol abuse on acetylcholine homeostasis. Cingulate gyrus (A, C) and cerebellar vermis (B, D) expression levels of choline acetyltransferase (A, B) and acetyl cholinesterase (C, D) mRNA transcripts were measured. The graphs depict the mean±S.D. of results from 6 subjects per group. Data were analyzed statistically using Student T-tests. Significant P-values are indicated over the bar graphs.

Figure 13A:
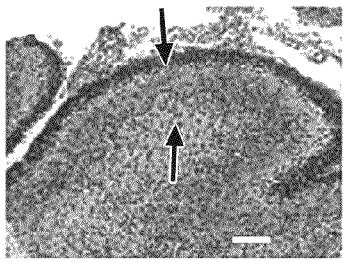
Figure 13B:
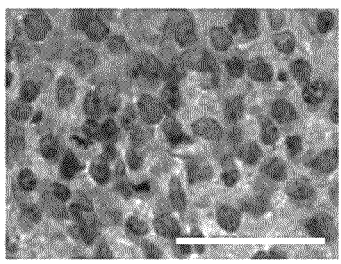
Figure 13C:
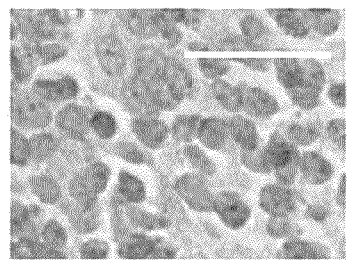
Figure 13D:
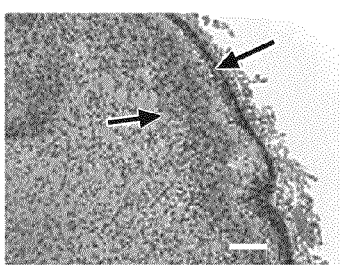
Figure 13E:
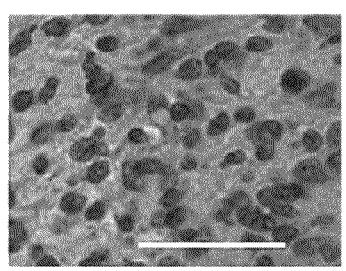
Figure 13F:
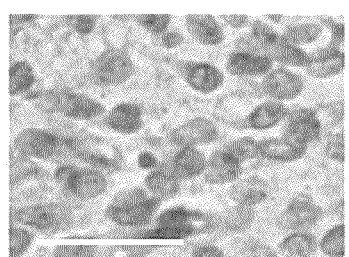
Figure 13G:
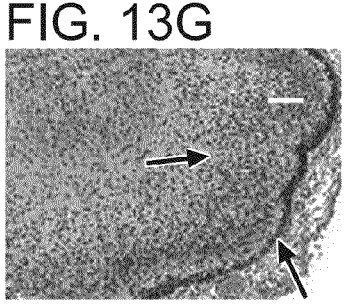
Figure 13H:
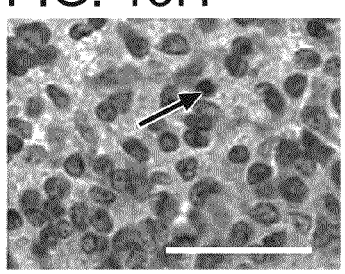
Figure 13I:
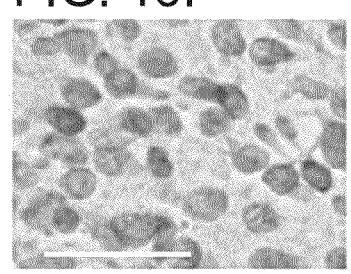
Figure 13J:
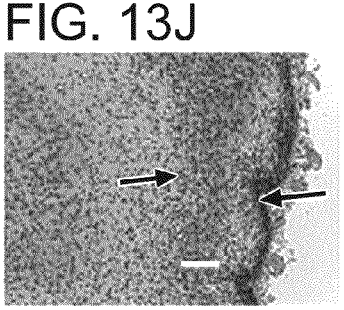
Figure 13K:
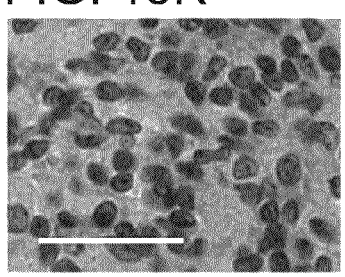
Figure 13L:
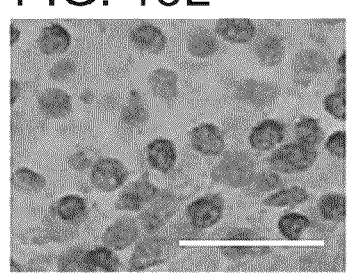
Figure 13M:
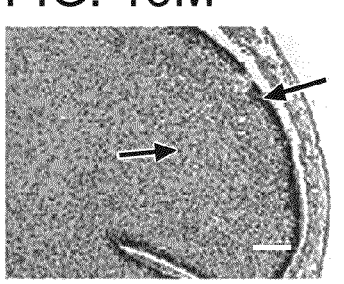
Figure 13N:
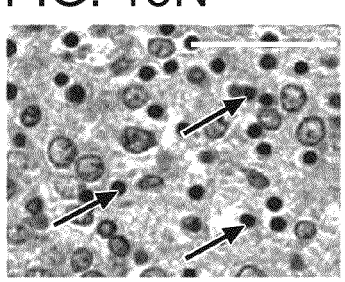
Figure 13O:
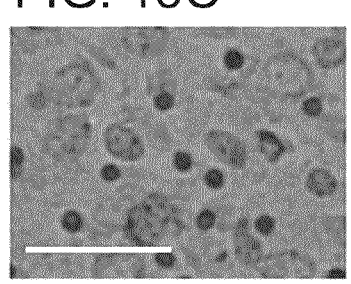
Figures 14A, 14B, 14C, 14D, 14E:
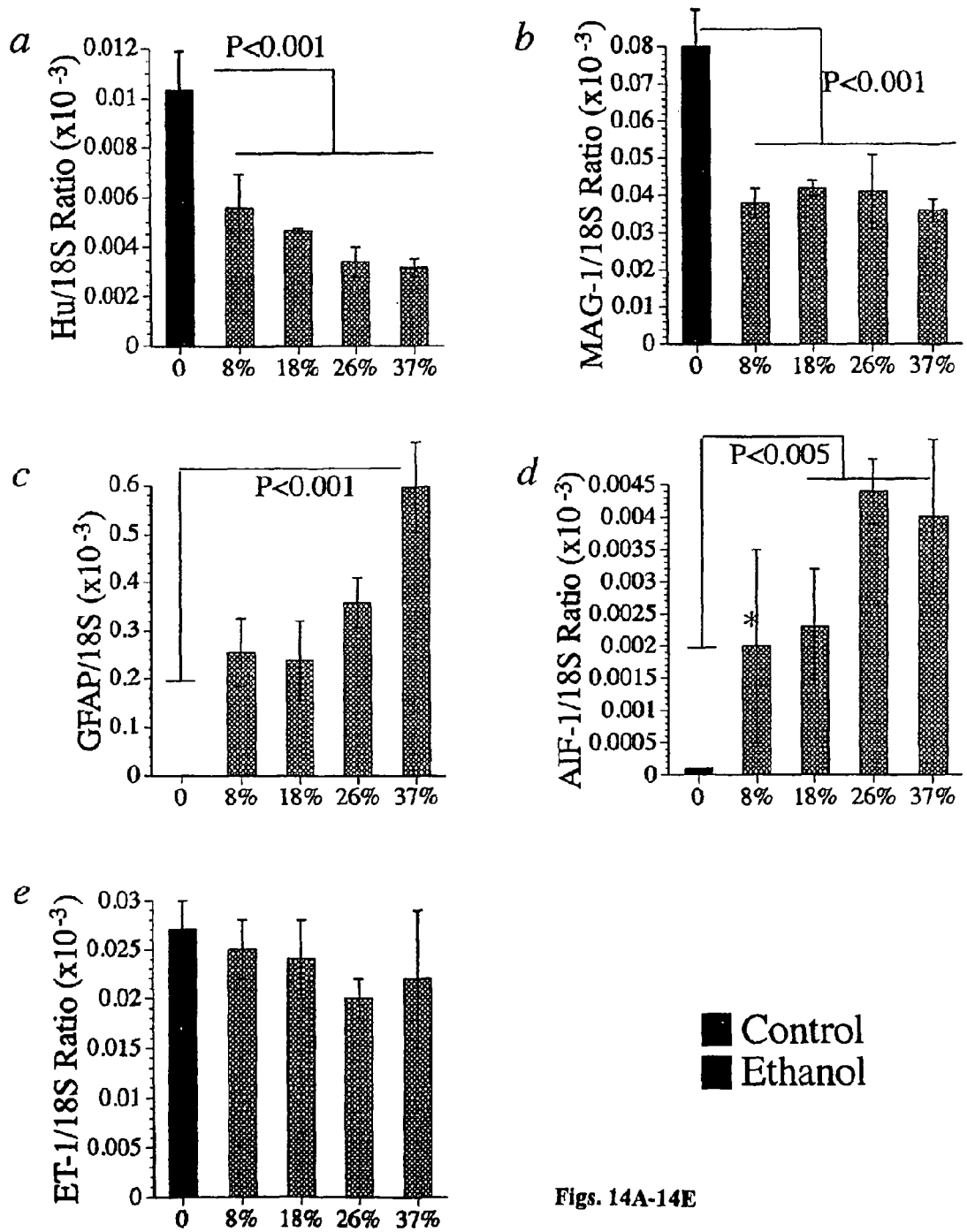

FIGS. 13A-13O show the effects of chronic gestational exposure to different levels of ethanol on cerebellar development. Pregnant dams were fed with Lieber-DiCarli isocaloric liquid diets containing 0% (control; A-C), 8% (D-F), 18% (G-I), 26% (J-L), or 37% (M-O) ethanol by caloric content, or 0%, 2%, 4.5%, 6.5%, or 9.25% v/v ethanol. Histological sections of brain were stained with hematoxylin and eosin (A, B, D, E, G, H, J, K, M, N). Low magnification images were used to demonstrate the effects of ethanol on the structure of the cerebellar cortex including foliation and delineation of the cortical lamination (A, D, G, J, M; arrows along the top or right side of the image point to the external granule cell layer, whereas the arrows pointing from the left or bottom of the image indicate the inner zone of the internal granule cell layer; Scale bars=60 μm). Higher magnification images (B, E, H, K, N; Scale bars=40 μm) illustrate the relative density of cells within the internal granule cell layer. Arrows in H and N show condensed pyknotic nuclei. To detect DNA damage, adjacent histological sections were immunostained with antibodies to single-stranded (nicked or fragmented) DNA (C, F, I, L, O). Note the nuclear immunoreactivity for single-stranded DNA (Scale bars=25 μm).

FIGS. 14A-14E show pathological shifts in cerebellar cell populations following chronic gestational exposure to ethanol. mRNA expression corresponding to (A) neurons (Hu), (B) oligodendroglia (myelin-associated glycoprotein-1), (C) astrocytes (glial fibrillary acidic protein), (D) microglia (allograft inflammatory factor-1), and (E) endothelial cells (endothelin-1) was determined. Graphs depict the mean±S.E.M. levels of gene expression in cerebellar tissue from 12 rat pups per group. Inter-group comparisons were made using ANOVA with the post-hoc Tukey-Krammer significance test. Significant P-values relative to control are indicated above the bars or with an asterisk ($*P<0.05$).

FIGS. 15A-15H show the effects of chronic gestational exposure to different levels of ethanol on cerebellar expression of growth factor and growth factor receptor genes. Gene expression corresponding to insulin (A), insulin receptor (B), IGF-I (C), IGF-IR (D), IGF-II (E), and IGF-IIR (F) mRNA transcripts, and 18S (G) and 28S (H) ribosomal RNA was measured using cerebellar tissue from 9 rat pups per group. Data were analyzed statistically using ANOVA with the Tukey-Kramer post-hoc significance test. Significant P-values relative to control are indicated above the bars or with an asterisk ($*P<0.05$).

Figure 16A:
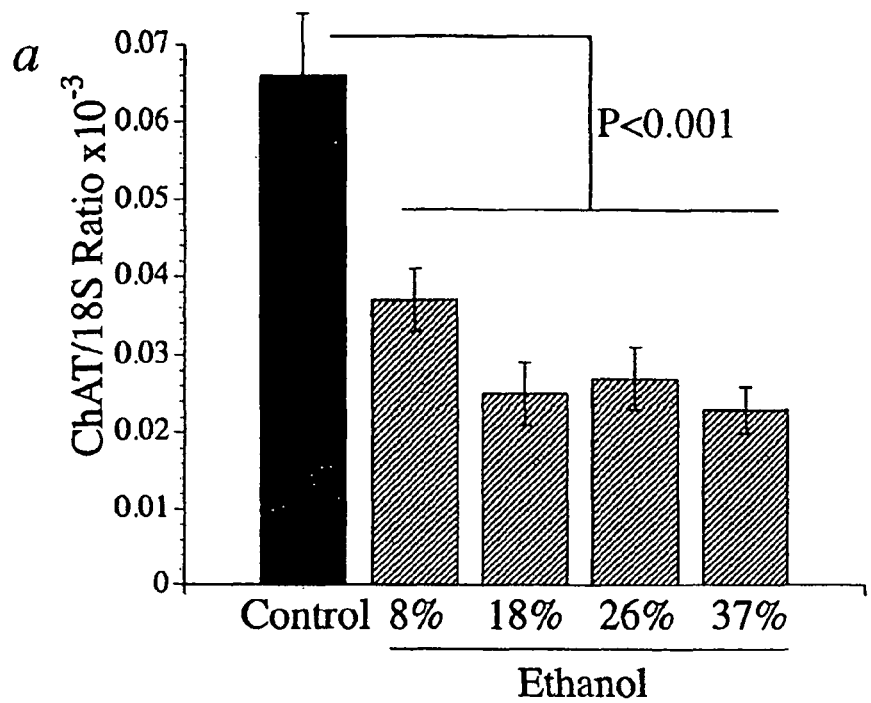
Figure 16B:
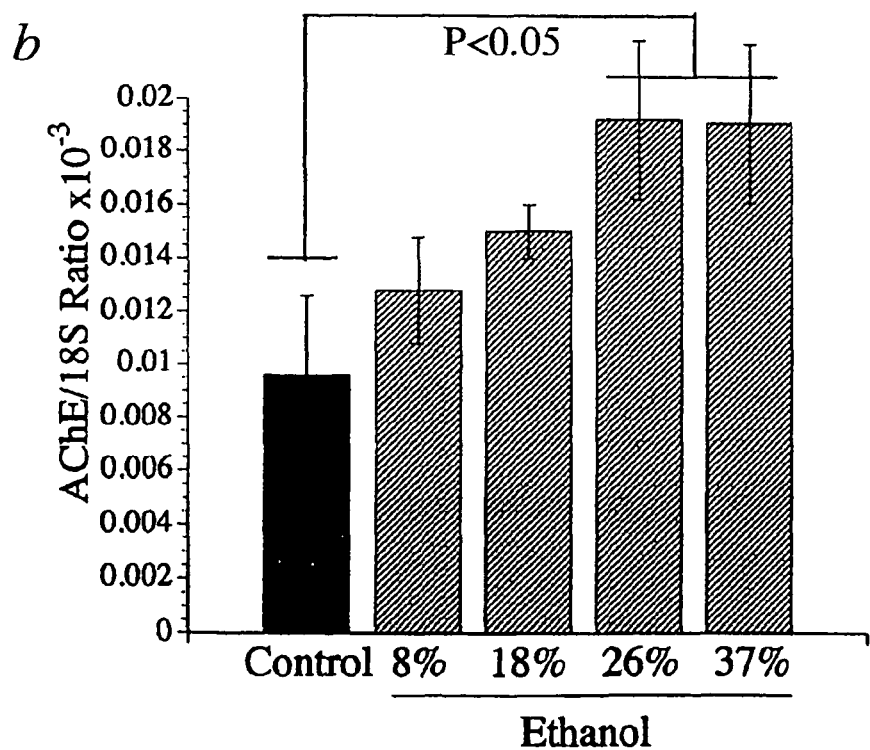

FIGS. 16A-16B show ethanol dose effects on cerebellar expression of choline acetyltransferase (A) and acetylcholinesterase (B). Gene expression was measured using cerebellar tissue from 10 rat pups per group. Data were analyzed statistically using ANOVA with the Tukey-Krammer post-hoc significance test. Significant P-values relative to control are indicated above the bars.

FIGS. 17A-17F show the effects of short-term in vitro ethanol exposure on insulin (A), IGF-I (B), and IGF-II (C) receptor binding and insulin, IGF-I, and IGF-II stimulated levels of ATP (D), ChAT (E), and AChE (F). Graphs depict the mean±S.E.M. of fmol/mg of specifically bound ligand. Data were analyzed statistically using the Student T-test. Significant P-values are indicated over the bar graphs. Data for ATP, ChAT, and AChE (counts per second; CPS) generated from 16 micro-cultures were averaged and representative results are depicted graphically (Mean±S.E.M.). Results were analyzed statistically using ANOVA with the Tukey-Kramer post-hoc significance test. Significant P-values relative to the corresponding cultures in the control group are indicated over the bars, and significant differences relative to the same group un-stimulated controls are indicated by the asterisks ($*P<0.05$ or better).

FIGS. 18A-18F show the potential role of decreased membrane cholesterol content in relation to impaired insulin and IGF receptor binding and signal transduction following ethanol exposure. Cholesterol content was measured in the protein extracts of (A) control and ethanol-exposed rat pup cerebellar membranes (N=8 pups per group) and (B) cerebellar neuron cultures. To determine the effects of cholesterol depletion or repletion on growth factor binding, control and ethanol-exposed cerebellar neuron cultures were incubated with vehicle, 10 mM methyl-β-cyclodextrin (MβCD), or 10 mM cholesterol in Locke's buffer for 3 hrs at 37° C. The cells were analyzed for (C) membrane cholesterol content and equilibrium binding (fmol/mg protein) to the insulin (D), IGF-I (E), or IGF-H (F) receptors. The graphs depict the mean±S.E.M. of results. Data were analyzed using ANOVA with the post-hoc Tukey-Kramer significance test. Significant P-values relative to vehicle-treated controls (within group) are indicated by asterisks ($*P<0.05$ or better). Significant between-group (control versus corresponding ethanol-treated) differences are indicated by the horizontal lines over the bars.

FIGS. 19A-19L show the effects of MβCD or cholesterol treatment on basal and insulin, IGF-I, or IGF-II-stimulated neuronal viability (A-C), ATP content (D-F), ChAT (G-D), and AChE (J-L) expression in control and ethanol-exposed (50 mM for 96 hours) primary cerebellar neuron cultures seeded into 96-well plates. Control and ethanol-exposed cells were treated with vehicle (A, D, G, J), 10 mM MβCD (B, E, H, K), or 10 mM cholesterol (C, F, I, L) in Locke's buffer for 3 hrs at 37° C., and then stimulated with vehicle (VEH), 10 nM insulin (IN), 10 nM IGF-I, or 25 nM IGF-II in serum-free medium for 12 hours. Replicate cultures (N=24) were analyzed for each assay. The graphs depict the mean±S.E.M. of results. Data were analyzed using ANOVA with the post-hoc Tukey-Kramer significance test. $*P<0.05$ or better for comparisons between control and ethanol-exposed cells for each condition. $+P<0.05$ or better for within-group comparisons to the corresponding vehicle-treated cells.

DETAILED DESCRIPTION OF THE INVENTION

The present invention relates to the important role played by increased insulin resistance in the occurrence of alcohol-induced brain damage and disease and FAS and the ability of PPAR agonists to prevent or treat the brain damage. Administration of PPAR agonists to animals that chronically ingest alcohol reduces or prevents the brain damage that occurs in response to the alcohol intake, including damage due to oxidative stress (e.g., lipid peroxidation) and DNA damage. Therefore, the invention relates to methods for treating, preventing, or reversing alcohol-induced brain disease in an animal, comprising administering to said animal a therapeutically effective amount of a PPAR agonist.

Another aspect of the invention is directed to methods for treating, preventing, or reversing brain damage produced by chronic alcohol intake in an animal, comprising administering to said animal a therapeutically effective amount of a PPAR agonist.

In one embodiment, the invention relates to methods for treating, preventing, or reversing insulin resistance in the brain of an animal produced by chronic alcohol intake, comprising administering to said animal a therapeutically effective amount of a PPAR agonist.

In a further embodiment, the invention relates to methods for treating, preventing, or reversing brain damage produced in the brain of a fetal animal by chronic alcohol intake by the parent, comprising administering to said animal a therapeutically effective amount of a PPAR agonist.

The term "alcohol-induced brain damage or disease," as used herein, refers to the spectrum of clinical pathologic changes in the brain caused by ethanol intake. Such pathologies include white matter attrition, ventriculomegaly, cerebellar degeneration, neuronal loss within the superior frontal association cortex, anterior cingulate region, and hypothalamus, which result in cognitive and motor deficits, fetal alcohol syndrome, microencephaly, cerebellar hypoplasia, and disorders of neuronal migration.

The term "chronic alcohol intake," as used herein, refers to the consumption by an animal of at least about 0.1 g pure alcohol (ethanol) per kg body weight per day on average, e.g., at least about 0.2, 0.3, 0.4, 0.5, 1, 2, 3, 4, or 5 g/kg/day on average. For a human, chronic alcohol intake is considered to be at least about 10 g pure alcohol per day on average, e.g., at least about 20, 30, 40, 50, 60, 70, 80, 90, or 100 g/day on average.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of brain damage, in one embodiment, a therapeutically effective amount will refer to the amount of a therapeutic agent that decreases the number of damaged brain cells or slows the rate of increase in the number of damaged brain cells by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

In a further embodiment, a therapeutically effective amount will refer to the amount of a therapeutic agent that increases a biological function of the brain by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Brain function can be measured using assays that are routine in clinical medicine, including without limitation measurement of brain waves (e.g., by electroencephalography) or cognitive ability. Cognitive behavior may be measured by any one of several tests (See Gershon et al., Clinical Evaluation of Psychotropic Drugs: Principles and Guidelines, Prien and Robinson (eds.), Raven Press, Ltd., New York, 1994, p. 467). One such test, BCRS, is designed to measure only cognitive functions: concentration, recent memory, past memory, orientation, functioning, and self-care. The most frequently used instrument to evaluate cognitive impairment is the Mini-Mental State Examination (MMSE) (see Cockrell, J. R., et al., Psychopharmacology 1988; 24:689-692, Crumb, R. M., et al. JAMA 1993; 269: 2386-2391). The MMSE includes measures of memory, orientation to place and time, naming, reading, copying (visuospatial organization), writing, and the ability to follow a three-stage command. A score of less than 24 points on the MMSE is generally accepted as signifying cognitive impairment. The Blessed Information Memory Concentration instrument (Blessed, G., et al., Br. J. Psychiatry 1968; 114: 797-811) primarily evaluates orientation, memory, and concentration. The Blessed Orientation Memory Concentration instrument (Katzman, R., et al., Am. J. Psychiatry 1983; 140:734-739) assesses orientation to time, recall of a short phrase, the ability to count backward, and the ability to recite months in reverse order. The Short Test of Mental Status (Kokmen, E., et al., Mayo Clin. Proc., 1987; 62(4):281-289) evaluates orientation, attention, recall, concentration, abstraction, clock drawing, and copying. The Functional Activities Questionnaire (Pfeffer, R. I., et al., J. Gerontol. 1982; 37:323-329) employs responses from a family member or a friend of the subject to evaluate functional activities that may be impaired.

In a further embodiment, a therapeutically effective amount will refer to the amount of a therapeutic agent that improves the structure of the brain or slows down the degeneration of the structure of the brain by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Brain structure can be determined using imaging techniques that are routine in clinical medicine, including without limitation magnetic resonance imaging, computed axial tomography, single photon emission computed tomography, positron emission tomography, X-ray, and ultrasound.

In an additional embodiment, a therapeutically effective amount will refer to the amount of a therapeutic agent that decreases insulin resistance in the brain by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Insulin resistance can be measured using assays that are routine in the art and those that are discussed herein, including without limitation measurement of insulin binding to the insulin receptor, glucose tolerance tests, and expression of insulin-responsive genes.

The terms "prevent," "preventing," and "prevention," as used herein, refer to a decrease in the occurrence of pathological cells (e.g., damaged brain cells) in an animal. The prevention may be complete, e.g., the total absence of pathological cells in a subject. The prevention may also be partial, such that the occurrence of pathological cells in a subject is less than that which would have occurred without the present invention.

In one aspect of the invention, methods for treating, preventing, or reversing alcohol-induced brain disease in an animal are provided. In certain embodiments, the methods comprise the administration to the animal of a therapeutically effective amount of a PPAR agonist. The PPAR agonist may be administered prior to or after the onset of physical or histological symptoms of brain disease.

Another aspect of the invention is directed to methods for treating, preventing, or reversing brain damage produced by chronic alcohol intake in an animal. In certain embodiments, the methods comprise the administration to the animal of a therapeutically effective amount of a PPAR agonist. The PPAR agonist may be administered prior to or after the onset of physical or histological symptoms of brain damage. Brain damage may be any type of cellular or tissue damage associated with alcohol intake. For example, the damage may be associated with oxidative stress (e.g., lipid peroxidation) or DNA damage. The term "associated with," as used herein, means that the alcohol-induced brain damage is evidenced by physical (e.g., histological, serological) signs of a condition (e.g., oxidative stress or DNA damage).

In one embodiment, the invention relates to methods for treating, preventing, or reversing cognitive impairment produced by chronic alcohol intake in an animal. In certain embodiments, the methods comprise the administration to the animal of a therapeutically effective amount of a PPAR agonist. The PPAR agonist may be administered prior to or after the onset of physical or histological symptoms of cognitive impairment. In one embodiment, the cognitive impairment is not due to drunkenness. Cognitive impairment may be measured as discussed above.

In one embodiment, the invention relates to methods for treating, preventing, or reversing insulin resistance in the brain of an animal produced by chronic alcohol intake. In certain embodiments, the methods comprise the administration to the animal of a therapeutically effective amount of a PPAR agonist. The PPAR agonist may be administered prior to or after the onset of insulin resistance. Insulin resistance may be due to alcohol-induced alterations anywhere along the insulin/IGF signaling pathways, e.g., decreased expression of insulin or IGF-I, increased expression of IGF-II, decreased expression of receptors for insulin, IGF-I, or IGF-II, decreased binding of insulin, IGF-I, or IGF-II to their respective receptors, or decreased expression of insulin-responsive genes such as AAH.

Insulin resistance may be measured by detecting an alteration in the level or function of at least one factor in the insulin/IGF signaling pathway. In one embodiment, the detection of an alteration is carried out in vivo. For example, imaging techniques (e.g., magnetic resonance imaging, computed axial tomography, single photon emission computed tomography, positron emission tomography, X-ray, ultrasound) may be used in combination with detectably labeled antibodies, ligands, enzymes substrates, etc., to determine the level or function of at least one factor in the insulin/IGF signaling pathway in a subject. Examples of detectable labels include, but are not limited to, radioactive, fluorescent, paramagnetic, and superparamagnetic labels. Any suitable in vivo imaging techniques known in the art may be used in the present invention. Examples of imaging techniques are disclosed in U.S. Pat. Nos. 6,737,247, 6,676,926, 6,083,486, 5,989,520, 5,958,371, 5,780,010, 5,690,907, 5,620,675, 5,525,338, 5,482,698, and 5,223,242.

In another embodiment, the detection of an alteration is carried out in vitro, e.g., using a biological sample. A biological sample may be any tissue or fluid from a subject that is suitable for detecting the level or function of at least one factor in the insulin/IGF signaling pathway. Examples of useful samples include, but are not limited to, biopsied tissues, blood, plasma, serous fluid, cerebrospinal fluid, intraventricular fluid, saliva, urine, and lymph.

Factors in the insulin/IGF signaling pathway that may be detected and measured include, but are not limited to, insulin, insulin-like growth factor-I (IGF-I), IGF-II, insulin receptor, IGF-I receptor, IGF-II receptor, tyrosine phosphorylated insulin receptor, tyrosine phosphorylated IGF-I receptor, tyrosine phosphorylated IGF-II receptor, insulin receptor substrate-1 (IRS-1), IRS-2, IRS-4, tyrosine phosphorylated IRS-1, tyrosine phosphorylated IRS-2, tyrosine phosphorylated IRS-4, phosphatidylinositol 3-kinase (PI3 kinase), the p85 subunit of PI3 kinase, Akt, phospho-Akt, glycogen synthase kinase-3β (GSK-3β), and phospho-GSK-3β. Functions that may be measured include, but are not limited to, ligand binding capacity of the insulin receptor, IGF-I receptor, or IGF-II receptor, kinase activity of the insulin receptor, IGF-I receptor, or IGF-II receptor, interaction of the p85 subunit of PI3 kinase with phosphorylated IRS-1, IRS-2, or IRS-4, binding of phosphorylated IRS-1, IRS-2, or IRS-4 to growth factor receptor-bound protein 2 (Grb2), SHPTP-2 protein tyrosine phosphatase, or the p85 subunit of PI3 kinase, the enzymatic activity of mitogen-activated protein kinase kinase (MAPKK), Erk MAPK, Akt/Protein kinase B, GSK-3β.

The levels of factors in the insulin/IGF signaling pathway may be measured at the protein or RNA (e.g., mRNA) levels. Any method known in the art for quantitating specific proteins in a biological sample may be used in the present methods. Examples include, but are not limited to, immunoassays, Western blotting, immunoprecipitation, immunohistochemistry, gel electrophoresis, capillary electrophoresis, column chromatography, ligand binding assays, and enzymatic assays. See, e.g., Harlow et al., Antibodies: A Laboratory Manual, Cold Spring Harbor Laboratory, Cold Spring Harbor, N.Y., (1988); Ausubel et al., Current Protocols in Molecular Biology, John Wiley & Sons, New York 3rd Edition, (1995).

To measure the level of a specific RNA, any assay known in the art for the detection of nucleic acids may be used in the invention. Examples include, but are not limited to, reverse transcription and amplification assays, hybridization assays, Northern blotting, dot blotting, in situ hybridization, gel electrophoresis, capillary electrophoresis, and column chromatography. See, e.g., Ausubel et al., Current Protocols in Molecular Biology, John Wiley & Sons, New York 3rd ed., (1995); Sambrook et al., Molecular Cloning—A Laboratory Manual, 2nd ed., Vol. 1-3 (1989). The assay can detect the RNA itself or a cDNA produced by reverse transcription of the RNA. Assays can be performed directly on biological samples or on nucleic acids isolated from the samples.

In a further embodiment, the invention relates to methods for treating, preventing, or reversing brain damage produced in the brain of a fetal animal by chronic alcohol intake by the parent. In certain embodiments, the methods comprise the administration to the animal or to the parent of a therapeutically effective amount of a PPAR agonist. The PPAR agonist may be administered prior to or after the onset of brain damage. Brain damage may be any type of cellular or tissue damage associated with exposure of fetal brain to alcohol.

The methods of the invention may be carried out on animals displaying pathology resulting from brain damage or disease, animals suspected of displaying pathology resulting from brain damage or disease, and animals at risk of displaying pathology resulting from brain damage or disease. For example, those that have a genetic predisposition to alcoholism, those who are moderate drinkers but already have brain damage for other reasons, or those who find out that they are pregnant can be treated prophylactically.

PPAR agonists that may be used in the present invention include selective agonists of PPAR-α, PPAR-γ, and PPAR-δ, as disclosed in U.S. Pat. Nos. 6,713,514, 6,677,298, 6,462,046, 5,925,657, and 5,326,770 and in Combs et al. *J. Neurosci.* 20:558 (2000), as well as compounds that are agonists of multiple PPAR subtypes. The term selective is used to describe agents having greater than 10-fold, preferably greater than 100-fold, and most preferably greater than 1,000-fold activity at one PPAR receptor subtype than at another PPAR receptor subtype. Characterization of receptor affinities and functional activities for agents at PPAR receptor subtypes can be determined using methodology as described in WO 2005049572. The use of PPAR-δ agonists in brain disease patients may have an added advantage of increasing the number of type I muscle fibers, which may confer resistance to obesity and improve metabolic profiles, even in the absence of exercise (Wang et al. *PLoS Biol.* 2:3294 (2004)).

Useful PPAR-α selective agonists include without limitation clofibrate, bezafibrate, ciprofibrate, 2-bromohexadecanoic acid, etomoxir sodium hydrate, N-oleoylethanolamine, GW-9578, GW-7647, WY-14643, and compounds disclosed in U.S. Pat. Nos. 7,091,225, 7,091,230, 7,049,342, 6,987,118, 6,750,236, 6,699,904, 6,548,538, 6,506,797, 6,306,854, 6,060,515, and 6,028,109.

Useful PPAR-γ selective agonists include without limitation ciglitazone, rosiglitazone, pioglitazone, troglitazone, GW-1929, F-L-Leu, JTT-501, GI-262570, and compounds disclosed in U.S. Pat. Nos. 7,090,874, 7,060,530, 6,908,908, 6,897,235, 6,852,738, 6,787,651, 6,787,556, 6,713,514, 6,673,823, 6,646,008, 6,605,627, 6,599,899, 6,579,893, 6,555,536, 6,541,492, 6,525,083, 6,462,046, 6,413,994, 6,376,512, 6,294,580, 6,294,559, 6,242,196, 6,214,850, 6,207,690, 6,200,995, 6,022,897, 5,994,554, 5,939,442, and 5,902,726.

Useful PPAR-δ selective agonists include without limitation GW-501516, GW-0742, L-165041, and carbaprostacyclin, which are structurally defined below:

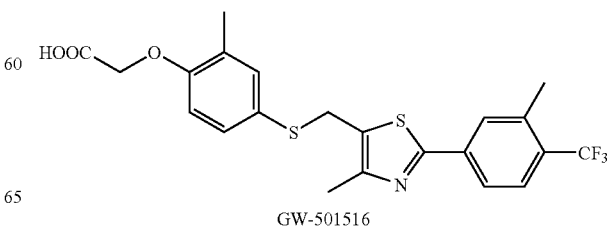

GW-501516

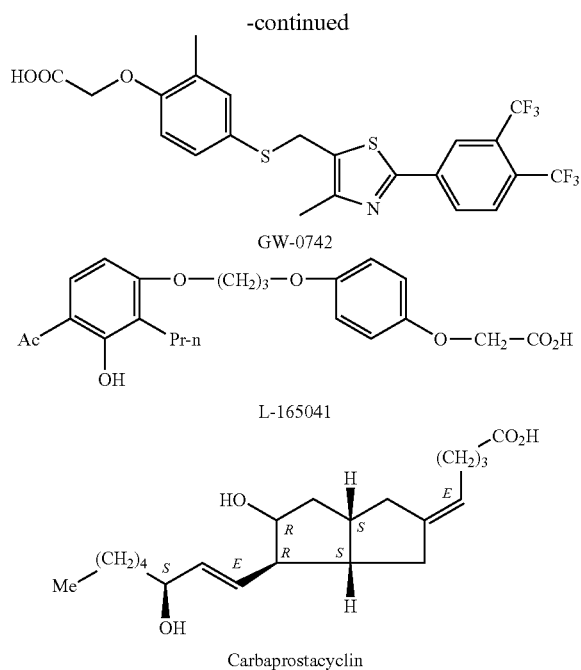

GW-0742

L-165041

Carbaprostacyclin

Other useful PPAR-δ agonists include without limitation RWJ-800025, L-160043, and compounds disclosed in U.S. Pat. Nos. 7,091,245, 7,015,329, 6,869,967, 6,787,552, 6,723,740, 6,710,053, and 6,300,364 and in EP 1586573, US 20050245589, and WO 2005049572.

Useful mixed PPAR-α/γ agonists include without limitation GW-1556, AVE-8042, AVE-8134, AVE-0847, DRF-2519, and compounds disclosed in U.S. Pat. Nos. 7,091,230, 6,949,259, 6,713,508, 6,645,997, 6,569,879, 6,468,996, 6,465,497, and 6,380,191.

Useful compounds that act as agonists at all PPAR receptors include without limitation LY-171883 and pseudolaric acid B.

Some embodiments of the present invention provide methods for administering a therapeutically effective amount of a PPAR agonist in combination with an additional agent known in the art to be useful for the treatment, prevention, or reversal of alcohol-induced brain disease or damage (e.g., vitamin B supplements) or that treat or prevent alcohol withdrawal symptoms (e.g., sedatives, diazepam).

In some embodiments of the invention, a PPAR agonist and an additional agent are administered to an animal separately, e.g., as two separate compositions. In other embodiments a PPAR agonist and an additional agent are administered as a part of a single composition.

In some embodiments of the present invention, a PPAR agonist and an additional agent are administered to an animal under one or more of the following conditions: at different periodicities, at different durations, at different concentrations, by different administration routes, etc. In some embodiments, a PPAR agonist is administered prior to an additional agent, e.g., 0.5, 1, 2, 3, 4, 5, 10, 12, or 18 hours, 1, 2, 3, 4, 5, or 6 days, or 1, 2, 3, or 4 weeks prior to the administration of an additional agent. In some embodiments, a PPAR agonist is administered after an additional agent, e.g., 0.5, 1, 2, 3, 4, 5, 10, 12, or 18 hours, 1, 2, 3, 4, 5, or 6 days, or 1, 2, 3, or 4 weeks after the administration of an additional agent. In some embodiments, a PPAR agonist and an additional agent are administered concurrently but on different schedules, e.g., a PPAR agonist is administered daily while an additional agent is administered once a week, once every two weeks, once every three weeks, or once every four weeks. In other embodiments, a PPAR agonist is administered once a week while an additional agent is administered daily, once a week, once every two weeks, once every three weeks, or once every four weeks.

The administration of a PPAR agonist may be continued concurrently with the administration of an additional agent. Additionally, the administration of a PPAR agonist may be continued beyond the administration of an additional agent or vice versa.

In certain embodiments of the invention, the method of administering a PPAR agonist in combination with an additional agent may be repeated at least once. The method may be repeated as many times as necessary to achieve or maintain a therapeutic response, e.g., from one to about 10 times or more. With each repetition of the method the PPAR agonist and the additional agent may be the same or different from that used in the previous repetition. Additionally, the time period of administration of the PPAR agonist and the additional agent and the manner in which they are administered can vary from repetition to repetition.

The agents of the present invention may be linked to a carrier molecule to enhance the cellular uptake of the compounds. Examples of such carrier molecules include carrier peptides such as those described by Fulda et al., Nature Med. 8:808 (2002), Arnt et al., J. Biol. Chem. 277:44236 (2002), and Yang et al., Cancer Res. 63:831 (2003), fusogenic peptides (see, e.g., U.S. Pat. No. 5,965,404), and viruses and parts of viruses such as empty capsids and virus hemagglutinin (see, e.g., U.S. Pat. No. 5,547,932). Other carrier molecules include ligands for cell surface receptor such as asialoglycoprotein (which binds to the asialoglycoprotein receptor; see U.S. Pat. No. 5,166,320) and antibodies to cell surface receptors such as antibodies specific for T-cells, e.g., anti-CD4 antibodies (see U.S. Pat. No. 5,693,509).

The PPAR agonist may be administered in any appropriate manner; e.g., intraventricularly (e.g., with an intraventricular stent), intracranially, intraperitoneally, intravenously, intraarterially, nasally, or orally. In one embodiment, the PPAR agonist may be capable of crossing the blood brain barrier. In one embodiment, the agent can be conjugated with a targeting molecule, such as transferrin, for which there are receptors on the blood brain barrier. See, e.g., U.S. Pat. No. 4,902,505. In a further embodiment, the agents can be modified to have decreased polarity, or increased hydrophobicity, as more hydrophobic (less polar) agents cross the blood brain barrier more readily. See, e.g., U.S. Pat. No. 5,260,308. In a further embodiment, hydrophobic (non-polar) agents can be selected and used. In yet another embodiment, the agents can be administered in a liposome, particularly a liposome targeted to the blood brain barrier. See, e.g., U.S. Pat. No. 6,372,250. Administration of pharmaceutical agents in liposomes is known.

Compositions within the scope of this invention include all compositions wherein the agents of the present invention are contained in an amount which is effective to achieve its intended purpose. While individual needs vary, determination of optimal ranges of effective amounts of each component is within the skill of the art. The actual dosage and treatment regimen can be readily determined by the ordinary skilled physician, taking into account the route of administration, age, weight, and health of the subject, as well as the stage of brain disease, and, of course, any side effects of the agents, efficacy of the agents, and in accordance with customary medical procedures and practices. Typically, the agents may be administered to animals, e.g. humans, orally at a dose of 0.0025 to 50 mg/kg, or an equivalent amount of the pharmaceutically acceptable salt thereof, per day of the body weight of the animal being treated for brain damage or disease. Preferably, about 0.01 to about 10 mg/kg is orally administered to treat, prevent, or reverse brain damage or disease. For intramuscular injection, the dose is generally about one-half of the oral dose. For example, a suitable intramuscular dose would be about 0.0025 to about 25 mg/kg, and most preferably, from about 0.01 to about 5 mg/kg.

The unit oral dose may comprise from about 0.01 to about 50 mg, preferably about 0.1 to about 10 mg of each agent. The unit dose may be administered one or more times daily as one or more tablets or capsules each containing from about 0.1 to about 10, conveniently about 0.25 to 50 mg of the agents.

In addition to administering agents as raw chemicals, the agents of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally or topically and which can be used for the preferred type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by injection, topically or orally, contain from about 0.01 to 99 percent, preferably from about 0.25 to 75 percent of active compound(s), together with the excipient.

The pharmaceutical compositions of the invention may be administered to any subject which may experience the beneficial effects of the compounds of the invention. Foremost among such subjects are mammals, e.g., humans, although the invention is not intended to be so limited. Other animals include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal, or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The invention further provides an animal model of alcohol-induced brain damage and disease produced by chronically feeding ethanol to Long-Evans rats. Surprisingly, it has been discovered that Long-Evans rats exhibit a robust response to ethanol feeding compared to other rat strains that make the rats ideally suited for the study of the effects of chronic alcohol intake. In one embodiment, ethanol is included in the daily diet of Long-Evans rats. For example, ethanol may comprise about 0%, 2%, 4.5%, 6.5%, 9.25% (v/v) (equivalent to 0%, 8%, 18%, 26%, or 37% of the caloric content) or more of the daily diet. In one embodiment, ethanol comprises about 37% of the caloric content of the daily diet. Ethanol feeding may continue for as long as desired, e.g., from as little as two days to as long as six months or more. In one embodiment, ethanol feeding is continued until brain damage is induced, e.g., for 1, 2, 3, 4, 5, or 6 weeks or more, followed by the administration of agents or other treatments to determine their effect on the brain damage. In another embodiment, agents or treatments are administered prior to or concurrently with ethanol feeding to determine if brain damage can be prevented or slowed.

The invention further relates to a method for screening for an agent that is potentially useful for the treatment, prevention or reversal of alcohol-induced brain damage or disease, comprising administering an agent to the animal model produced by chronically feeding ethanol to Long-Evans rats and determining the level of brain damage, cognitive impairment, and/or insulin resistance relative to the level in a control animal that has not had the agent administered, wherein an improvement in the level of brain damage, cognitive impairment, and/or insulin resistance relative to the level in a control animal that has not had the agent administered indicates that the agent is potentially useful for the treatment, prevention or reversal of alcohol-induced brain damage or disease.

Agents that may be screened include proteins, polypeptides, peptides, antibodies, nucleic acids, organic molecules, natural products, chemical libraries, and the like.

The invention additionally provides a method for testing a potential treatment for treatment, prevention or reversal of alcohol-induced brain damage or disease, comprising administering the potential treatment to the animal model produced by chronically feeding ethanol to Long-Evans rats and determining the level of brain damage and/or insulin resistance relative to the level in a control animal that has not had the potential treatment administered, wherein an improvement in the level of brain damage and/or insulin resistance relative to the level in a control animal that has not had the potential treatment administered indicates that the treatment is potentially useful for the treatment, prevention or reversal of alcohol-induced brain damage or disease.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

Example 1

General Methods for Chronic Ethanol Exposure Adult Rat Model

Male (~200 g) Long Evans rats (Charles River Laboratories, Cambridge, Mass.) were fed isocaloric liquid diets (Bio-Serv, Frenchtown, N.J.) in which ethanol comprised 0% or 37% of the caloric content (9.25% v/v) for 6 weeks (Yeon et al., *Hepatology* 38:703 (2003)). A chow fed control group was also studied. Rats were monitored daily to ensure equivalent food consumption and maintenance of body weight. Upon sacrifice, the brains were harvested and either immersion fixed in Histochoice fixative (Amresco Corp., Solon, Ohio) for paraffin embedding, or sliced fresh to micro-dissect temporal cortex, hypothalamus, and cerebellum. The fresh tissue blocks were snap frozen in a dry ice-methanol bath and stored at −80° C. for mRNA and protein studies.

Histological Studies

Fixed brains were sectioned in the coronal plane along standardized landmarks and embedded in paraffin. Paraffin-embedded sections (8 μm thick) were stained with hematoxylin and eosin, or immunostained with monoclonal antibodies to 8-hydroxy-deoxyguanosine (8-OHdG) (Oxis Research) or 4-hydroxynonenol (HNE) (Chemicon International, Temecula, Calif.) to detect DNA damage and lipid peroxidation, respectively. Prior to immunostaining, deparaffinized, re-hydrated sections were treated with 0.1 mg/ml saponin in phosphate buffered saline (10 mM sodium phosphate, 0.9% NaCl, pH 7.4; PBS) for 20 minutes at room temperature, followed by 3% hydrogen peroxide in methanol for 10 minutes to quench endogenous peroxidase activity, and then 30 minutes in SuperBlock-TBS (Pierce Chemical Co., Rockford, Ill.) at room temperature to block non-specific binding sites. The sections were incubated overnight at 4° C. with 0.5-1 μg/ml of primary antibody. Immunoreactivity was detected with biotinylated secondary antibody, avidin biotin horseradish peroxidase complex (ABC) reagents, and diaminobenzidine as the chromogen (Vector Laboratories, Burlingame, Calif.) (Lam et al. *J. Biol. Chem.* 269:20648 (1994)). The tissue sections were counterstained with hematoxylin and examined by light microscopy. Negative (non-relevant antibody) and positive (glial fibrillary acidic protein) control reactions were performed in parallel. The sections were examined under code.

Real Time Quantitative Reverse Transcriptase Polymerase Chain Reaction (RT-PCR) Assays Total RNA was isolated from brain tissue using TRIzol reagent (Invitrogen, Carlsbad, Calif.) according to the manufacturer's protocol. RNA concentrations and purity were determined from the absorbances measured at 260 nm and 280 nm. RNA (2 μg) was reverse transcribed using the AMV First Strand cDNA synthesis kit (Roche Diagnostics Corporation, Indianapolis, Ind.) and random oligodeoxynucleotide primers. Real time quantitative RT-PCR was used to measure mRNA levels of insulin, IGF-I, and IGF-II growth factors, their corresponding receptors, neuronal (Hu), astrocytic (glial fibrillary acidic protein; GFAP), oligodendroglial (myelin-associated glycoprotein-1; MAG-1), microglial (AIF1), and endothelial (endothelin-1; ET-1) cell genes, acetyl cholinesterase (AChE), and choline acetyltransferase (ChAT). Ribosomal 18S RNA levels measured in parallel reactions were used to calculate relative abundance of the mRNA transcripts (Myers et al., *Trends Biochem. Sci.* 19:289 (1994); Baltensperger et al., *Science* 260:1950 (1993)). PCR amplifications were performed in 25 μl reactions containing cDNA generated from 2.5 ng of original RNA template, 300 nM each of gene specific forward and reverse primer (Table 1), and 12.5 μl of 2× QuantiTect SYBR Green PCR Mix (Qiagen Inc, Valencia, Calif.). The amplified signals were detected continuously with the BIO-RAD iCycler iQ Multi-Color RealTime PCR Detection System (Bio-Rad, Hercules, Calif.). The amplification protocol used was as follows: initial 15-minutes denaturation and enzyme activation at 95° C., 45 cycles of 95° C.×15 sec, 55°-60° C.×30 sec, and 72° C.×30 sec. Annealing temperatures were optimized using the temperature gradient program provided with the iCycler software.

TABLE 1

Primer pairs for real time quantitative RT-PCR

| Primer | Direction | Sequence (5'→3') (mRNA) | Position (bp) | Amplicon Size |
|---|---|---|---|---|
| 18S rRNA | For | GGA CAC GGA CAG GAT TGA CA (SEQ ID NO: 1) | 1278 | 50 |
| 18S rRNA | Rev | ACC CAC GGA ATC GAG AAA GA (SEQ ID NO: 2) | 1327 | |

TABLE 1-continued

Primer pairs for real time quantitative RT-PCR

| Primer | Direction | Sequence (5'→3') (mRNA) | Position | Amplicon Size (bp) |
|---|---|---|---|---|
| 28S rRNA | For | GGT AAA CGG CGG GAG TAA CTA TG (SEQ ID NO: 3) | 3712 | 107 |
| 28S rRNA | Rev | TAG GTA GGG ACA GTG GGA ATC TCG (SEQ ID NO: 4) | 3818 | |
| Insulin | For | TTC TAC ACA CCC AAG TCC CGT C (SEQ ID NO: 5) | 145 | 135 |
| Insulin | Rev | ATC CAC AAT GCC ACG CTT CTG C (SEQ ID NO: 6) | 279 | |
| Insulin Receptor | For | TGA CAA TGA GGA ATG TGG GGA C (SEQ ID NO: 7) | 875 | 129 |
| Insulin Receptor | Rev | GGG CAA ACT TTC TGA CAA TGA CTG (SEQ ID NO: 8) | 1003 | |
| IGF-I | For | GAC CAA GGG GCT TTT ACT TCA AC (SEQ ID NO: 9) | 65 | 127 |
| IGF-I | Rev | TTT GTA GGC TTC AGC GGA GCA C (SEQ ID NO: 10) | 191 | |
| IGF-I Receptor | For | GAA GTC TGC GGT GGT GAT AAA GG (SEQ ID NO: 11) | 2138 | 113 |
| IGF-I Receptor | Rev | TCT GGG CAC AAA GAT GGA GTT G (SEQ ID NO: 12) | 2250 | |
| IGF-II | For | CCA AGA AGA AAG GAA GGG GAC C (SEQ ID NO: 13) | 763 | 95 |
| IGF-II | Rev | GGC GGC TAT TGT TGT TCA CAG C (SEQ ID NO: 14) | 857 | |
| IGF-II Receptor | For | TTG CTA TTG ACC TTA GTC CCT TGG (SEQ ID NO: 15) | 1066 | 91 |
| IGF-II Receptor | Rev | AGA GTG AGA CCT TTG TGT CCC CAC (SEQ ID NO: 16) | 1156 | |
| AChE | For | TTC TCC CAC ACC TGT CCT CAT C (SEQ ID NO: 17) | 420 | 123 |
| AChE | Rev | TTC ATA GAT ACC AAC ACG GTT CCC (SEQ ID NO: 18) | 542 | |
| ChAT | For | TCA CAG ATG CGT TTC ACA ACT ACC (SEQ ID NO: 19) | 478 | 106 |
| ChAT | Rev | TGG GAC ACA ACA GCA ACC TTG (SEQ ID NO: 20) | 583 | |
| Hu | For | CAC TGT GTG AGG GTC CAT CTT CTG (SEQ ID NO: 21) | 271 | 50 |
| Hu | Rev | TCA AGC CAT TCC ACT CCA TCT G (SEQ ID NO: 22) | 320 | |
| GFAP | For | TGG TAA AGA CGG TGG AGA TGC G (SEQ ID NO: 23) | 1245 | 200 |
| GFAP | Rev | GGC ACT AAA ACA GAA GCA AGG GG (SEQ ID NO: 24) | 1444 | |
| MAG-1 | For | AAC CTT CTG TAT CAG TGC TCC TCG (SEQ ID NO: 25) | 18 | 63 |
| MAG-1 | Rev | CAG TCA ACC AAG TCT CTT CCG TG (SEQ ID NO: 26) | 80 | |
| ET-1 | For | TTC CAA GAG AGG TTG AGG TGT TCC (SEQ ID NO: 27) | 957 | 83 |
| ET-1 | Rev | CAG CAA GAA GAG GCA AGA GAA TCA C (SEQ ID NO: 28) | 1039 | |
| AIF-1 | For | GGA TGG GAT CAA CAA GCA CT (SEQ ID NO: 29) | 168 | 158 |
| AIF-1 | Rev | GTT TCT CCA GCA TTC GCT TC (SEQ ID NO: 30) | 325 | |

In preliminary studies, SYBR Green-labeled PCR products were evaluated by agarose gel electrophoresis, and the authenticity of each amplicon was verified by nucleic acid sequencing. The complementary (c) DNAs were cloned into the PCRII vector (Invitrogen, Carlsbad, Calif.). Serial dilutions of known quantities of recombinant plasmid DNA containing the specific target sequences were used as standards in the PCR reactions, and the regression lines generated from the $C_t$ values of the standards were used to calculate mRNA abundance. Relative mRNA abundance was determined from the ng ratios of specific mRNA to 18S measured in the same samples. Results were normalized to 18S because 18S is highly abundant and the levels were essentially invariant among the samples, whereas housekeeping genes were modulated with disease state. Inter-group statistical comparisons were made using the calculated mRNA/18S ratios. Control studies included real-time quantitative PCR analysis of: 1) template-free reactions; 2) RNA that had not been reverse transcribed; 3) RNA samples that were pre-treated with DNAse I; 4) samples treated with RNAse A prior to reverse transcriptase reaction; and 5) genomic DNA.

Receptor Binding Assays

Fresh frozen tissue (~100 mg) was homogenized in 5 volumes of NP-40 lysis buffer (50 mM Tris-HCl, pH 7.5, 1% NP-40, 150 mM NaCl, 1 mM EDTA, 2 mM EGTA) containing protease inhibitors (1 mM PMSF, 0.1 mM TPCK, 1 μg/ml aprotinin, 1 μg/ml pepstatin A, 0.5 μg/ml leupeptin, 1 mM NaF, 1 mM $Na_4P_2O_7$). Protein concentrations were determined using the bicinchoninic acid (BCA) assay (Pierce, Rockford, Ill.). Exploratory studies determined the amounts of protein and concentrations of radiolabeled ligand required to achieve 20% specific binding. Insulin receptor binding assays were performed using 100 μg protein. IGF-I binding assays required 25 μg protein per sample, and IGF-II receptor binding assays were optimized using 10 μg protein. Competitive equilibrium binding assays were used to assess growth factor binding in relation to ethanol exposure. For total binding, duplicate individual protein samples were incubated in 100 μl reactions containing binding buffer (100 mM HEPES, pH 8.0, 118 mM NaCl, 1.2 mM $MgSO_4$, 8.8 mM dextrose, 5 mM KCl, 1% bovine serum albumin) and 100 nCi/ml of [$^{125}$I] (2000 Ci/mmol; 50 μM) insulin, IGF-I, or IGF-II. To measure non-specific binding, replicate samples were identically prepared but with the addition of 0.1 μM unlabeled (cold) ligand.

All reactions were performed in 1.5 ml Eppendorff tubes, and the incubations were performed at 4° C. for 16 hours with gentle platform agitation. Bound radiolabeled tracer was then precipitated by adding 500 μl of 0.15% bovine gamma globulin (prepared in 100 mM Tris-HCl, pH 8.0) followed by 400 μl 37.5% polyethylene glycol 8000 (PEG-8000; prepared in 100 mM Tris-HCl, pH 8.0) to each tube. The samples were thoroughly mixed by vortexing, and then incubated on ice for at least 2 hours. The precipitates were collected by centrifuging the samples at 15,000×g for 5 minutes at room temperature. The supernatant fraction, which contained unbound (free) ligand, was transferred in its entirety to a Gamma counting tube (Sarstedt, Newton, N.C.). The Eppendorff tube tip containing the pellet was cut and released directly into a separate Gamma counting tube. The samples were counted for 1 minute in an LKB CompuGamma CS Gamma counter. Specific binding was calculated by subtracting fmol of non-specific binding, i.e., amount bound in the presence of cold ligand, from the total fmol bound (absence of unlabeled competitive ligand). The results were analyzed and plotted using the GraphPad Prism 4 software (GraphPad Software, Inc., San Diego, Calif.).

Source of Reagents

Human recombinant [$^{125}$I] Insulin, IGF-I, and IGF-II were purchased from Amersham Biosciences (Piscataway, N.J.). Unlabeled human insulin was purchased from Sigma-Aldrich (St. Louis, Mo.). Recombinant IGF-I and IGF-II were obtained from Bachem (King of Prussia, Pa.). Monoclonal antibodies to 8-OHdG and HNE were purchased from Oxis Scientific (Foster City, Calif.). All other fine chemicals and reagents were purchased from CalBiochem (Carlsbad, Calif.) or Sigma-Aldrich (St. Louis, Mo.).

Statistical Analysis

Experiments were conducted using 9 rats per group. Data are depicted as means±S.E.M. in the graphs. Inter-group comparisons were made using Student T-tests. Statistical analyses were performed using the Number Cruncher Statistical System (Kaysville, Utah). P-values corresponding to significant differences and trends are indicated over the graphs.

Example 2

Chronic Ethanol Consumption Causes Neurodegeneration in Adult Rat Brains

The histopathological studies were focused on the cerebellum and temporal lobe, including hippocampus because these structures represent known targets of ethanol-mediated neurotoxicity and they were evaluated using molecular and biochemical approaches. Hematoxylin and eosin stained sections of brain demonstrated structural abnormalities in the cerebellar cortex of ethanol-fed rats, including loss of Purkinje cells and reduced densities of cells within the internal granule layer (FIGS. 1A-1D). In contrast, the temporal lobes and hippocampi lacked distinct histopathological abnormalities including overt evidence of cell loss.

Immunohistochemical staining of adjacent sections revealed conspicuously increased cellular labeling for HNE, and to a lesser extent, 8-OHdG in brains of ethanol-fed rats. In cerebella of ethanol-exposed rats, increased HNE immunoreactivity, which reflects lipid peroxidation, was mainly localized in the Purkinje and granule cell layers (FIGS. 1E-1F), but it was also detected in subcortical white matter glia. In contrast, 8-OHdG immunoreactivity was detected in scattered cells within the Purkinje and granule layers of the cerebellum of ethanol fed rats (FIGS. 1G-1H). In the ethanol-fed rats, prominently increased HNE immunoreactivity was observed in the hippocampus and temporal cortex (FIGS. 2A-2F). Increased HNE immunoreactivity was detected in the nucleus and cytoplasm of neurons distributed throughout the dentate gyrus (FIGS. 2A-2B) and Ammon's horn (FIGS. 2C-2D) of the hippocampus, and throughout the full thickness of the temporal cortex (FIGS. 2E-2F). Increased HNE immunoreactivity was mainly distributed in neurons (based on location, size (10-16 micron diameter), and their pyramidal shape), although other cell types including glia and endothelial cells distributed in both gray and white matter structures were also HNE-positive. In contrast to HNE, increased 8-OHdG immunoreactivity, which reflects DNA damage, was only detected in scattered cells within the cerebellar granule layer (FIGS. 1G-1H), and in the temporal cortex (FIGS. 2G-2H). The distribution of increased 8-OHdG immunoreactivity overlapped with that of HNE in adjacent sections, indicating that ethanol-mediated DNA damage occurred in neurons as well as other cell types within the brain.

In adult human chronic alcoholics, CNS degeneration is characterized by cerebellar atrophy, cerebral white matter atrophy, and either loss or impaired function of neurons within the hypothalamus, thalamus, hippocampus, and frontal cortex. These abnormalities are associated with variable degrees of cognitive and motor deficits, and in severe cases, dementia. In the present experimental model of chronic ethanol feeding, CNS neurodegeneration was manifested by overt cell loss in the cerebellar cortex, but not in the hypothalamus or hippocampus/temporal lobe. However, the finding of increased immunoreactivity for HNE and 8-OHdG in all three structures indicates that chronic ethanol feeding causes lipid peroxidation and DNA damage, which may not be accompanied by overt cell loss. This suggests that chronic ethanol exposure in adults can impair neuronal function due to increased induced oxidative stress. In addition, ethanol-mediated chronic oxidative stress may render CNS neurons more vulnerable to "second hits" such as hypoxia or ischemia which, in the otherwise normal brain would not necessarily cause permanent injury or neurodegeneration.

Example 3

Ethanol-Induced Pathological Shifts in Cell Type

To determine if the chronic ethanol feeding caused pathological shifts in the cell populations within the temporal cortex, hypothalamus, and cerebellum, real time quantitative RT-PCR studies were used to measure mRNA transcripts encoding Hu neuronal ribosomal RNA binding protein (Datta et al., *Cell* 91:231 (1997); Hetman et al., *J. Neurosci.* 20:2567 (2000); Dudek et al., *Science* 275:661 (1997)), myelin-associated glycoprotein-1 (MAG-1) for oligodendroglia, glial fibrillary acidic protein (GFAP) for astrocytes, and endothelin-1 (ET-1) for endothelial cells. The ng quantities of each specific mRNA transcript detected were normalized to the 18S RNA levels measured in the same samples, and results from 9 animals per group were analyzed statistically. The studies demonstrated ethanol-associated reductions in Hu gene expression in the temporal lobe (FIG. 3A) and cerebellum (FIG. 3C), but not in the hypothalamus (FIG. 3B). MAG-1 expression was significantly reduced in the hypothalamus, but not in the temporal lobe or cerebellum of ethanol-fed rats (FIGS. 3D-3F). Significantly increased GFAP expression was detected in the cerebellum, but not in the temporal lobe or hypothalamus of ethanol-fed rats (FIGS. 3G-3I). ET-1 expression was significantly increased in the temporal lobe, but not in the hypothalamus or cerebellum of ethanol-fed rats (FIGS. 3J-3L).

In the ethanol-fed rats, histopathological and/or immunohistochemical indices of neurodegeneration were associated with pathological shifts in brain cell populations within each of the regions examined. The present studies utilized a novel approach for estimating the proportions of neurons, oligodendroglia, astrocytes, and endothelial cells by comparing the relative mRNA expression levels of Hu, MAG-1, GFAP, and ET-1, respectively, in the same tissue samples.

Although each of the brain regions studied represents a known target of ethanol neurotoxicity, the adverse effects of ethanol were inhomogeneous with respect to cell loss. In the temporal cortex, chronic ethanol exposure resulted in loss of neurons (decreased Hu gene expression) and relatively increased endothelial cell populations. In the hypothalamus, oligodendroglial cells were relatively reduced. In the cerebellum, neuronal loss, which was evident in histological sections, was accompanied by increased populations of astrocytes. Therefore, in adults, chronic ethanol exposure has differential effects in terms of neurotoxicity and cell loss within different brain regions. Importantly, the findings, together with the observed increases in HNE and 8-OHdG immunoreactivity in the same structures, suggest that the cerebellum and temporal lobe are highly vulnerable targets of ethanol-mediated neuronal toxicity. These adverse effects of ethanol could account for the progressive cognitive and motor deficits that occur in chronic alcoholics.

Example 4

Figures 4A, 4B, 4C, 4D, 4E, 4F, 4G, 4H, 4I:
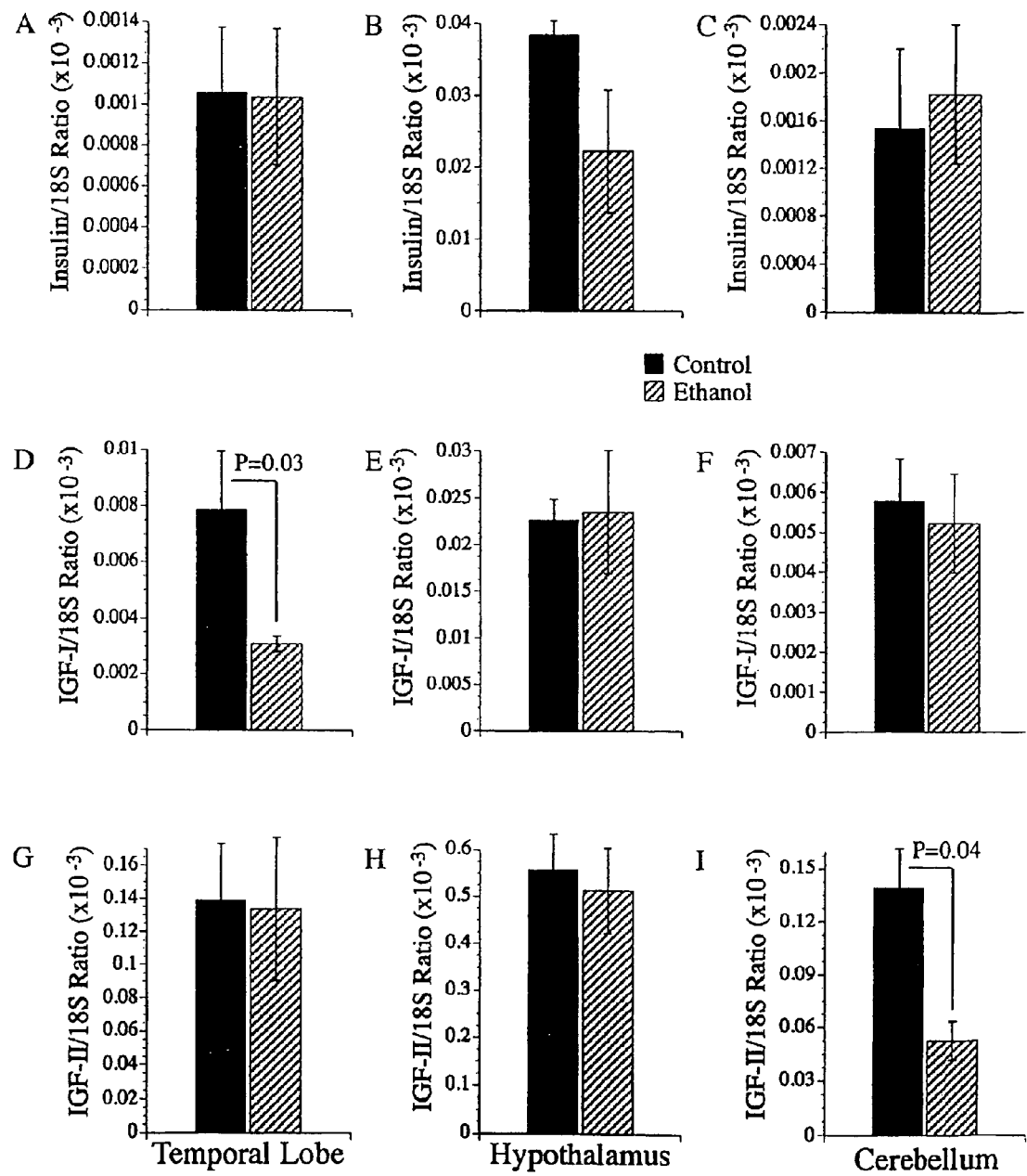

Effects of Ethanol on mRNA Expression of Insulin, IGF-I, and IGF-II Polypeptides, and the Insulin, IGF-I, and IGF-II Receptors Real time quantitative RT-PCR studies detected mRNA transcripts corresponding to insulin, IGF-I, and IGF-II polypeptides, and insulin, IGF-I, and IGF-II receptors in both control and ethanol exposed brains (FIGS. 4 and 5). The insulin gene was most abundantly expressed in the hypothalamus where the levels were 20- to 40-fold higher than in the temporal lobe and cerebellum (FIGS. 4A-4C). The IGF-I gene was also most abundantly expressed in the hypothalamus, but the mean levels were 3- to 4-fold higher than in the temporal lobe and cerebellum (FIGS. 4D-4F). Overall, IGF-II was more abundantly expressed than insulin and IGF-I, and again, the highest expression was in the hypothalamus (FIGS. 4G-4I). Chronic ethanol feeding significantly reduced the mean levels of IGF-I expression in the temporal lobe (FIG. 4D), and IGF-II expression in the cerebellum (FIG. 4I). Otherwise, chronic ethanol feeding had no significant effect on insulin, IGF-I, or IGF-II expression in the brain.

Figures 5A, 5B, 5C, 5D, 5E, 5F, 5G, 5H, 5I:
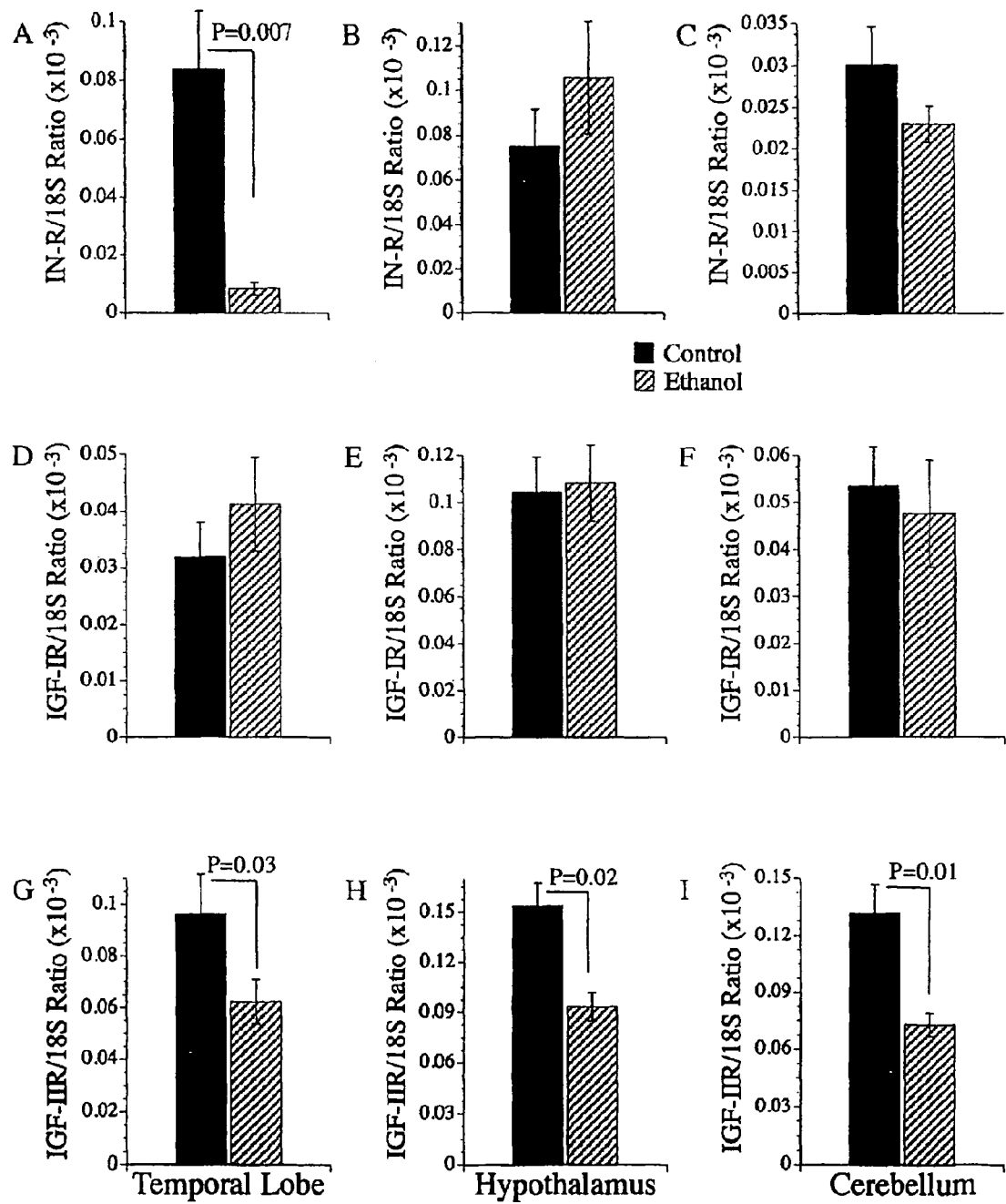

The mean expression levels of the insulin receptor gene were similar in the temporal lobe and hypothalamus, and both were 2.5- to 3-fold higher than in the cerebellum (FIGS. 5A-5C). IGF-I receptor expression was highest in the hypothalamus, followed by the cerebellum, and then the temporal lobe (FIGS. 5D-5F). In contrast, the mean levels of IGF-II receptor mRNA were similar in the temporal lobe, hypothalamus, and cerebellum (FIGS. 5G-5I). Chronic ethanol feeding significantly reduced insulin receptor gene expression in the temporal lobe (FIG. 5A), and IGF-II receptor expression in the temporal lobe, hypothalamus, and cerebellum (FIGS. 5G-5I). Otherwise, the chronic ethanol exposure did not significantly alter the expression of insulin or IGF-I receptors in the brain.

Real time quantitative RT-PCR studies demonstrated mRNA transcripts corresponding to insulin, IGF-I, IGF-II, and their corresponding receptors in the cerebellum, temporal lobe, and hypothalamus, indicating that the genes required of insulin and IGF signaling are expressed in adult brains. Importantly, insulin and IGF polypeptide genes were all expressed at much higher levels in the hypothalamus than in the cerebellum or temporal lobe, suggesting that the hypothalamus is a major source of these growth factors within the CNS. However, chronic ethanol feeding significantly reduced IGF-I mRNA expression in the temporal lobe, and IGF-II expression in the cerebellum. Since neuronal loss with reduced expression of Hu was evident in these structures and not in the hypothalamus, the results suggest that the relative withdrawal of these growth factors may have contributed to the region-specific loss of neurons observed in ethanol-exposed brains.

Although IGF-II signaling mechanisms have not been thoroughly investigated in the CNS, recent studies in other tissues and cell types demonstrated that IGF-II can mediate cell survival by interacting with its own receptor and activating PI3 kinase-Akt via G-coupled protein signaling. Alternatively, IGF-II can bind to insulin and IGF-I receptors, and activate growth and survival signaling pathways through insulin receptor substrate-dependent mechanisms. Therefore, ethanol-mediated reductions in IGF-II expression in the cerebellum could have broad adverse effects on survival and function of neurons that mediate important motor functions such as gait and postural stability and coordinated motor activity.

Insulin and IGF-I receptors were more abundantly expressed in the hypothalamus than in the temporal lobe and cerebellum, whereas IGF-II receptors were similarly expressed in these three structures. The major effects of chronic ethanol exposure were to reduce the levels of IGF-II receptor expression in all three brain regions, and insulin receptor expression in the temporal lobe. The reduced levels of insulin and IGF-II receptor expression could reflect loss of cells that bear these receptors. Loss of insulin receptor-expressing cells in the brain could contribute to insulin resistance and result in decreased expression of insulin-responsive genes. Loss of IGF-II receptor-expressing cells could adversely affect neuronal survival and plasticity, since signaling through the IGF-II receptor can activate PI3 kinase-Akt via G-coupled protein signaling. The PI3 kinase-Akt pathway has a critical role in stimulating neuronal survival and neurite outgrowth which is required for plasticity.

Example 5

Ethanol Impairs Insulin and IGF Receptor Binding

Figures 6A, 6B, 6C, 6D, 6E, 6F, 6G, 6H, 6I:
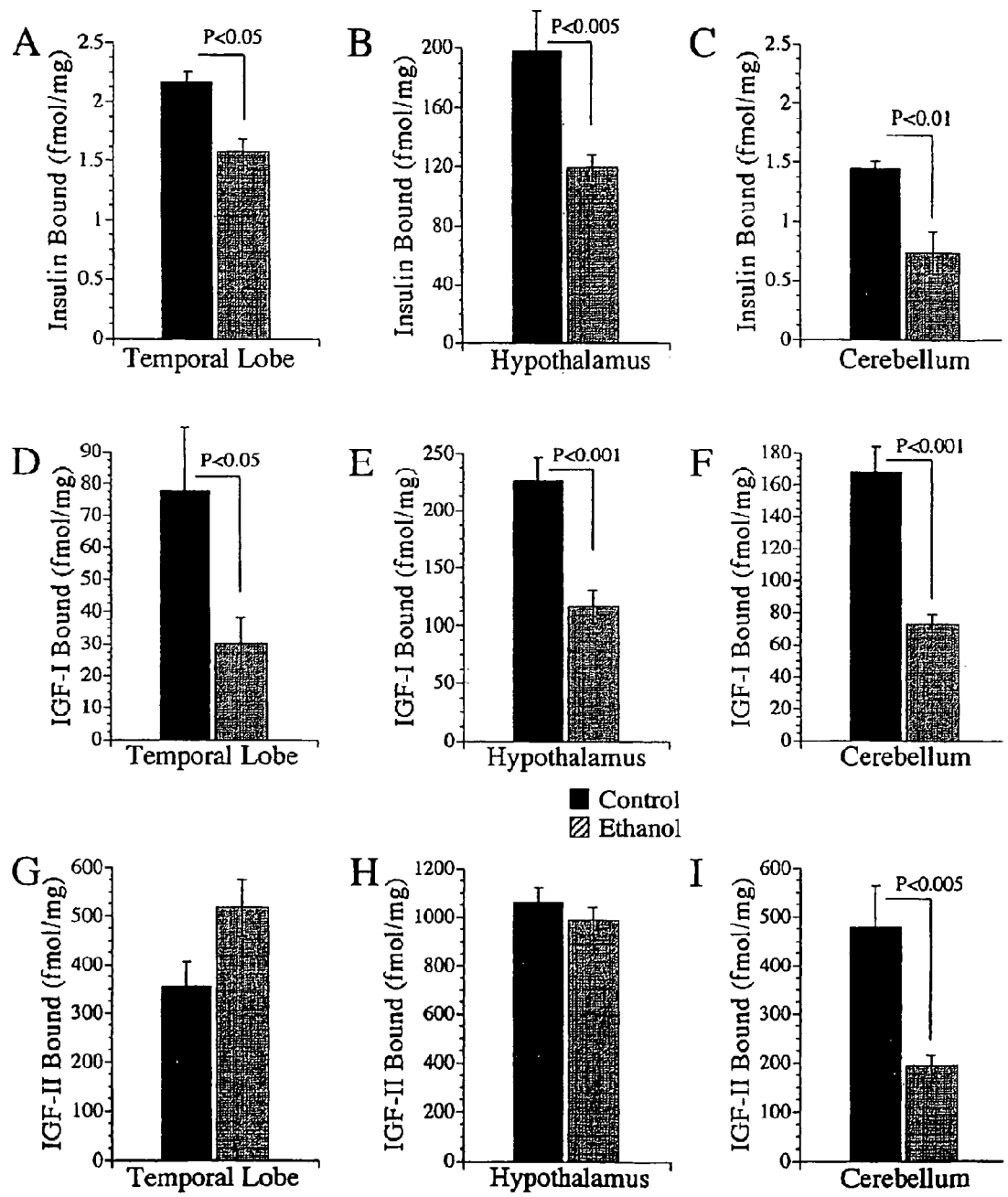

Given the variability in effects of chronic ethanol feeding on growth factor and growth factor receptor expression, it was of interest to determine if ethanol could impair insulin/IGF signaling through another mechanism. Effective ligand binding is critical to the insulin and IGF signaling cascades, and many of the downstream effects of impaired insulin signaling that have been reported in ethanol-exposed brains, including reduced neuronal survival, could be mediated by reduced insulin or IGF-I binding in the CNS. Equilibrium binding assays were performed by incubating temporal cortex, hypothalamus, and cerebellar membrane protein extracts with [$^{125}$I]-labeled insulin, IGF-I, or IGF-II as tracer, in the presence or absence of excess cold ligand. Those studies demonstrated higher levels of insulin, IGF-I and IGF-II receptor binding (fmol/mg) in the hypothalamus than in the temporal cortex and cerebellum (FIG. 6). Chronic ethanol feeding resulted in significantly reduced insulin and IGF-I receptor binding in the temporal lobe, hypothalamus, and cerebellum (FIGS. 6A-6F). In addition, IGF-II receptor binding was significantly lower in cerebella of ethanol-exposed relative to control rats (FIG. 6I), whereas in the temporal lobe and hypothalamus, IGF-II receptor binding was relatively preserved in the ethanol-exposed group (FIGS. 6G-6H).

Effective ligand binding is critical to the signaling cascade, and many of the previously reported downstream adverse effects of ethanol on insulin signaling including reduced neuronal survival could be mediated by impaired insulin or IGF-I binding in the CNS. Equilibrium binding assays demonstrated that the highest levels of insulin, IGF-I, and IGF-II receptor binding were in the hypothalamus, corresponding with the highly abundant expression levels of these receptors. Chronic ethanol exposure prominently reduced the levels of insulin and IGF-I receptor binding in the temporal lobe, hypothalamus, and cerebellum, and IGF-II receptor binding in the cerebellum. This suggests that chronic ethanol exposure inhibits insulin and IGF-I signaling mechanisms in various regions of the adult brain. Importantly, the inhibition of insulin, IGF-I, and IGF-II receptor binding in the cerebellum was associated with histopathological evidence of neuronal loss, whereas in the other two regions, the tissue architecture was relatively preserved despite evidence of chronic oxidative injury.

The relative preservation of IGF-II receptor binding, vis-à-vis reduced expression of the IGF-II receptors in the temporal lobe and hypothalamus indicates that compensatory mechanisms may have developed to preserve the function IGF-II signaling. These results are similar to those obtained for the experimental FAS model in that, chronic gestational exposure to ethanol impaired insulin and IGF-I receptor binding to greater extents than IGF-II receptor binding vis-à-vis modest reduction in receptor mRNA expression (see below). Importantly, the findings herein and from previous studies suggest that ethanol inhibition of insulin and IGF signaling as required for cell survival and energy metabolism, is mediated at the level of receptor binding, i.e., the most proximal point within the signal transduction cascade. Moreover, the aggregate results highlight the potential importance of IGF-II signaling pathways as mediators of neuronal survival and function in both developing and mature brains, particularly in the context of sustained oxidative stress and insulin/IGF-I resistance.

Example 6

Ethanol-Mediated Impairments in Acetylcholine Homeostasis

Figure 7A:
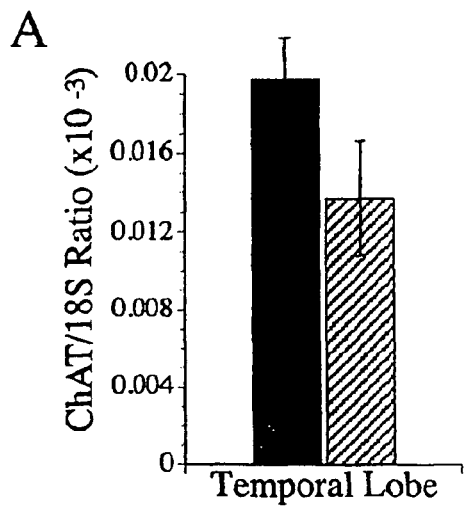
Figure 7B:
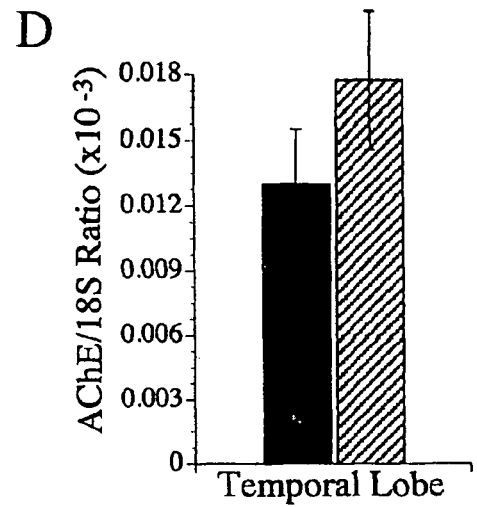
Figure 7C:
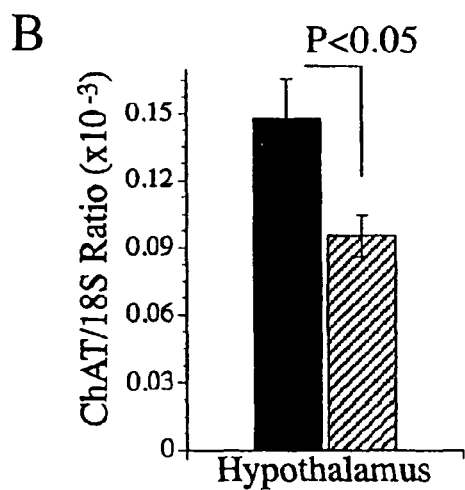
Figure 7D:
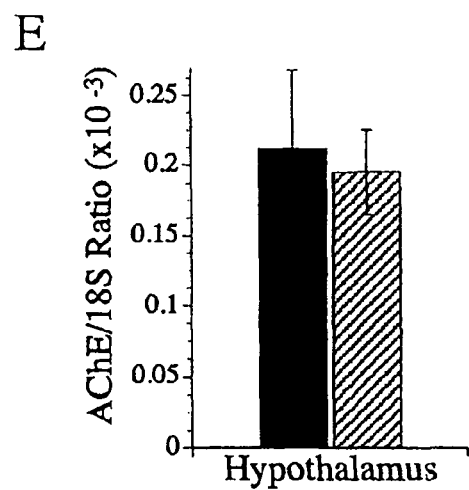
Figure 7E:
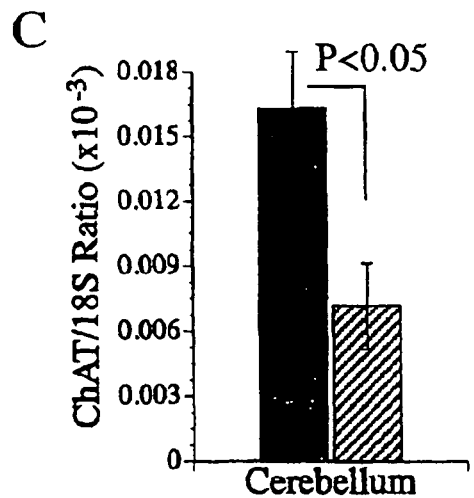
Figure 7F:
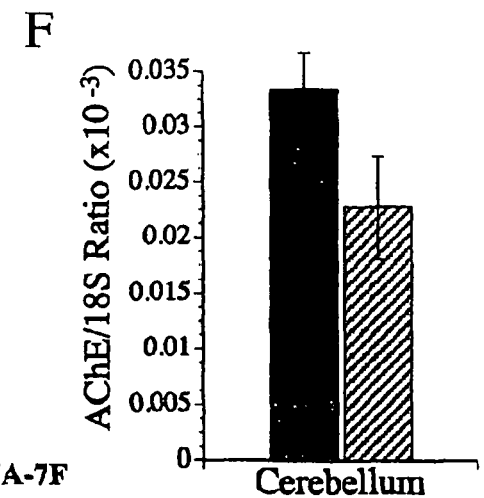

Acetylcholine has major functional roles in CNS cognitive and motor systems. Acetylcholine production requires adequate supplies of choline and acetyl-Co-A. Acetyl-Co-A is generated by energy metabolism, which in turn is driven by insulin and IGF-I stimulation. Recent studies demonstrated that choline acetyltransferase (ChAT) expression is regulated by insulin and IGF-I stimulation (Minana et al. *J. Neurochem.* 75:954 (2000)). Therefore, it was of interest to determine if ethanol inhibition of insulin and IGF-I signaling mechanisms were associated with deficits in ChAT. Since the steady-state levels of acetylcholine are negatively regulated by acetyl cholinesterase (AChE), it was also of interest to measure AChE mRNA levels. Real time quantitative RT-PCR studies demonstrated significantly reduced mean levels of ChAT mRNA expression in hypothalamus (FIG. 7B) and cerebellum (FIG. 7C), but not in the temporal lobe (FIG. 7A). In contrast, chronic ethanol feeding did not significantly alter the expression of AChE in any of the three brain regions examined (FIGS. 7D-7F).

Since ChAT expression is regulated by insulin and IGF-I stimulation, and acetylcholine is a major neurotransmitter that mediates CNS cognitive and motor functions, it was of interest to determine if the inhibitory effects of ethanol on insulin and IGF signaling impaired acetylcholine homeostasis in the adult brain. The real time quantitative RT-PCR studies demonstrated reduced ChAT expression in ethanol-exposed relative to control hypothalamus and cerebellum. ChAT expression was also reduced in ethanol-exposed temporal lobes, but the difference from control did not reach statistical significance. These results correspond with the finding of broadly impaired insulin and IGF-I receptor binding in brains ethanol-fed rats. Reductions in ChAT expression could result in deficits in acetylcholine biosynthesis, and without compensatory reductions in AChE expression, acetylcholine homeostasis would be adversely perturbed.

The aggregate results demonstrate that chronic ethanol consumption causes neurodegeneration characterized by neuronal loss, impaired neuronal function, and increased oxidative stress/lipid peroxidation in the adult brain. Neuronal oxidative stress was more pronounced than cell loss, suggesting that many of the remaining neurons in the brain, although histologically intact, had major deficits in function as demonstrated by the significantly reduced levels of ChAT gene expression. The deficits in acetylcholine homeostasis produced by chronic ethanol exposure could impair cognitive and motor functions and thereby contribute to the CNS impairments commonly observed in chronic alcoholics. The results of these studies suggest that ethanol-induced neuronal loss and neurodegeneration is mediated by two distinct but overlapping mechanisms: 1) insulin/IGF-I resistance, which is mainly effectuated by impaired receptor binding; and 2) increased oxidative stress mediated by lipid peroxidation and DNA damage. Recently, ethanol impaired binding to the insulin and IGF-I receptors was linked to cholesterol depletion from the cell membranes and attendant reduced activation of the corresponding receptor tyrosine kinases (Soscia et al., *Cell. Mol. Life Sci.*, in press (2006)). It is noteworthy that nearly identical mediators of neuronal loss and impaired neuronal function were identified in association with cerebellar hypoplasia in experimental models of FAS (see below) and Alzheimer-type neurodegeneration, and in human brains with Alzheimer's disease.

Example 7

General Methods for Chronic Ethanol Exposure in Humans

Human postmortem banked brain tissue from controls and chronic alcoholics were obtained from the Tissue Resource Center at the University of Sydney in Australia. All cases had documented evidence of chronic ethanol abuse and no evidence of other substance abuse. Control subjects were matched for age and gender and had documented low levels of ethanol consumption. Two brain regions were studied: the cerebellar cortex (anterior superior vermis region) and the anterior cingulate gyrus in the frontal lobe. These regions were selected for study because they represent major targets of ethanol neurotoxicity. Formalin fixed paraffin-embedded sections of these regions were stained with hematoxylin and eosin dyes and examined by light microscopy. Adjacent histological sections were subjected to immunohistochemical staining. Fresh, snap-frozen blocks of tissue from the same regions were used to measure mRNA expression and receptor binding.

Histological studies, RT-PCR assays, and receptor binding assays were performed as described in Example 1. The PCR primers for detecting human genes are listed in Table 2.

TABLE 2

| Primer | Sequence (5'-->3') | Position (mRNA) | Amplicon size (bp) |
|---|---|---|---|
| Insulin | TTC TAC ACA CCC AAG TCC CGT C (SEQ ID NO: 31) | 189 | 134 |
| | ATC CAC AAT GCC AGC CTT CGT C (SEQ ID NO: 32) | 322 | |
| Insulin Receptor | GGT AGA AAC CAT TAC TGG CTT CCT C (SEQ ID NO: 33) | 1037 | 125 |
| | CGT AGA GAG TGT AGT TCC CAT CCA C (SEQ ID NO: 34) | 1161 | |
| IGF-I | CAC TTC TTT CTA CAC AAC TCG GGC (SEQ ID NO: 35) | 1032 | 147 |
| | CGA CTT GCT GCT GCT TTT GAG (SEQ ID NO: 36) | 1178 | |
| IGF-I Receptor | AGG GCG TAG TTG TAG AAG AGT TTC C (SEQ ID NO: 37) | 395 | 101 |
| | TAC TTG CTG CTG TTC CGA GTG G (SEQ ID NO: 38) | 295 | |
| IGF-II | CTG ATT GCT CTA CCC ACC CAA G (SEQ ID NO: 39) | 996 | 76 |
| | TTG CTC ACT TCC GAT TGC TGG C (SEQ ID NO: 40) | 1071 | |
| IGF-II Receptor | CAC GAC TTG AAG ACA CGC ACT TAT C (SEQ ID NO: 41) | 403 | 132 |
| | GCT GCT CTG GAC TCT GTG ATT TG (SEQ ID NO: 42) | 534 | |
| IRS-I | TGC TGG GGG TTT GGA GAA TG (SEQ ID NO: 43) | 3559 | 68 |
| | GGC ACT GTT TGA AGT CCT TGA CC (SEQ ID NO: 44) | 3626 | |

TABLE 2-continued

| Primer | Sequence (5'-->3') | Position (mRNA) | Amplicon size (bp) |
|---|---|---|---|
| IIRS-2 | AAA ATT GGC GGA GCA AGG C (SEQ ID NO: 45) | 753 | 64 |
| | ATG TTC AGG CAG CAG TCG AGA G (SEQ ID NO: 46) | 816 | |
| IRS-4 | CCG ACA CCT CAT TGC TCT TTT C (SEQ ID NO: 47) | 570 | 74 |
| | TTT CCT GCT CCG ACT CGT TCT C (SEQ ID NO: 48) | 643 | |
| 18S | GGA CAC GGA CAG GAT TGA CA (SEQ ID NO: 49) | 1278 | 50 |
| | ACC CAC GGA ATC GAG AAA GA (SEQ ID NO: 50) | 1327 | |
| 28S | GGT AAA CGG CGG GAG TAA CTA TG (SEQ ID NO: 51) | 3712 | 107 |
| | TAG GTA GGG ACA GTG GGA ATC TCG (SEQ ID NO: 52) | 3818 | |

Example 8

Chronic Ethanol Consumption Causes Neurodegeneration in Adult Brains

Hematoxylin and eosin stained sections demonstrated structural abnormalities in the cerebellar cortex of the chronic alcoholics. The abnormalities included patchy loss of Purkinje cells, reduced cell densities within the internal granule layer, and proliferation of Bergmann's glia. In contrast, the cingulate gyrus lacked distinct histopathological abnormalities including overt evidence of cell loss in the alcoholics. Immunohistochemical staining of adjacent sections revealed conspicuously increased cellular labeling for GFAP and HNE, and focally increased immunoreactivity for 8-OHdG in the alcoholics. In alcoholic cerebella, increased GFAP immunoreactivity was detected in the granule layer and in the white matter cores underlying the cortex, and increased HNE immunoreactivity, which reflects lipid peroxidation, was localized in the Purkinje and granule cell layers of cortex, and in subcortical white matter. In contrast, 8-OHdG immunoreactivity was detected in scattered cells within the Purkinje and granule layers of the cerebellar cortex and in the subcortical white matter in alcoholics.

In the anterior cingulate gyrus, despite the absence of overt cell loss, prominently increased GFAP and HNE immunoreactivity were observed in both the cortex and subcortical white matter. HNE immunoreactivity was detected in the nucleus and cytoplasm of neurons (based on location, size (10-16 micron diameter), and their pyramidal shape), although other cell types including glia and vascular endothelial cells distributed in both gray and white matter structures were also HNE-positive. In contrast to HNE, increased 8-OHdG immunoreactivity, which reflects DNA damage, was only detected in scattered cells within the cortex and white matter. The distribution of increased 8-OHdG immunoreactivity overlapped with that of HNE in adjacent sections, indicating that ethanol-mediated DNA damage occurred in neurons as well as other cell types within the brain.

In adult human chronic alcoholics, CNS degeneration is characterized by cerebellar atrophy, cerebral white matter atrophy, and either loss or impaired function of neurons within the hypothalamus, thalamus, hippocampus, and frontal cortex. These abnormalities are associated with variable degrees of cognitive and motor deficits, and in severe cases, dementia. In experimental models of chronic ethanol feeding, CNS neurodegeneration was associated with overt cell loss with increased immunoreactivity for HNE and 8-OHdG in the cerebellar cortex (Soscia et al., *Cell. Mol. Life Sci.*, in press (2006)). In the present study, histopathological evidence of neuronal loss and gliosis in the cerebellar cortex of chronic alcoholics was detected, and these changes were associated with increased immunoreactivity for HNE and 8-OHdG, reflecting increased lipid peroxidation and DNA damage. The finding of increased GFAP (gliosis), HNE, and 8-OHdG immunoreactivity in the cingulate gyrus of alcoholic brains was of interest because that region did not exhibit overt evidence of neurodegeneration by routine histopathological examination. This suggests that chronic alcohol abuse causes chronic oxidative stress mediated by lipid peroxidation and DNA damage, which could impair neuronal function prior to the onset of neurodegeneration. In addition, ethanol-mediated chronic oxidative stress may render CNS neurons more vulnerable to "second hits" such as hypoxia or ischemia which, in the otherwise normal brain would not necessarily cause permanent injury or neurodegeneration.

Example 9

Ethanol-Induced Pathological Shifts in Cell Type

To determine if the chronic alcohol abuse caused pathological shifts in the cell populations within the cingulate gyrus and cerebellar vermis, real time quantitative RT-PCR was used to measure mRNA transcripts encoding Hu neuronal ribosomal RNA binding protein (Datta et al. *Cell* 91:231 (1997); Hetman et al. *J. Neurosci.* 20:2567 (2000); Dudek et al., *Science* 275:661 (1997)), myelin-associated glycoprotein-1 (MAG-1) for oligodendroglia, glial fibrillary acidic protein (GFAP) for astrocytes, endothelin-1 (ET-1) for endothelial cells, and allograft inhibitory factor-1 (AIF-1) for microglia. The ng quantities of each specific mRNA transcript detected were normalized to the 18S RNA levels measured in the same samples, and results from 9 animals per group were analyzed statistically. The studies demonstrated ethanol-associated reductions in Hu gene expression in the cerebellum, but not in the cingulate gyrus, and significantly increased GFAP expression in both the cingulate and vermis. ET-1 expression was significantly reduced in the cingulate and increased in the cerebellum. In contrast, there were no significant changes in the mean levels of MAG-1, AIF-1 or 18S rRNA associated with chronic alcohol abuse.

In the alcoholic brains, histopathological and/or immunohistochemical indices of neurodegeneration were associated with pathological shifts in brain cell populations within the cingulate gyrus and cerebellar vermis. This study utilized a novel approach for estimating the proportions of neurons, oligodendroglia, astrocytes, endothelial cells, and microglia by comparing the relative mRNA expression levels of Hu, MAG-1, GFAP, ET-1, and AIF-1 respectively in the same tissue samples.

Although both brain regions studied represent known targets of ethanol neurotoxicity, the adverse effects of chronic alcohol abuse were inhomogeneous with respect to cell loss and compensatory reactions. In the cingulate gyrus, chronic alcohol abuse resulted in loss of vascular endothelial cell (decreased ET-1 gene expression) and relatively increased astrocyte (GFAP expression) populations. In the cerebellar vermis, the reduced expression of Hu corresponds to neuronal loss, and increased GFAP and ET-1 expression correspond with increased abundance or activation of astrocytes and vascular endothelial cells. Therefore, chronic alcohol abuse has differential effects in terms of neurotoxicity and cell loss within different brain regions. Importantly, these findings, together with the observed increases in HNE and 8-OHdG immunoreactivity in the same structures, suggest that the cerebellum and cingulate gyrus are highly vulnerable targets of alcohol-mediated neurotoxicity. These adverse effects of ethanol could account for the progressive cognitive and motor deficits that occur in chronic alcoholics.

The molecular cell profiling studies also demonstrated that MAG-1 gene expression was not significantly reduced in the brains of chronic alcoholics. Given the frequent occurrence of white matter atrophy in chronic alcoholics and previous demonstration of reduced myelin associated gene expression in alcoholic brains, one would have expected to find significantly reduced MAG-1 mRNA levels in the alcoholics. However, one likely explanation for this discordant observation is that the cingulate gyrus and cerebellar vermis tissues analyzed were obtained from gray matter structures and therefore contained little in the way of white matter. To some degree, this point is corroborated by the higher levels of Hu compared with MAG-1 in the cerebellum, and similar levels of Hu and MAG-1 in the cingulate tissue samples.

Example 10

Figures 8A, 8B, 8C, 8D, 8E, 8F:
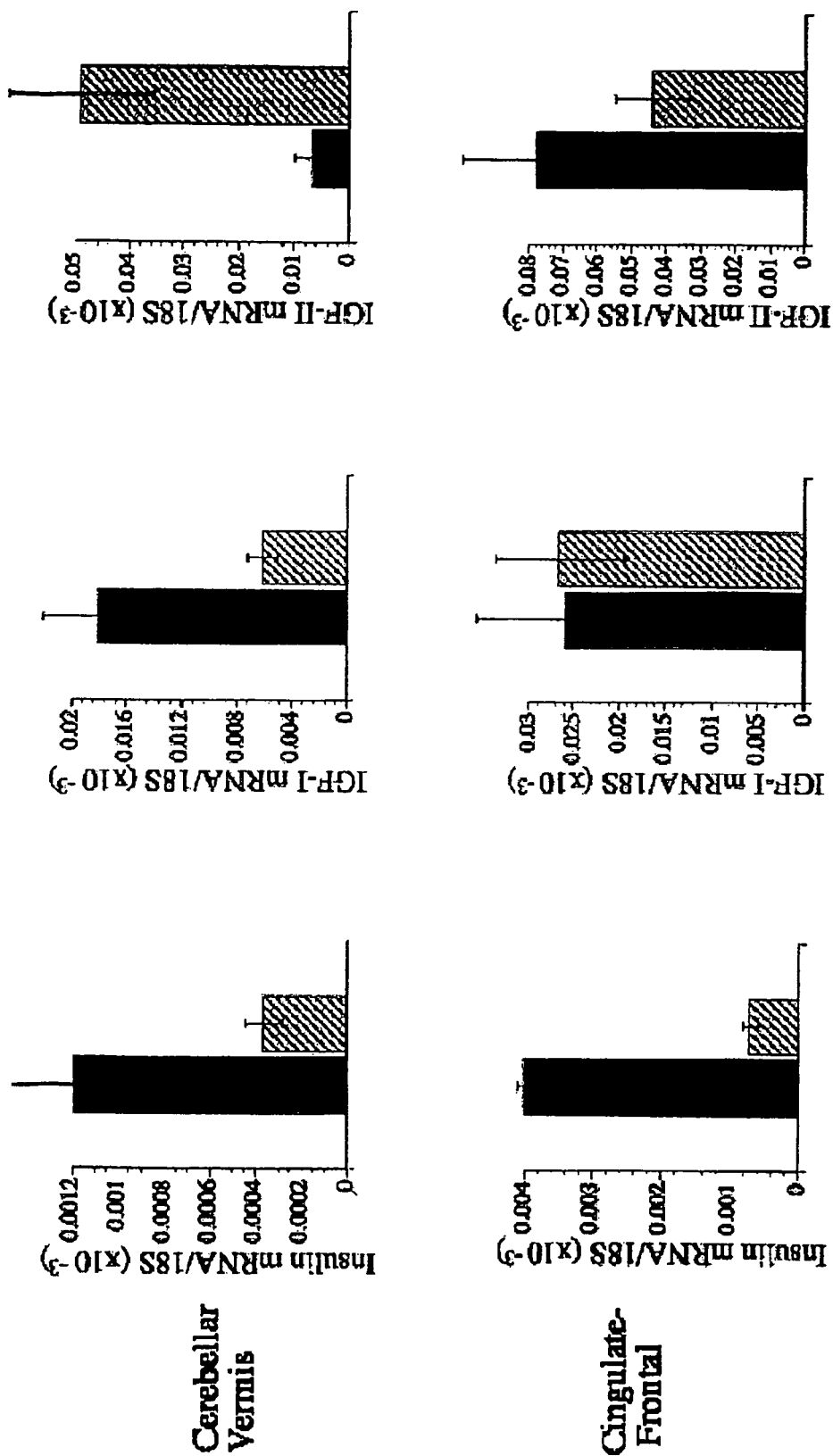
Figures 9A, 9B, 9C, 9D, 9E, 9F:
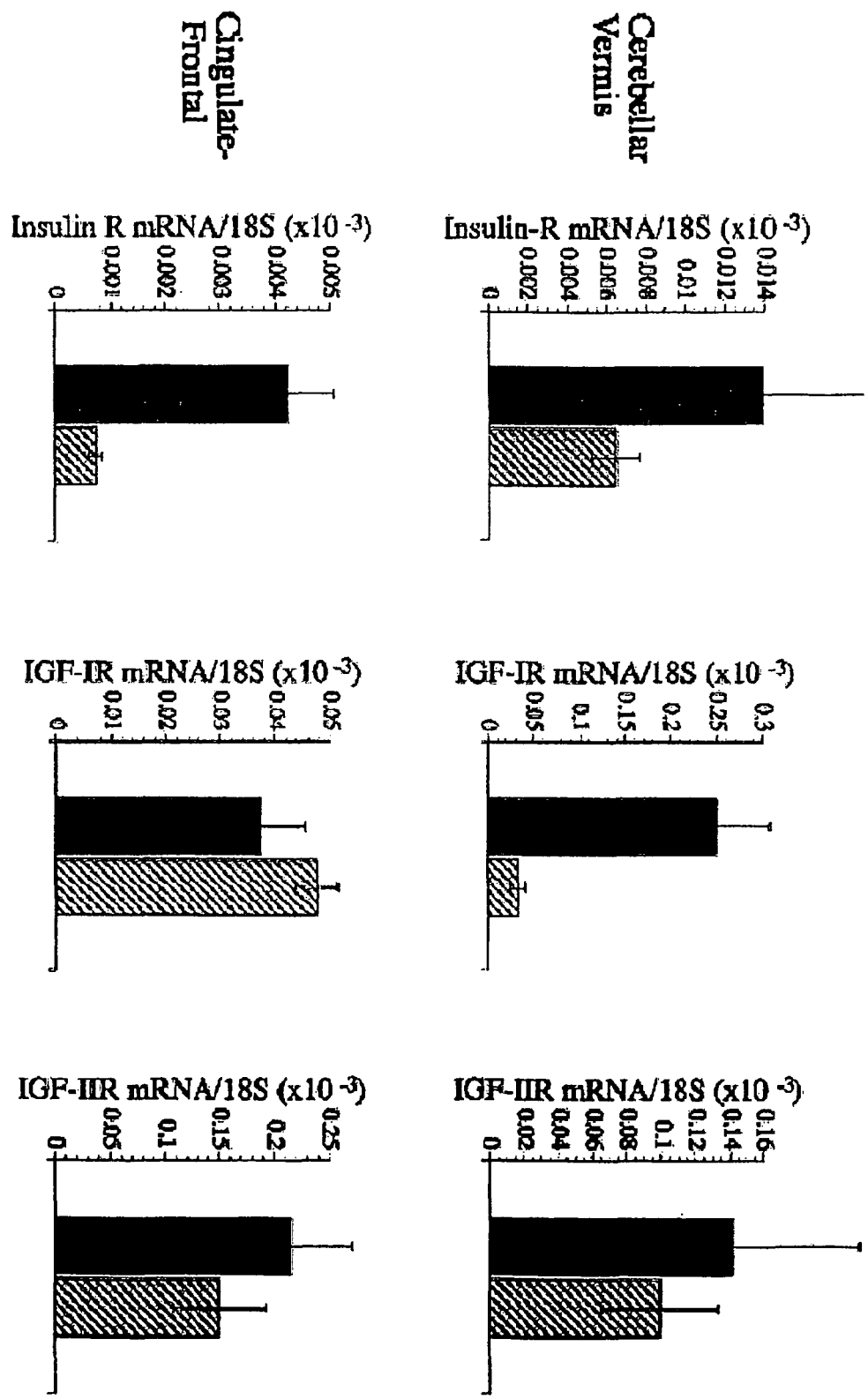

Effects of Ethanol on mRNA Expression of Insulin, IGF-I, and IGF-II Polypeptides, and the Insulin, IGF-I, and IGF-II Receptors Real time quantitative RT-PCR studies detected mRNA transcripts corresponding to insulin, IGF-I, and IGF-II polypeptides, and insulin, IGF-I, and IGF-II receptors in both control and alcoholic brains (FIGS. 8 and 9). In control brains, insulin and IGF-II gene expression were more abundant in the cingulate gyrus than in the cerebellar vermis, whereas IGF-I mRNA levels were similar in the two structures (FIG. 8). Overall, IGF-II was more abundantly expressed than insulin and IGF-I. Chronic alcohol abuse significantly reduced the mean levels of insulin gene expression in the cingulate gyrus and cerebellar vermis (FIGS. 8A-8B), and IGF-I expression in the cerebellum but not in the cingulate (FIGS. 8C-8D). Interestingly, IGF-II mRNA levels were significantly increased in alcoholic cerebella, but not in the cingulate gyrus (FIGS. 8E-8F).

In control brains, the mean expression levels of the insulin and IGF-I receptor genes were higher in the cerebellum than in the cingulate gyrus (FIGS. 9A-9D). In contrast, IGF-II receptor expression was somewhat higher in the cingulate compared with the cerebellar vermis (FIGS. 9E-9F). In the cingulate gyrus, IGF-II receptor expression was highest, followed by IGF-I, then insulin. In the cerebellar vermis, IGF-I receptor expression was highest, followed by the IGF-II receptor, and then the insulin receptor (FIG. 9). Chronic alcohol abuse significantly reduced insulin receptor gene expression in the cingulate gyrus and cerebellar vermis (FIGS. 9A-9B), IGF-I receptor expression in the cerebellum (FIGS. 9C-9D), and IGF-II receptor expression in the cingulate (FIGS. 9E-9F). In contrast, the chronic alcohol abuse did not significantly alter the expression the IGF-I receptor in the cingulate and IGF-II receptor in the cerebellum.

Example 11

Figures 10A, 10B, 10C, 10D, 10E, 10F:
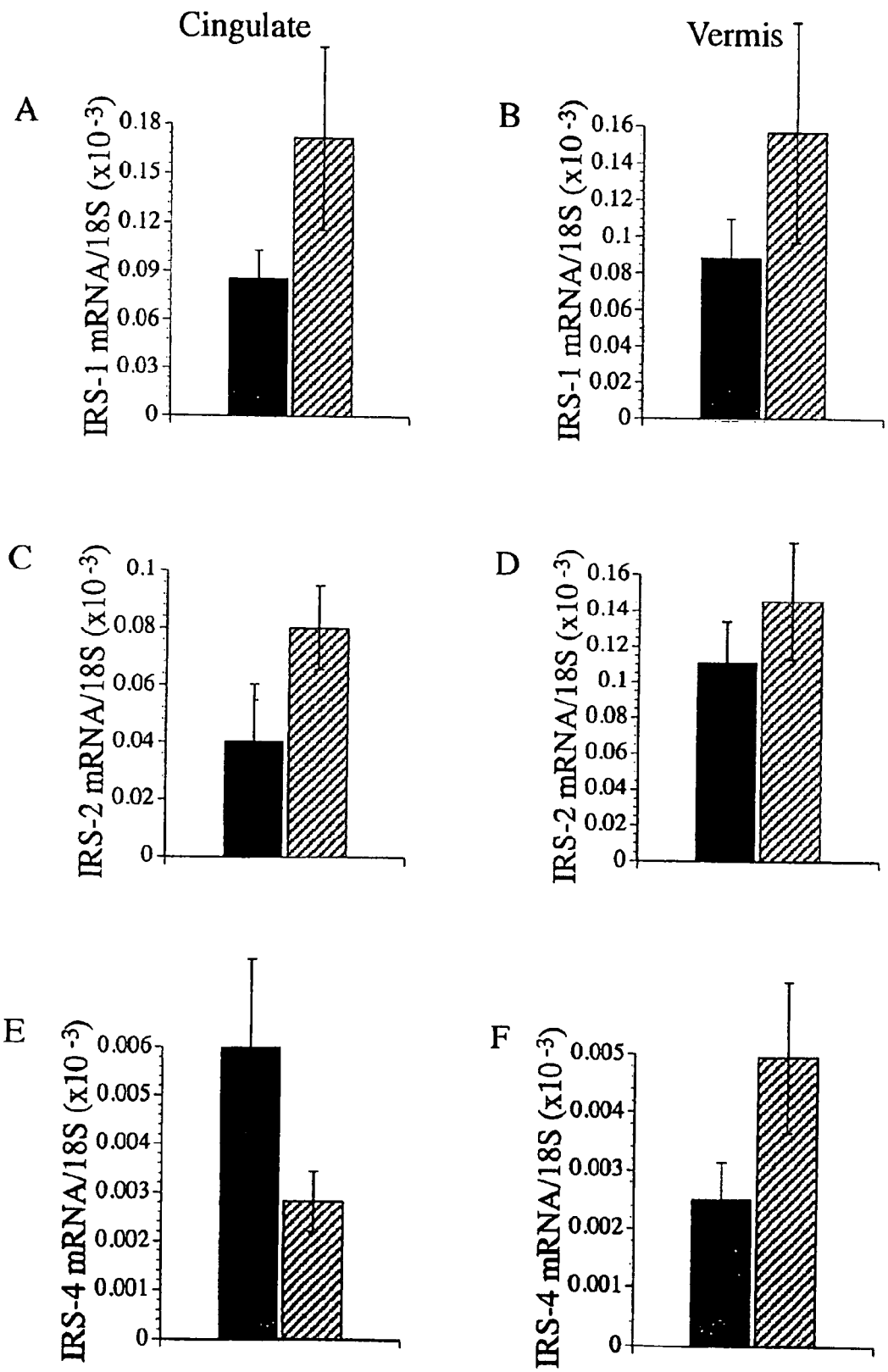

Insulin Receptor Substrate (IRS) Gene Expression Remains Intact in Chronic Alcoholic Brains Major responses to growth factor stimulated signaling through IRS molecules include increased cell growth and survival, and inhibition of apoptosis (Eves et al., *Mol. Cell. Biol.* 18:2143 (1998); Condorelli et al., *Mol. Cell. Biol.* 21:3025 (2001); Halestrap et al., *Biochem. Soc. Trans.* 28:170 (2000); Hirsch et al., *Cell. Biol. Toxicol.* 14:141 (1998); Xu et al., *J. Biol. Chem.* 278:26929 (2003); Yeon et al. *Hepatology* 38:703 (2003); Dahia et al., *Hum. Mol. Genet.* 8:185 (1999); Urso et al., *Life Sci.* 28:1053 (1981)). To examine the integrity of signaling pathways that are activated by insulin/IGF-I, IRS-1, IRS-2, and IRS-4 mRNA transcript levels were measured. IRS-3 was not examined because that isoform is only expressed in rodent adipose tissue. Real time quantitative RT-PCR detected expression of IRS-1, IRS-2, and IRS-4 mRNA transcripts in both control and chronic alcoholic brains (FIG. 10). In control cingulate tissue, IRS-1 expression was highest, followed by IRS-2 and then IRS-4 (FIGS. 10A, 10C, 10E), whereas in the cerebellar vermis, IRS-2 and IRS-1 were similarly abundant, and IRS-4 was again the least abundantly expressed (FIGS. 10B, 10D, 10F). Chronic alcohol abuse had no significant effect on the mean levels of IRS-1, IRS-2, or IRS-4 in either the cingulate or cerebellar vermis.

Real time quantitative RT-PCR studies demonstrated mRNA transcripts corresponding to insulin, IGF-I, IGF-II, their corresponding receptors, and IRS-1, IRS-2, and IRS-4 in the cingulate gyrus and cerebellar vermis, indicating that the genes required of insulin and IGF signaling are expressed in adult human brains. In control brains, IGF-I and IGF-II polypeptide genes were expressed at much higher levels than insulin, and in the cingulate gyrus, IGF-II was the dominant (most abundant) growth factor, whereas in the cerebellum, IGF-I was most abundantly expressed. Chronic alcoholics had markedly reduced levels of insulin gene expression in both regions, and reduced IGF-I expression in the cerebellum. Since neuronal loss with reduced expression of Hu was evident in the cerebellum and not in the cingulate gyrus, it is likely that neuronal survival is mediated by intact signaling through both insulin and IGF-I signaling. This point is corroborated by previous experimental data demonstrating that impaired neuronal survival caused by ethanol inhibition of insulin signaling could be partially rescued by treatment with IGF-I. The differential inhibitory effects of ethanol on insulin and IGF gene expression could account for region-specific differences in neuronal loss that occur with chronic alcohol abuse in humans.

Although IGF-II signaling mechanisms have not been thoroughly investigated in the CNS, recent studies in other tissues and cell types demonstrated that IGF-II can mediate cell survival by interacting with its own receptor and activating PI3 kinase-Akt via G-coupled protein signaling. Alternatively, IGF-II can bind to insulin and IGF-I receptors, and activate growth and survival signaling pathways through insulin receptor substrate-dependent mechanisms. Therefore, ethanol-mediated increases in IGF-II expression in the cerebellum could represent a positive compensatory response that would help promote neuronal survival in the setting of insulin and IGF-I withdrawal.

Insulin and IGF-I receptors were more abundantly expressed in the cerebellum than the cingulate gyrus, whereas IGF-II receptors were more abundant in the cingulate gyrus than in the cerebellum. The major effects of chronic alcohol abuse were to reduce the levels of the insulin receptor expression in the cingulate and cerebellar vermis, IGF-I receptor expression in the cerebellum, and IGF-II receptor expression in the cingulate gyrus. The reduced levels of insulin, IGF-I, and IGF-II receptor expression could reflect loss of cells that bear these receptors. Loss of insulin receptor-expressing cells in the brain contributes to insulin resistance and result in decreased expression of insulin-responsive genes. Loss of IGF-I and IGF-II receptor-expressing cells could adversely affect neuronal survival and plasticity. For example, signaling through IGF-I and IGF-II receptors can activate PI3 kinase-Akt via IRS pathways or G-coupled protein signaling mechanisms. The PI3 kinase-Akt pathway has a critical role in stimulating neuronal survival and neurite outgrowth which is required for plasticity.

Analysis of insulin receptor substrate genes, which have critical roles in transmitting growth, survival, and metabolic signals downstream from the insulin and IGF-I receptors, demonstrated no significant effects of chronic alcohol abuse on the expression levels of IRS-1, IRS-2, or IRS-4. This result contrasts with the findings in experimental models of FAS in which prominent reductions in IRS-1, IRS-2 and/or IRS-4 were detected in the developing cerebella (see below). Therefore, in contrast to FAS where impairments in insulin and IGF signaling occurs at multiple levels in the cascade, the major abnormalities in adult human alcoholic brains appear to stem from problems associated with growth factor and growth factor receptor expression and function, i.e., at proximal points within the signal transduction cascade.

Example 12

Ethanol Impairs Insulin and IGF Receptor Binding

Figures 11A, 11B, 11C, 11D, 11E, 11F:
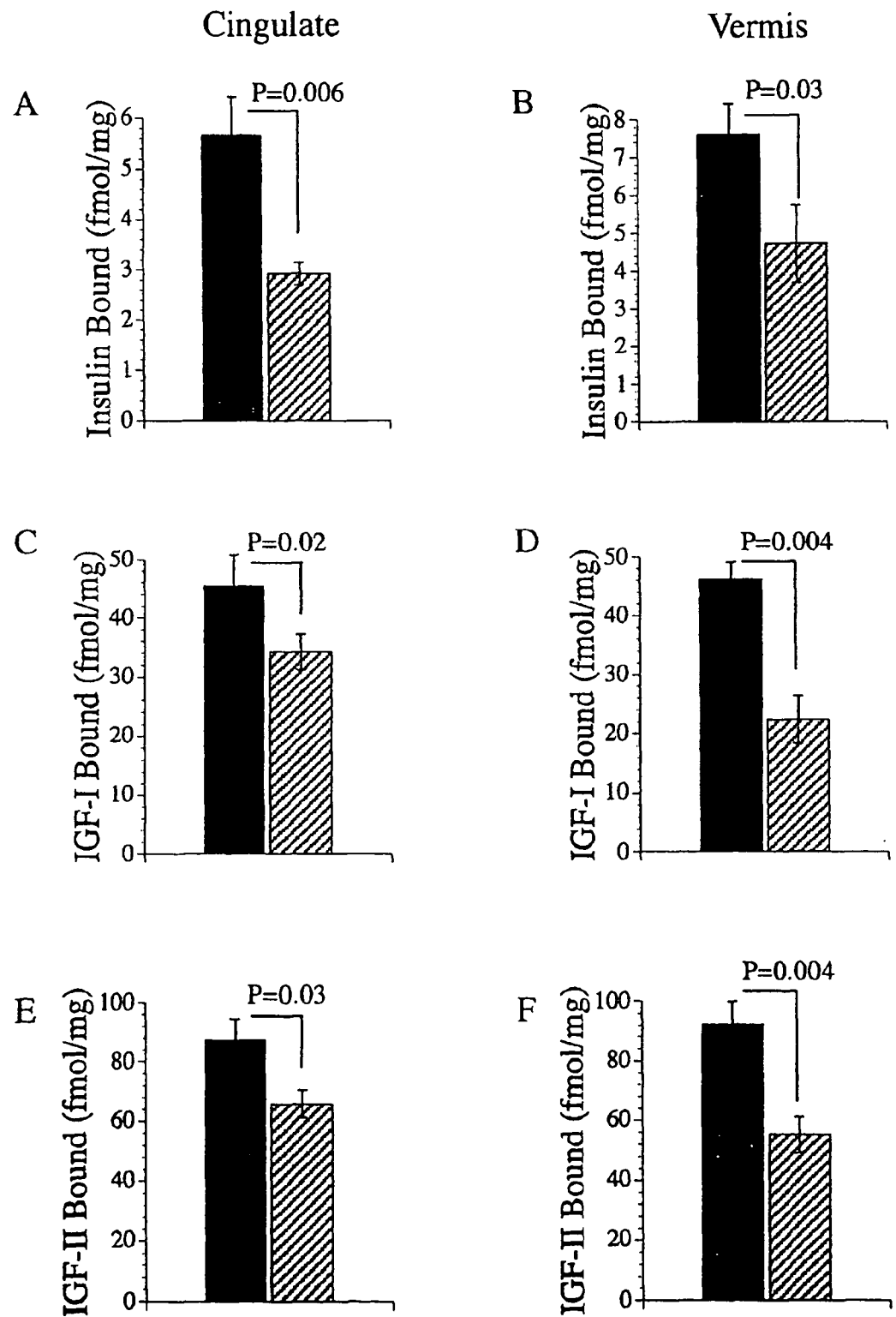

Given the variability in effects of chronic alcohol abuse on growth factor and growth factor receptor expression, it was of interest to determine if alcoholic brains could have impaired insulin/IGF signaling mediated through another mechanism. Effective ligand binding is critical to the insulin and IGF signaling cascades, and many of the downstream effects of impaired insulin signaling that have been reported in ethanol-exposed rat brains, including reduced neuronal survival, could be mediated by reduced insulin or IGF-I binding in the CNS. Equilibrium binding assays were performed by incubating cingulate gyrus and cerebellar vermis membrane protein extracts with $[^{125}I]$-labeled insulin, IGF-I, or IGF-II as tracer, in the presence or absence of excess cold ligand. Those studies demonstrated higher levels of IGF-II receptor binding (fmol/mg) compared with IGF-I and insulin receptor binding, and the lowest levels of binding to the insulin receptors, corresponding with the relatively low levels of insulin receptor expression in both the cingulate and vermis (FIG. 11). Chronic alcohol abuse resulted in significantly reduced insulin, IGF-I, and IGF-II receptor binding in the cingulate gyrus and cerebellar vermis (FIGS. 11A-11F).

Effective ligand binding is critical to the signaling cascade, and many of the previously reported downstream adverse effects of ethanol on insulin signaling including reduced neuronal survival could be mediated by impaired insulin or IGF-I binding in the CNS. Equilibrium binding assays demonstrated that chronic alcoholic brains have significantly reduced levels of insulin, IGF-I and IGF-II receptor binding in both the cingulate gyrus and cerebellar vermis. This suggests that chronic alcohol abuse impairs insulin, IGF-1, and IGF-II signaling mechanisms in different regions of the brain.

Importantly, the inhibition of insulin, IGF-I, and IGF-II receptor binding in the cerebellum was associated with histopathological evidence of neuronal loss, whereas in the cingulate gyrus, the tissue architecture was relatively preserved despite evidence of chronic oxidative injury. These differences may have been due to the smaller reductions in IGF-I and IGF-II receptor binding in the cingulate gyrus compared with the cerebellar vermis. Importantly, the findings herein and from previous studies suggest that ethanol inhibition of insulin and IGF signaling, which are required for cell survival and energy metabolism, is mediated at the level of receptor binding, i.e., the most proximal point within the signal transduction cascade. Moreover, the aggregate results highlight the importance of insulin as well as IGF resistance as mediators of impaired neuronal survival and persistent oxidative stress in chronic alcoholic brain disease.

Example 13

Ethanol-Mediated Impairments in Acetylcholine Homeostasis

Figures 12A, 12B, 12C, 12D:
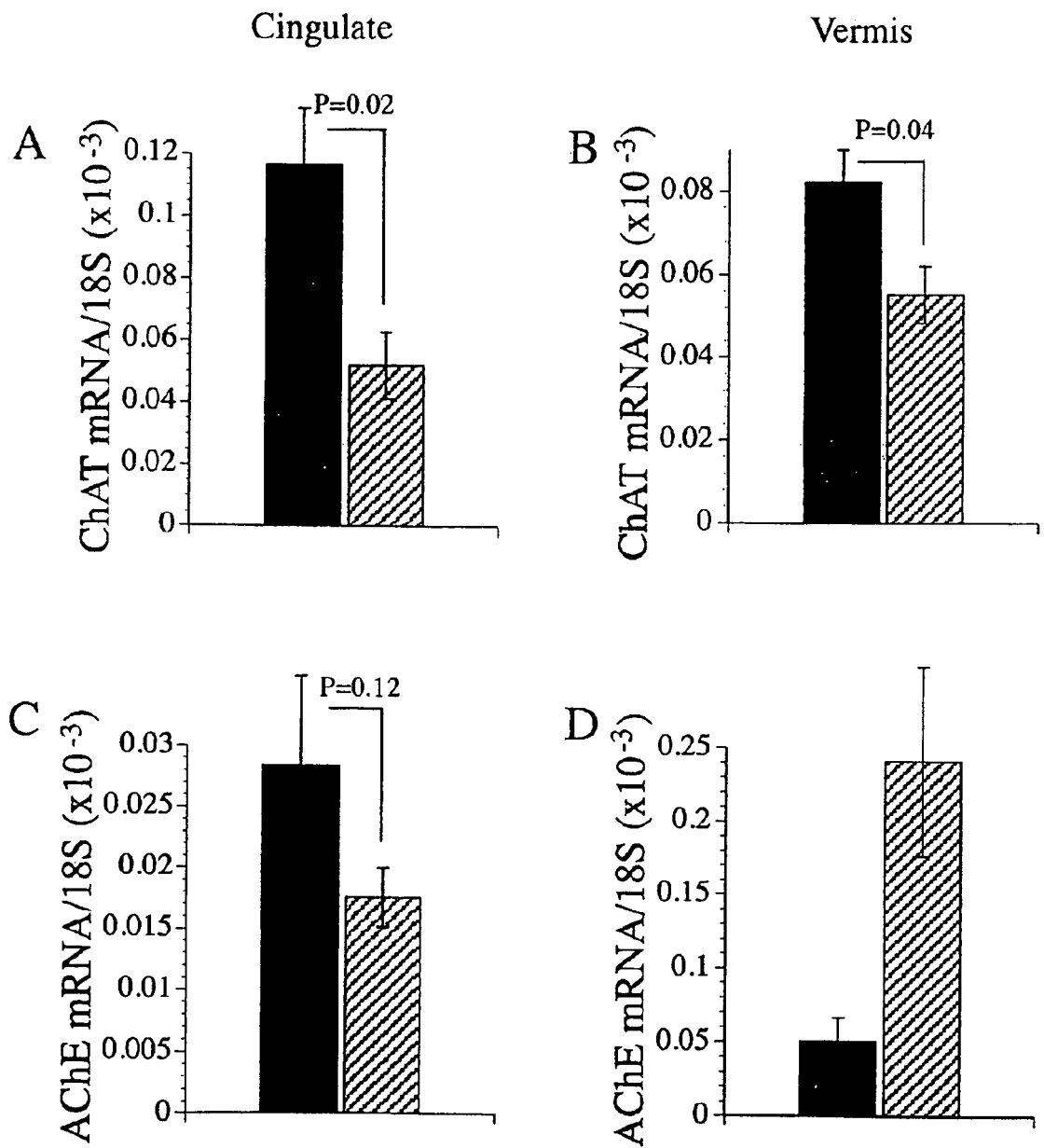

Acetylcholine has major functional roles in CNS cognitive and motor systems. Acetylcholine production requires adequate supplies of choline and acetyl-Co-A. Acetyl-Co-A is generated by energy metabolism, which in turn is driven by insulin and IGF-I stimulation. Recent studies demonstrated that choline acetyltransferase (ChAT) expression is regulated by insulin and IGF-I stimulation (Minana et al., *J. Neurochem.* 75:954 (2000)). Therefore, it was of interest to determine if ethanol inhibition of insulin and IGF signaling mechanisms were associated with deficits in ChAT. Since the steady-state levels of acetylcholine are negatively regulated by acetyl cholinesterase (AChE), it was also of interest to measure AChE mRNA levels. Real time quantitative RT-PCR studies demonstrated significantly reduced mean levels of ChAT mRNA expression in cingulate gyrus (FIG. 12A) and cerebellar vermis (FIG. 12B). In addition, in alcoholics, AChE expression was significantly reduced in the cingulate gyrus (FIG. 12C), but increased, although not statistically significant) in the cerebellar vermis (FIG. 12D).

Since ChAT expression is regulated by insulin and IGF-I stimulation, and acetylcholine is a major neurotransmitter that mediates CNS cognitive and motor functions, it was of interest to determine if the inhibitory effects of chronic alcohol abuse on insulin and IGF signaling impaired acetylcholine homeostasis in the brain. The real time quantitative RT-PCR studies demonstrated reduced ChAT expression in alcoholic cingulate gyrus and cerebellar vermis. These results correspond with the finding of impaired insulin and IGF-I receptor binding in alcoholic brains. Reductions in ChAT expression could result in deficits in acetylcholine biosynthesis, and without compensatory reductions in AChE expression, acetylcholine homeostasis would be adversely perturbed. In this regard, it is noteworthy that in the cingulate gyrus, AChE expression was significantly lower in the alcoholics, whereas in the cerebellum AChE expression was higher (although the differences did not reach statistical significance) in the alcoholics. These findings suggest that some degree of compensation occurred in the cingulate gyrus which could have helped restore acetylcholine homeostasis in that region, and thereby help to preserve cognitive function. However, with regard to the cerebellar vermis, the increased levels of AChE could have further impaired the acetyl choline homeostasis, and resulted in a worsening of motor deficits.

The aggregate results demonstrate that chronic alcohol abuse causes neurodegeneration characterized by neuronal loss, impaired neuronal function, and increased oxidative stress/lipid peroxidation in the adult human brain. Neuronal oxidative stress was more pronounced than cell loss, suggesting that many of the remaining neurons in the brain, although histologically intact, had major deficits in function as demonstrated by the significantly reduced levels of ChAT gene expression. The deficits in acetylcholine homeostasis produced by chronic alcohol abuse could impair cognitive and motor functions and thereby contribute to the CNS impairments commonly observed in chronic alcoholics. These studies suggest that ethanol-induced neuronal loss and neurodegeneration is mediated by two distinct but overlapping mechanisms: 1) insulin/IGF-1 resistance, which is mainly effectuated by impaired receptor binding; and 2) increased oxidative stress mediated by lipid peroxidation and DNA damage. Recently, ethanol impaired binding to the insulin and IGF-I receptors was linked to cholesterol depletion from the cell membranes and attendant reduced activation of the corresponding receptor tyrosine kinases (Soscia et al., *Cell. Mol. Life Sci.*, in press (2006)). It is noteworthy that nearly identical mediators of neuronal loss and impaired neuronal function were identified in association with cerebellar hypoplasia in experimental models of FAS (see below) and Alzheimer-type neurodegeneration, and in human brains with Alzheimer's disease (AD). What distinguishes alcoholic brain disease from AD is that in Alzheimer's, the fundamental problem centers around CNS insulin and IGF withdrawal followed by degeneration and loss of cells that respond to these trophic factors. In alcoholic brain disease, insulin/IGF resistance mediated by impaired binding to the corresponding receptors results in decreased signaling through growth, survival, and metabolic cascades. Both disease processes result in sustained oxidative stress. In AD, the oxidative stress is associated with increased expression of the amyloid precursor protein, pro-apoptosis gene activation, and mitochondrial dysfunction, whereas with chronic ethanol exposure, the oxidative stress is likely mediated by the toxic effects of ethanol, or its chief intermediary metabolite, acetaldehyde.

Example 14

General Methods for Rat Model of Chronic Ethanol Exposure During Gestation

Pregnant Long-Evans rats were fed with isocaloric liquid diets (BioServ, Frenchtown, N.J.) in which ethanol comprised 0%, 2%, 4.5%, 6.5%, 9.25% (v/v), which is equivalent to 0%, 8%, 18%, 26%, or 37% of the caloric content. These concentrations of ethanol are typically used to generate in vivo models of chronic ethanol exposure (Vander Top et al., *Alcohol Clin. Exp. Res.* 29:882 (2005)). The liquid diets were begun on gestation day 6 and continued throughout pregnancy. Rats were monitored daily to ensure equivalent caloric consumption and maintenance of body weight. Since the cerebellum represents a major target of ethanol neurotoxicity (Maier et al. *Alcohol* 23:49 (2001); Maier et al., *Alcohol Clin. Exp. Res.* 23:726 (1999); Mohamed et al., *I. Cytol. Exp. Neurol.* 97:35 (1987)), cerebella were used to study the effects of chronic gestational exposure to ethanol on insulin and IGF signaling in the developing CNS. Fresh tissue harvested immediately after birth was snap frozen in a dry ice-methanol bath and then stored at −80° C. for mRNA and protein studies. In addition, cerebella were immersion fixed in Histochoice fixative (Amresco Corp., Solon, Ohio) and embedded in paraffin. Histological sections were stained with hematoxylin and eosin and examined by light microscopy.

Receptor Tyrosine Kinase Assays:

Insulin or IGF-I receptor molecules were immunoprecipitated from individual 100 µg protein samples using rabbit polyclonal antibodies (1 µg/ml) and Protein A sepharose (Amersham-Pharmacia, Arlington Heights, Ill.) (Ausubel et al, (2002) Current Protocols in Molecular Biology. John Wiley & Sons New York). Receptor tyrosine kinase activity was measured in the immune precipitates using a non-isotopic assay (Chemicon International, Temecula, Calif.) according to the manufacturer's protocol with small modifications. Briefly, tyrosine phosphorylation of the biotinylated synthetic peptide substrate captured onto streptavidin-coated wells was detected with horseradish peroxidase conjugated anti-phospho-tyrosine and SuperSignal West Pico chemiluminescent substrate (Pierce Chemical Co., Rockford, Ill.). Luminescence was measured in a TopCount machine (Packard Instrument Co., Meriden, Conn.). The immunoprecipitates captured onto Protein A were subjected to Western blotting with densitometry in order to normalize the levels of tyrosine kinase activity to the receptor protein content in the reactions.

In Vitro Studies Using Neuronal Cultures:

In vitro experiments were used to examine the effects of ethanol on receptor binding and choline acetyltransferase (ChAT) and acetylcholinesterase (AChE) expression in cerebellar neurons. Primary neuronal cultures were generated with postnatal day 8 rat pup cerebellar tissue (Nikolic et al. *Genes Dev.* 10:816 (1996)). The cultures were maintained with Dulbecco's modified Eagle's medium (DMEM) supplemented with 5% fetal calf serum, 4 mM glutamine, 100 µM non-essential amino acid mixture (Gibco-BRL, Grand Island, N.Y.), 25 mM KCl, and 9 g/L glucose. Ethanol treatment was accomplished by placing the cultures (seeded in 6-well dishes or 96-well plates) in sealed chambers in which 50 mM ethanol was vaporized from a reservoir tray (de la Monte et al. *Alcohol Clin. Exp. Res.* 24:716 (2000); Banerjee et al. *Alcohol Clin. Exp. Res.* 22:2093 (1998)). Control cultures were identically treated but with water added to the reservoir tray. The chambers were flushed with gas containing 75% nitrogen, 20% oxygen, and 5% carbon dioxide. After 96 hours incubation at 37° C., the cells were harvested to measure insulin, IGF-I, and IGF-II receptor binding. Alternatively, the cells were serum-starved for 12 hours and then stimulated with 10 nM insulin, 10 mM IGF-I, 25 nM IGF-II, or vehicle for 16 hours, and RNA was harvested to measure ChAT and AChE expression. Parallel 96-well cultures stimulated with growth factors for 10 minutes were used to measure ATP, or for 16 hours to measure viability, and ChAT or AChE immunoreactivity. To investigate the role of membrane cholesterol content in relation to receptor binding, control and ethanol-exposed cells were treated with vehicle, 10 mM Methyl-β-cyclodextrin (MβCD), or 10 mM aqueous soluble cholesterol in Locke's buffer (154 mM NaCl, 5.6 mM KCl, 2.3 mM $CaCl_2$, 1.0 mM $MgCl_2$, 3.6 mM $NaHCO_3$, 5 mM glucose, 5 mM Hepes, pH 7.4) for 3 hours and then harvested for binding assays. To examine the effects of membrane cholesterol content on growth factor stimulated neuronal viability and function, identically treated 96-well cultures were stimulated with vehicle, 10 nM insulin, 10 nM IGF-I, or 25 nM IGF-II for 10 minutes and then analyzed for ATP content, or for 16 hours and then used to measure viability and ChAT or AChE immunoreactivity with the MICE assay (de la Monte et al., *Biotechniques* 26:1073 (1999)). ATP content was measured with the ATPLite assay (Packard, Meriden, Conn.). Viability was measured using the CyQuant assay (Molecular Probes, Eugene, Oreg.). Immunoreactivity was measured directly in the cultured wells using the microtiter immunocytochemical ELISA (MICE) assay (de la Monte et al., *Biotechniques* 26:1073 (1999)).

Cholesterol Assays:

Cholesterol content was measured using the Amplex Red assay kit (Molecular Probes, Eugene, Oreg.) according to the manufacturer's protocol. Preliminary studies demonstrated that the cholesterol levels and inter-group differences detected in lipid (chloroform:methanol) extracts were comparable to those measured in RIPA buffer extracts, as indicated by the manufacturer. Therefore, it was not necessary to perform the analyses with lipid extracts of the tissue samples. Briefly, tissue homogenates were prepared in RIPA buffer as described above. Samples, serially diluted in 1× reaction buffer (provided with the kit), were incubated with 150 µM Amplex Red reagent, 1 U/ml horseradish peroxidase, 1 U/ml cholesterol oxidase, and 0.1 U/ml cholesterol esterase in final reaction volumes of 100 µl. Reactions were incubated at 37° C. for 30 minutes and fluorescence was measured in a Fluorocount microplate reader (Packard Instrument Co., Meriden, Conn.) (Ex 560 nm/Em 590 nm). A standard curve was simultaneously generated using a cholesterol standard provided with the kit. The levels of cholesterol were normalized to protein concentration in the samples.

Immunohistochemical staining, RT-PCR assays (using the PCR primers listed in Table 1), and receptor binding assays were performed as described in Example 1.

Example 15

Dose-Effect of Chronic Gestational Exposure to Ethanol on Birth Weight and Cerebellar Development Pup birth weights in the 8%, 18%, and 26% ethanol groups were not significantly reduced relative to control. However, pups from dams that were fed with the 37% ethanol-containing diet had a significantly lower mean body weight relative to control (P<0.05; Table 4). Although pups in the 8% ethanol diet group had the highest mean body weight relative to control (P<0.01), they nonetheless sustained multiple abnormalities in CNS gene expression and function similar to the other ethanol-exposed groups, suggesting that ethanol-induced neurotoxicity in the developing CNS can occur with normal or increased birth weight. One potential interpretation of the increased birth weight in the low ethanol exposure group is that the pups mainly exhibited effects of insulin resistance, similar to that which occurs in the offspring of Type 2 diabetics. At the highest concentration of ethanol used, the blood alcohol levels achieved (Table 3) were within the range legally regarded as intoxicating in humans, and previously observed in alcoholics taken to an emergency room for acute care (Fulop et al. *Am. J. Med.* 80:191 (1986); Jagger et al., *Neurosurgery* 15:303 (1984)).

TABLE 3

Effects of chronic gestational exposure to ethanol on birth weight

| Ethanol Dose | 0% | 8% (2%) | 18% (4%) | 26% (6.5%) | 37% (8.2%) |
|---|---|---|---|---|---|
| Birth Wt (gm) | 5.2 ± 0.3 | 6.2 ± 0.5** | 4.9 ± 0.5 | 4.6 ± 0.5 | 3.9 ± 0.3* |
| # Pups | 12 | 13 | 11 | 10 | 8 |

TABLE 3-continued

Effects of chronic gestational exposure to ethanol on birth weight

| Ethanol Dose | 0% | 8% (2%) | 18% (4%) | 26% (6.5%) | 37% (8.2%) |
|---|---|---|---|---|---|
| Blood Alcohol Level (mM) | 0 | 7.8 ± 2.6* | 20.9 ± 5.6** | 31.3 ± 8.3** | 51.1 ± 11.9** |

Pregnant dams were fed with Lieber-DiCarli isocaloric liquid diets containing different concentrations of ethanol as a percentage of the caloric content or (v/v) beginning on gestation day 6 and continuing through pregnancy. Pups were weighed immediately after birth. Maternal blood was obtained after delivery to measure blood alcohol concentration. The data show the mean ± S.D. of results. Data were analyzed statistically using ANOVA with the Tukey-Kramer post-hoc significance test. Significant P-values are relative to control (*P < 0.05;
**P < 0.005).

Example 16

Ethanol Dose-Dependent Structural Abnormalities Related to Cell Density, Cyto-Architecture, and Cell Migration Control cerebella had well-delineated foliation (folding) and lamination of the cortex with discrete boundaries corresponding to the external and internal granule cell, Purkinje cell, and molecular layers, and densely populated granule cell layers with only scattered apoptotic (condensed or fragmented) nuclei. With increasing ethanol dose, the cerebellar cortex foliation became progressively simplified, the cortical lamination became less discrete, and the cell density within the granule layers declined (FIGS. 13A, 13D, 13G, 13J, 13M). Reduced cortical foliation was associated with flattening and broadening of the cortical surface and limited sulcation (shallow grooves). The reduced delineation of the cortical layers was associated with broadening and irregular lamination of the inner granule and Purkinje cell layers, and narrowing of the external granule cell and molecular layers. Higher magnification images of the external granule cell layer demonstrated progressive ethanol-dose dependent reductions in cell density. In the 37% ethanol group, cell loss and apoptosis were conspicuous, and the residual cell types differed from control in that many of the cells had morphological features of glia (pale vesicular nuclei) rather than neuroblastic elements (compactly arranged small round or oval nuclei with dense chromatin) (FIGS. 13B, 13E, 13H, 13K, and 13N). Immunohistochemical staining to detect single-stranded DNA, which corresponds to DNA breakage prior to apoptosis, revealed ethanol dose-dependent increases in the densities of labeled nuclei. (FIGS. 13C, 13F, 13I, 13L, 13O). However, the prominent cell loss and apoptosis in the 37% ethanol group was associated with relatively reduced nuclear labeling, probably because many cells had already undergone apoptosis.

In humans, chronic in utero exposure to high levels of ethanol impairs body and brain growth, resulting in small for gestational age infants and increased incidences of microencephaly, reduced white matter volume, ventriculomegaly, and attention deficit hyperactivity disorders (Goodlett et al., *Exp. Biol. Med.* (*Maywood*) 230:394 (2005)). In addition, major structural and functional abnormalities in the basal ganglia and cerebellum account for the prominent motor system deficits associated with human cases of FAS and fetal alcohol spectrum disorders. The FAS-induced cerebellar abnormalities are associated with impairments in neuronogenesis, neuronal survival, neuronal adhesion, and neuronal migration (Goodlett et al., *Exp. Biol. Med.* (*Maywood*) 230:394 (2005); Guerri, *Alcohol Clin. Exp. Res.* 22:304 (1998); Lewis et al. *Alcohol* 20:195 (1985)). In the present experimental model of FAS, chronic gestational exposure to relatively high levels of ethanol (37% caloric content or 8.2% v/v) that resulted in maternal blood ethanol concentrations of 51.1±11.9 mM, significantly reduced the mean birth weight and produced striking teratogenic effects on CNS development in the offspring as previously reported (Xu et al., *J. Biol. Chem.* 278: 26929 (2003)). The analysis of pups with different levels of in utero ethanol exposure provided new information about the degree to which ethanol-induced CNS abnormalities could be produced with different ethanol doses. The investigations were focused on the cerebellum because it represents a major CNS target of ethanol neurotoxicity in both humans and experimental animals.

The results from the in vivo studies demonstrated mixed responses to the graded doses of ethanol exposure. Dose-dependent adverse effects of ethanol were observed with respect to cerebellar development, neuronal gene expression (neuronal survival), astrocyte and microglial cell proliferation, ATP content (energy metabolism), and ChAT and AChE expression. In contrast, the levels of myelin-associated glycoprotein gene expression, insulin, IGF-I, and IGF-II receptor binding, and insulin and IGF-I receptor tyrosine kinase activities were similarly reduced following exposure to low or high concentrations of dietary ethanol, i.e., these adverse effects of ethanol were not graded. Therefore, only some consequences of chronic gestational exposure to ethanol appear to be dose-dependent, and may be linked to impaired neuronal survival and attendant proliferation of astrocytes and activation of microglial cells in response to injury. On the other hand, the ethanol dose-independent abnormalities, such as the impairments in receptor binding, may be mediated by other factors such as secondary toxic effects of ethanol and/or its metabolites, but further studies will be required to fully characterize the mechanisms of these responses.

The cerebella of ethanol-exposed pups exhibited hypoplasia, reduced cell survival, and impaired neuronal migration, and the severity of these lesions was graded with respect to ethanol dose. Histopathological studies showed that chronic in utero exposure to ethanol produced dose-dependent cell loss associated with increased DNA damage, and marked alterations in the structure (foliation) and cytoarchitecture (lamination) of the cerebellar cortex due to impaired neuronal migration.

Example 17

Ethanol-Induced Pathological Shifts in Cell Type in the Cerebellum

To determine if the ethanol dose-dependent increases in cerebellar hypoplasia and apoptosis produced pathological shifts in the remaining cell populations, real time quantitative RT-PCR studies were used to measure mRNA transcripts encoding Hu neuronal ribosomal RNA binding protein (Hu et al., *J. Neurosci. Res.* 78:637 (2004); Kumagai et al., *J. Neuroimmunol.* 93:37 (1999); Szabo et al., *Cell* 67:325 (1991)), myelin-associated glycoprotein-1 (MAG-1) for oligodendroglia, glial fibrillary acidic protein (GFAP) for astrocytes, allograft inflammatory factor-1 (AIF-1) for microglia (Imai et al., *Biochem. Biophys. Res. Commun.* 224:855 (1996); Ito et al., *Stroke* 32:1208 (2001)), and endothelin-1 (ET-1) for endothelial cells. The ng quantities of each specific mRNA transcript detected were normalized to the 18S RNA levels measured in the same samples, and results from 8-12 animals per group were analyzed statistically. The studies demonstrated ethanol-mediated reductions in Hu and MAG-1 expression, and increases in GFAP and AIF-1 expression, but no significant alteration in ET-1 (FIG. 14). The inhibitory effects on Hu and the stimulatory effects on GFAP and AIF-1 were ethanol dose-dependent, whereas the inhibitory effects on MAG-1 expression were similar for all ethanol dosages utilized.

The molecular studies designed to assess the relative abundance of different brain cell populations demonstrated significantly reduced Hu and MAG-1 expression, corresponding to neurons and oligodendroglia, and increased GFAP and AIF-1, corresponding to astrocytes and microglia, respectively. These results suggest that both neurons and oligodendroglia represent targets of ethanol neurotoxicity in the CNS, and corroborate the previous findings of neuronal loss and reduced white matter volume in human cases of FAS (Ozer et al., *Clin. Neuropathol.* 19:21 (2000); Bandstra et al., *Neurotoxicol. Teratol.* 23:545 (2001)). Although the mechanisms of neuronal and oligodendroglial cell loss in the context of chronic gestational exposure to ethanol are not entirely understood, potential mediators include: 1) impairments in insulin stimulated cell survival due to insulin receptor resistance (see below) and impaired signaling downstream through PI3 kinase (Xu et al., *Biochem. J.* 310:125 (1995)); 2) reduced local CNS production of insulin which is needed for cell survival, i.e., trophic factor withdrawal; and 3) increased oxidative stress due to mitochondrial dysfunction. The molecular cell profiling studies also demonstrated increased GFAP expression, which could reflect increased numbers and/or activation of astrocytes following neuronal and oligodendroglial cell loss. In addition, the increased levels of AIF-1 could be important with regard to mechanisms of tissue injury since microglia release of cytokines and nitric oxide, leading to increased oxidative stress and mitochondrial dysfunction, which are known mediators of ethanol-induced cell loss both in vivo and in vitro.

Example 18

Figures 15A, 15B, 15C, 15D, 15E, 15F, 15G, 15H:
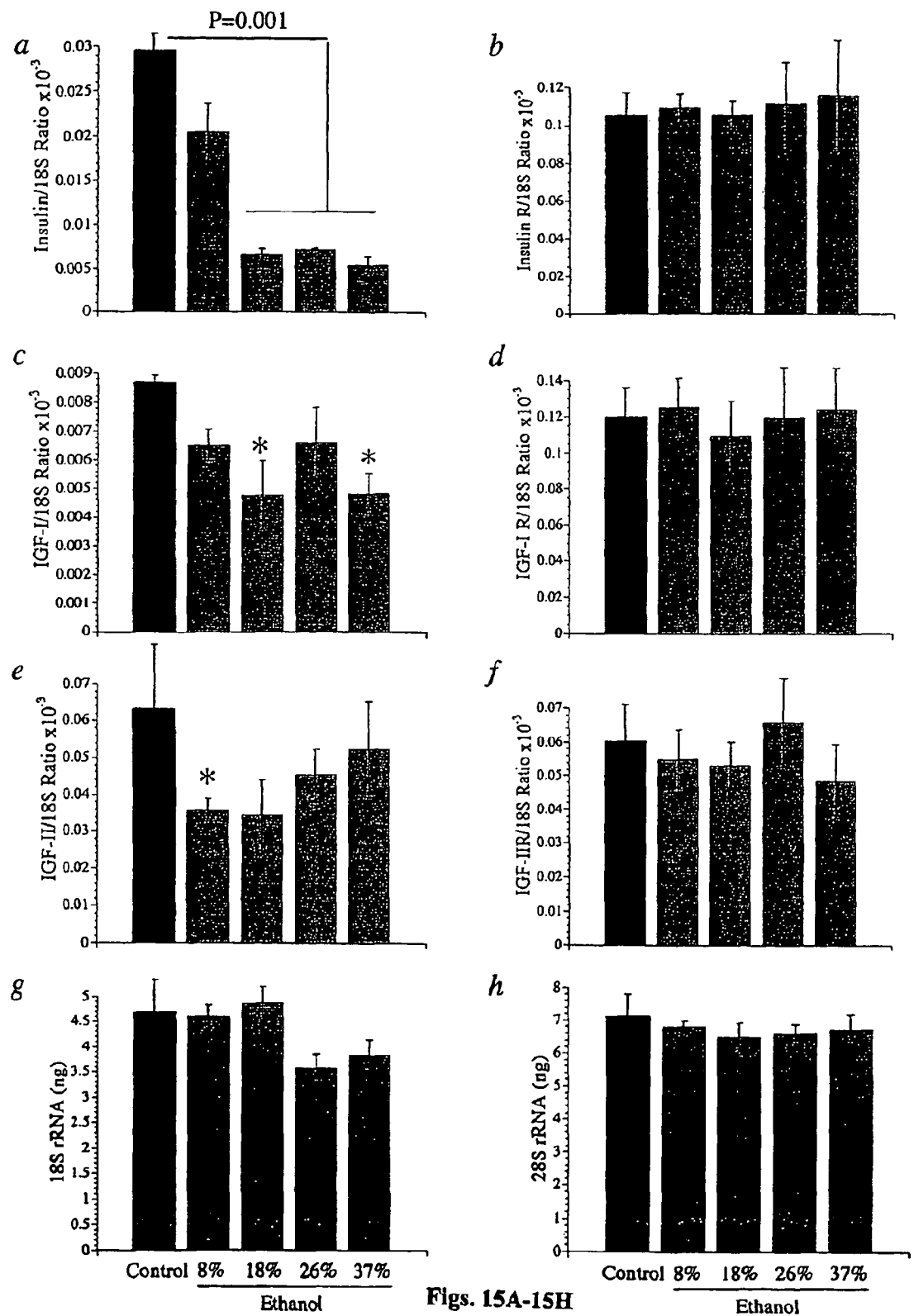

Effects of Ethanol on Cerebellar Expression of Insulin, IGF-I, and IGF-II, and the Insulin, IGF-I, and IGF-II Receptors Real time quantitative RT-PCR studies detected mRNA transcripts corresponding to insulin, IGF-I, and IGF-II polypeptide genes, and insulin, IGF-I, and IGF-II receptors in both control and ethanol exposed cerebella (FIG. 15). Insulin and IGF-II were more abundantly expressed than IGF-I. Gestational exposure to ethanol produced significant reductions in insulin gene expression that were not dose-dependent, i.e., even low levels of ethanol exposure inhibited insulin gene expression (FIG. 15A). Gestational exposure to ethanol also caused modest reductions in the levels of IGF-I (FIG. 15C) and IGF-II (FIG. 15E), although the trends were not dose-dependent. Insulin and IGF-I receptor mRNA levels were similar, and both were 1.5- to 2.0-fold higher than IGF-II receptor expression (FIGS. 15B, 15D, 15F). Chronic gestational exposure to ethanol did not significantly inhibit insulin, IGF-I, or IGF-II receptor expression, although at the highest concentration used, IGF-II receptor expression was reduced relative to control. Ribosomal 18S (FIG. 15G) and 28S (FIG. 15H) levels measured in the same samples were similarly abundant in all groups. Corresponding with the results obtained by RT-PCR, Western blot analysis demonstrated similar levels of insulin and IGF-I receptor expression in control and ethanol-exposed cerebella.

The cell loss associated with chronic gestational exposure to ethanol selectively reduced the relative populations of neurons and oligodendroglia. Previous studies demonstrated that these cell types are responsive to insulin and/or IGF-I stimulation, and that intact insulin or IGF-I signaling mechanisms mediate neuronal and oligodendroglial cell survival (Dudek et al., *Science* 275:661 (1997); Kummer et al., *J. Biol. Chem.* 272:20490 (1997); Yamaguchi et al., *J. Biol. Chem.* 276:5256 (2001); Barres et al., *Development* 118:283 (1993); Barres et al., *Cell* 70:31 (1992); Ness et al., *Mol. Cell. Neurosci.* 20:476 (2002)). Growth factor signaling can be modulated by altering the availability of growth factors, the expression of growth factor receptors, or the responsiveness of receptors to growth factor stimulation. Therefore, it was of interest to determine if the preferential loss of neurons and oligodendroglia in ethanol-exposed cerebella was associated with reduced expression of insulin, IGF-I, IGF-II, or their corresponding receptors.

Real time quantitative RT-PCR studies demonstrated significant ethanol-associated reductions in the levels of insulin, IGF-I, and IGF-II gene expression, although only the insulin gene expression levels were sharply and consistently reduced at higher levels of ethanol exposure. In contrast, insulin, IGF-I, and IGF-II receptor expression were not consistently affected by in utero exposure to ethanol. Variability in the effects of ethanol on insulin and IGF receptor expression was noted both in the present study, and with respect to previously published results. The explanation for this phenomenon is not obvious, but it suggests that in vivo, the genes regulating the expression of insulin and IGF receptors are less vulnerable to the adverse effects of ethanol than are the signaling functions of the corresponding proteins. This concept is supported by the profound inhibitory effect of insulin on insulin and IGF receptor gene expression detected after chronic in vitro ethanol exposure of cultured cerebellar neurons. These results suggest that one mechanism by which ethanol impairs CNS functions that require insulin and IGF signaling is to inhibit local CNS growth factor production. This effect could be mediated by either selective cell killing, or down-regulation of growth factor genes. However, one discordant finding was that insulin and IGF-I receptor tyrosine kinase activities were significantly reduced by gestational exposure to ethanol, irrespective of dose. Moreover, previous in vitro studies demonstrated that ethanol impairs insulin and IGF-I receptor tyrosine phosphorylation and kinase activation, despite exogenous supply of the growth factors (Seiler et al., *Alcohol Clin. Exp. Res.* 24:1869 (2000); Seiler et al., *J. Neurochem.* 76:573 (2001)). These observations suggest that factors other than growth factor gene expression contribute to ethanol-mediated impairment of insulin and IGF signaling in the CNS.

Example 19

Ethanol Impairs Insulin and IGF Receptor Binding

Effective ligand binding is critical to the signaling cascade, and many of the downstream effects of impaired insulin signaling that have been reported in ethanol-exposed brains, including reduced neuronal survival could be mediated by reduced insulin or IGF-I binding in the CNS. Equilibrium binding assays were performed by incubating cerebellar membrane protein extracts with [$^{125}$I]-labeled insulin, IGF-I, or IGF-II as tracer, in the presence or absence of excess cold ligand. The equilibrium binding studies demonstrated higher levels of specific binding (fmol/mg) to the IGF-I and IGF-II receptors compared with insulin receptors. The ethanol-exposed groups all had significantly-reduced binding to the insulin, IGF-I and IGF-II receptors relative to control. In addition, ethanol exposure impaired insulin and IGF-I receptor binding to greater degrees (~80%) than IGF-II receptor binding (~50%). However, the degrees to which receptor binding was impaired were not ethanol dose-dependent.

Effective ligand binding is critical to the signaling cascade, and many of the previously reported downstream adverse effects of ethanol on insulin signaling including reduced neuronal survival could be mediated by impaired insulin or IGF-I binding in the CNS. The equilibrium binding assays demonstrated higher levels of specific binding to the IGF-I and IGF-II receptors relative to the insulin receptor in control brains, and reduced binding to the insulin, IGF-I and IGF-II receptors in ethanol-exposed relative to control brains. In addition, chronic gestational ethanol exposure impaired binding to the insulin and IGF-I receptors to greater extents (~80%) than to the IGF-II receptors (~50%). However, the inhibitory effects of ethanol on insulin, IGF-I and IGF-II binding were not dose-dependent, and instead the degree to which binding was reduced was similar among the different ethanol-dosage groups. Therefore, despite relatively preserved levels of insulin and IGF receptor expression, ligand binding to the receptors was markedly reduced following chronic in utero exposure to ethanol. Further in vitro studies showed that ligand binding was also impaired after relatively brief periods (96 hours) of ethanol exposure (see below). These results suggest that the inhibitory effects of ethanol on insulin and IGF signaling required for cell survival and energy metabolism in the brain are mediated at the level of receptor binding, i.e., the most proximal point in the signal transduction cascade.

The potential consequences of impaired signaling through the insulin and IGF-I receptors include reduced signaling downstream through IRS molecules and decreased activation of pathways required for cell growth and survival. However, the effects of impaired IGF-II gene and receptor expression are less well understood. IGF-II is expressed in various regions of the fetal brain, but mainly in cells of mesenchymal and neural crest origin (D'Ercole et al. *Horm. Res.* 45:5 (1996); D'Ercole et al. *Ann. NY Acad. Sci.* 692:149 (1993)). IGF-II receptors are also widely distributed in fetal brains (D'Ercole et al., *Horm. Res.* 45:5 (1996); D'Ercole et al. *Ann. NY Acad. Sci.* 692:149 (1993)). Targeted gene mutation studies demonstrated that IGF-II stimulates prenatal brain growth and activates insulin stimulated signaling pathways via the insulin receptor (Nakae et al., *Endocr. Rev.* 22:818 (2001)). Although IGF-H receptors may also function as scavengers for IGF-II by promoting transport and degradation of the protein (Ghosh et al., *Nat. Rev. Mol. Cell. Biol.* 4:202 (2003)), there is growing evidence that IGF-II can stimulate growth and motility through activation of its own receptor (Herr et al., *J. Clin. Endocrinol. Metab.* 88:4811 (2003); Zygmunt et al. *Mol. Hum. Reprod.* 11:261 (2005)). In this regard, IGF-II stimulated growth and motility signals can be transmitted through G-coupled proteins via IRS-independent pathways (Patel, *Pharmacol. Rev.* 56:371 (2004)). In addition, cellular proliferation in response to IGF-II stimulation can be mediated by signaling through the insulin and IGF-I receptors, thereby converging to IRS pathways.

Example 20

Effects of Gestational Exposure to Ethanol on Insulin and IGF-I Receptor Tyrosine Kinase Activities Studies were done to characterize the degree to which ethanol-associated impairments in receptor binding were associated with reductions in insulin and IGF-I receptor tyrosine kinase activities, and insulin and IGF-I receptor protein expression. Receptor protein levels were measured by Western blotting with digital image densitometry. Receptor tyrosine kinase activities were measured in immunoprecipitates using a non-isotopic luminescence-based assay. The studies demonstrated significantly reduced levels of both insulin- and IGF-I receptor tyrosine kinase activities, but similar levels of insulin and IGF-I receptor protein expression in cerebellar tissue from ethanol-exposed relative to control pups. Corresponding with the binding assay results, the ethanol-associated reductions in receptor tyrosine kinase activity were not dose-dependent and were similarly reduced in cerebella from pups exposed to different in utero levels of dietary ethanol. Since the results were normalized to insulin and IGF-I receptor protein levels in the immunoprecipitates (as detected by Western blot analysis with densitometry), the ethanol-associated reductions in insulin and IGF-I receptor tyrosine kinase activities were not attributable to altered growth factor receptor expression. A major consequence of ethanol-impaired insulin and IGF-I signaling in CNS neurons is reduced energy metabolism due to deficiencies in glucose utilization and ATP production (de la Monte et al., *Cell. Mol. Life Sci.* 62:1131 (2005)). To determine the effects of different levels of chronic in utero exposure to ethanol in relation to energy metabolism, ATP content was measured in cerebellar tissue homogenates using a luminescence-based assay. Those studies demonstrated ethanol dose-dependent progressive reductions in cerebellar ATP content, with significant differences from control detected in samples obtained from pups exposed to the 18%, 26%, or 37% ethanol-containing diets.

Previous studies demonstrated ethanol inhibition of insulin receptor tyrosine phosphorylation and kinase activity, vis-à-vis intact insulin receptor protein expression. The present studies extended this line of investigation by characterizing ethanol dose-effects on insulin- and IGF-I receptor tyrosine kinase activities. The results demonstrated that chronic gestational exposure was associated with significantly reduced levels of insulin and IGF-I receptor tyrosine kinase activities; however, corresponding with the non-tiered effects of ethanol on ligand binding, the ethanol-associated reductions in insulin and IGF-I receptor tyrosine kinase activities were also not graded, and instead the levels were similarly reduced in all ethanol-exposed groups relative to control. This suggests that at least some aspects of insulin and IGF-I signaling in the brain are substantially impaired by relatively low levels of chronic gestational exposure to ethanol. To determine if these adverse effects of ethanol required long-term exposure, in vitro experiments were conducted using cerebellar neuron cultures that were treated with 50 mM ethanol for 4 days (see below). The findings of reduced insulin and IGF binding, and the previously observed reductions in insulin and IGF-I stimulated tyrosine kinase activation in the ethanol-treated neuronal cultures indicate that short-term ethanol exposure, such as with binge drinking, can also have pronounced inhibitory effects on insulin and IGF-I receptor function. The proximal nature of this molecular lesion provides a means by which ethanol could interfere with diverse downstream functions that are mediated by insulin or IGF-I signaling, including cell survival and energy metabolism.

Example 21

Ethanol-Associated Impairments in Acetylcholine Homeostasis

Acetylcholine has major functional roles in CNS cognitive and motor systems. Acetylcholine production requires adequate supplies of choline and acetyl-Co-A. Acetyl-Co-A is generated by energy metabolism, which in turn is driven by insulin and IGF-I stimulation. Recent studies demonstrated that choline acetyltransferase (ChAT) expression is regulated by insulin and IGF-I stimulation (Rivera et al., *J. Alzheimers Dis.* 8:247 (2005)). Therefore, it was of interest to determine if ethanol inhibition of insulin and IGF-I signaling mechanisms were associated with deficits in ChAT. Since the steady-state levels of acetylcholine are negatively regulated by acetylcholinesterase (AChE), it was also of interest to measure AChE mRNA levels. Real time quantitative RT-PCR studies demonstrated significant reductions in the mean levels of ChAT (FIG. 16A) and increases in AChE (FIG. 16B) expression in ethanol-exposed cerebellar tissue. The levels of ChAT mRNA were sharply reduced at the lowest ethanol concentration used, and only modest further reductions in ChAT expression with increasing dose of ethanol exposure (FIG. 16A). In contrast, AChE mRNA levels increased progressively with ethanol dose (FIG. 16B).

Example 22

Figures 17A, 17B, 17C, 17D, 17E, 17F:
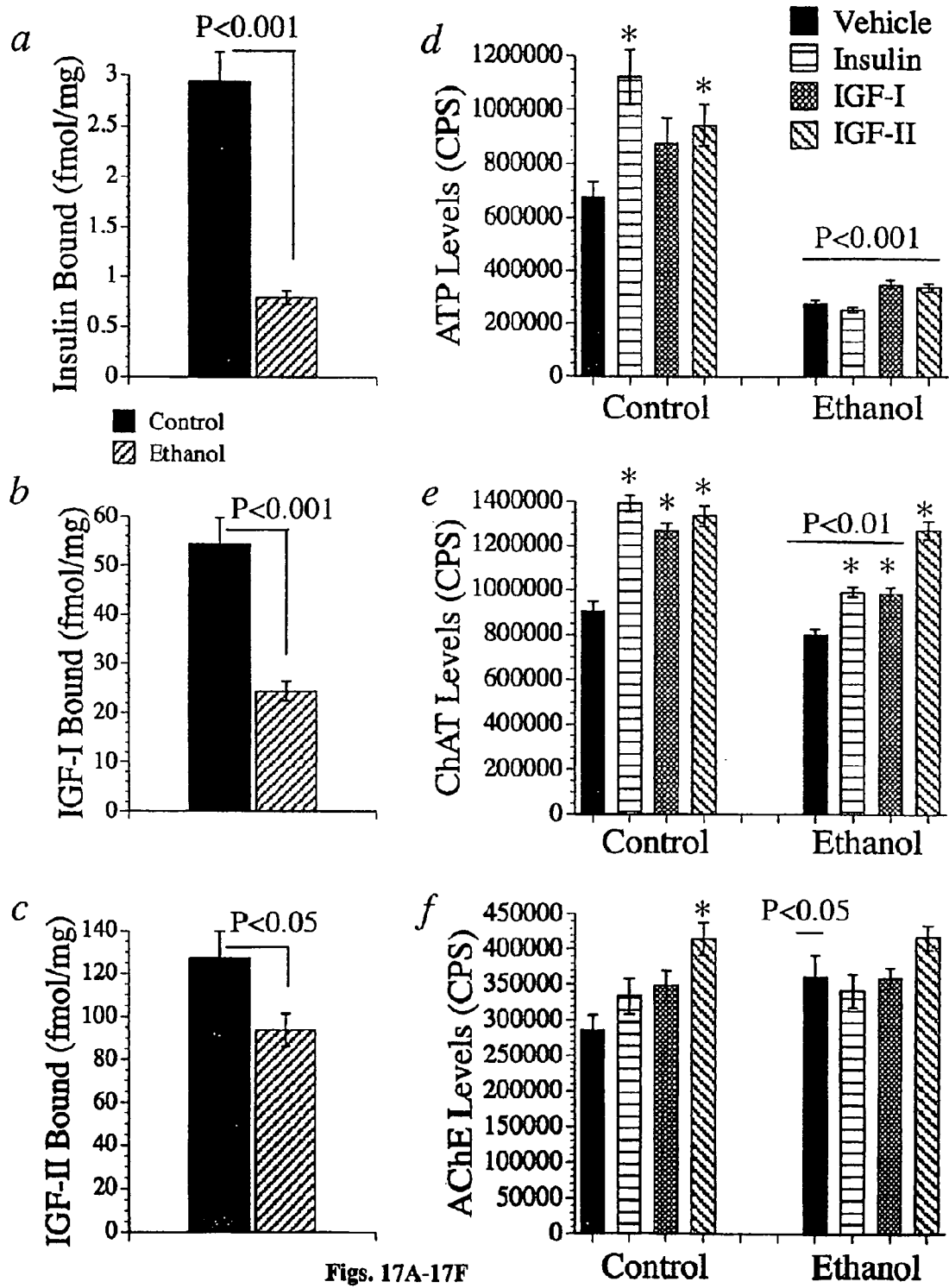

Short-Term In Vitro Ethanol Exposure Impairs Insulin, IGF-I, and IGF-II Receptor Binding, Receptor Tyrosine Kinase Activity, and Corresponding Growth Factor Stimulated ChAT Expression In vitro experiments with primary cerebellar neuron cultures were used to help validate the in vivo observations, and characterize potential mechanisms by which ethanol causes insulin/IGF resistance. Previous studies demonstrated reduced levels of insulin and IGF-I stimulated receptor tyrosine kinase activity in ethanol exposed cerebellar neuron cultures (de la Monte et al., *Cell. Mol. Life Sci.* 62:1131 (2005)). To determine if this effect of ethanol is mediated by impaired ligand-receptor binding, equilibrium binding assays were performed with membrane proteins harvested from primary rat cerebellar control or ethanol exposed (50 mM for 96 hours) neuronal cultures. The concentration of ethanol used was within the range detected in human alcoholics (Fulop et al., *Am. J. Med.* 80:191 (1986); Jagger et al., *Neurosurgery* 15:303 (1984)). ChAT and AChE immunoreactivity were measured directly in the cultured cells using the MICE assay (cellular ELISA), with values normalized to cell density. The results demonstrated significantly reduced levels of insulin (FIG. 17A), IGF-I (FIG. 17B), and IGF-II (FIG. 17C) receptor binding. In addition, the ethanol-treated neuronal cells had significantly reduced basal and insulin, IGF-I, or IGF-II stimulated levels of ATP (FIG. 17D), and basal, insulin-stimulated, and IGF-I stimulated ChAT immunoreactivity relative to the control (FIG. 17E). AChE immunoreactivity was not prominently modulated by growth factor stimulation, although AChE expression was higher in IGF-II-stimulated compared with corresponding un-stimulated control cells, and in un-stimulated ethanol-exposed relative to un-stimulated control cells (FIG. 17F).

Example 23

Figures 18A, 18B, 18C, 18D, 18E, 18F:
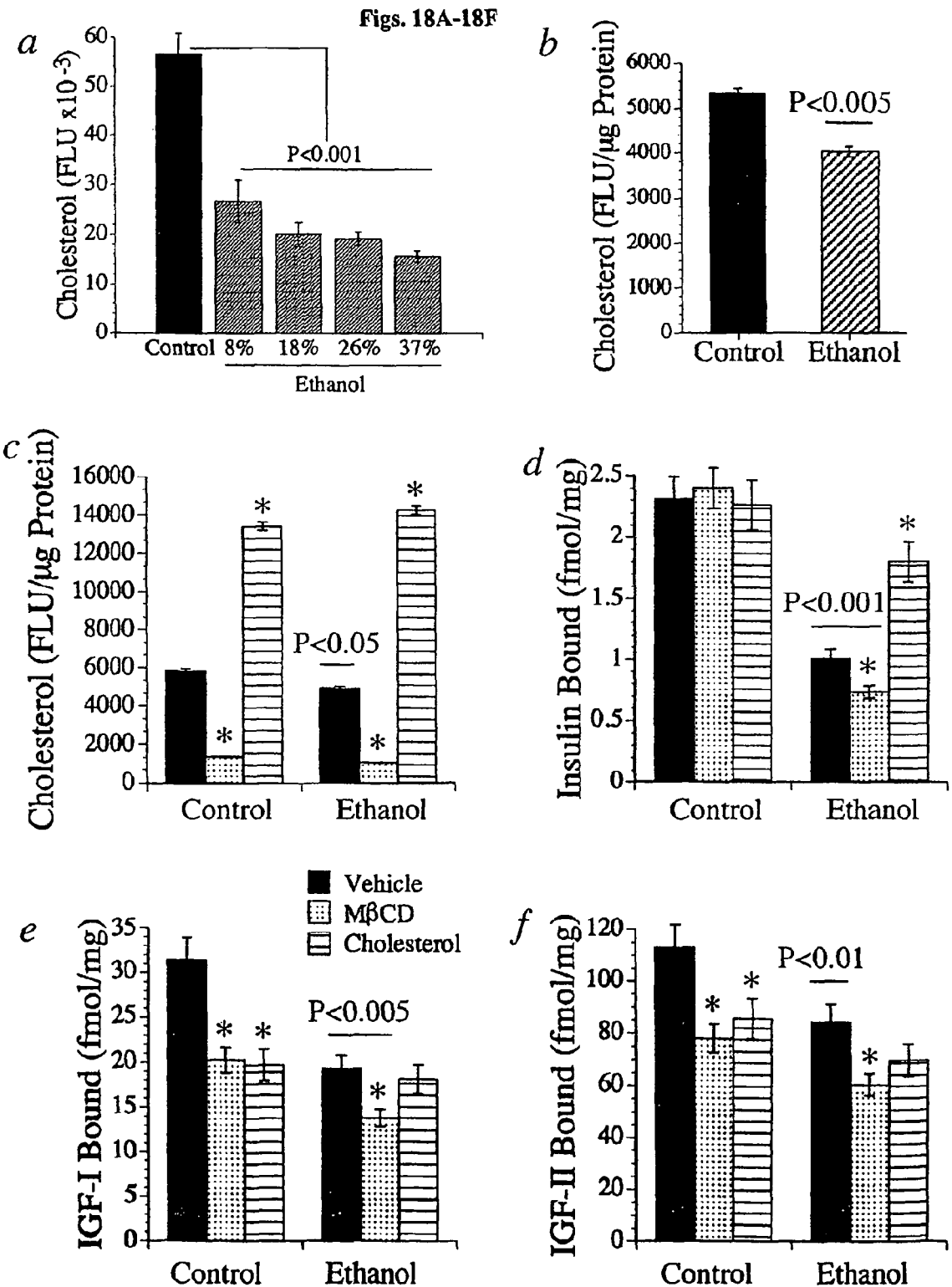

Potential Mechanism of Impaired Insulin and IGF Receptor Binding and Stimulation of ChAT Membrane cholesterol content can influence ligand binding to cell surface receptors. For example, decreased or increased cholesterol content in membranes has been associated with altered or impaired growth factor binding and signal transduction (Cho et al. *Am. J. Physiol. Heart Circ. Physiol.* 286:H1881 (2004); Huo et al., *J. Biol. Chem.* 278:11561 (2003); Meuillet et al., *Biochim. Biophys. Acta* 1454:38 (1999); Peiro et al. *J. Biol. Chem.* 275:37846 (2000)). To determine if the observed differences in receptor binding were correlated with membrane cholesterol content, cholesterol levels were measured in cerebellar membrane extracts. Analysis of the pups' brains (N=8 per group) demonstrated significantly reduced cholesterol content in ethanol-exposed relative to control cerebellar membranes (FIG. 18A). Cerebellar membrane cholesterol content was reduced by ~50% relative to control in the 8% ethanol diet group, but with higher doses of ethanol, only slight further reductions in membrane cholesterol were observed (FIG. 18A). Similarly, in vitro exposure to 50 mM ethanol for 96 hours significantly reduced cerebellar neuron membrane cholesterol content (FIG. 18B).

To further explore the role of cholesterol or lipid depletion as a mediator of impaired binding, control and ethanol-exposed (50 mM for 96 hours) cerebellar neuron cultures were treated for 3 hours with vehicle, 10 mM MβCD, or 10 mM cholesterol in Locke's buffer. The cells were then analyzed for insulin, IGF-I, and IGF-II receptor equilibrium binding. Initial studies demonstrated that treatment with MβCD significantly reduced membrane cholesterol content, whereas treatment with cholesterol significantly increased the membrane cholesterol content in both control and ethanol-exposed cerebellar cultures (FIG. 18C). In control and ethanol-exposed cultures, MβCD treatment significantly inhibited insulin (FIG. 18D), IGF-I (FIG. 18E), and IGF-II (FIG. 18F) receptor binding relative to the corresponding vehicle-treated cells, whereas cholesterol treatment enhanced insulin-receptor binding in the ethanol-treated cells, but had no significant effect on insulin receptor binding in control cells (FIG. 18D). However, cholesterol treatment significantly impaired IGF-I and IGF-II receptor binding in control cerebellar neurons (FIGS. 18E and 18F). In vehicle-treated ethanol-exposed cells, insulin, IGF-I, and IGF-II receptor binding were significantly reduced relative to the vehicle-treated control cells (FIGS. 18D-18F), as illustrated in FIG. 17. In addition, MβCD-treatment of ethanol-exposed cells further reduced insulin receptor binding to levels that were also significantly reduced relative to the MβCD-treated control cell (FIG. 18D). In contrast, MβCD or cholesterol treatment caused similar degrees of impaired IGF-I and IGF-II receptor binding in control and ethanol-exposed neuronal cells (FIGS. 18E and 18F).

Figures 19A, 19B, 19C, 19D, 19E, 19F, 19G, 19H, 19I, 19J, 19K, 19L:
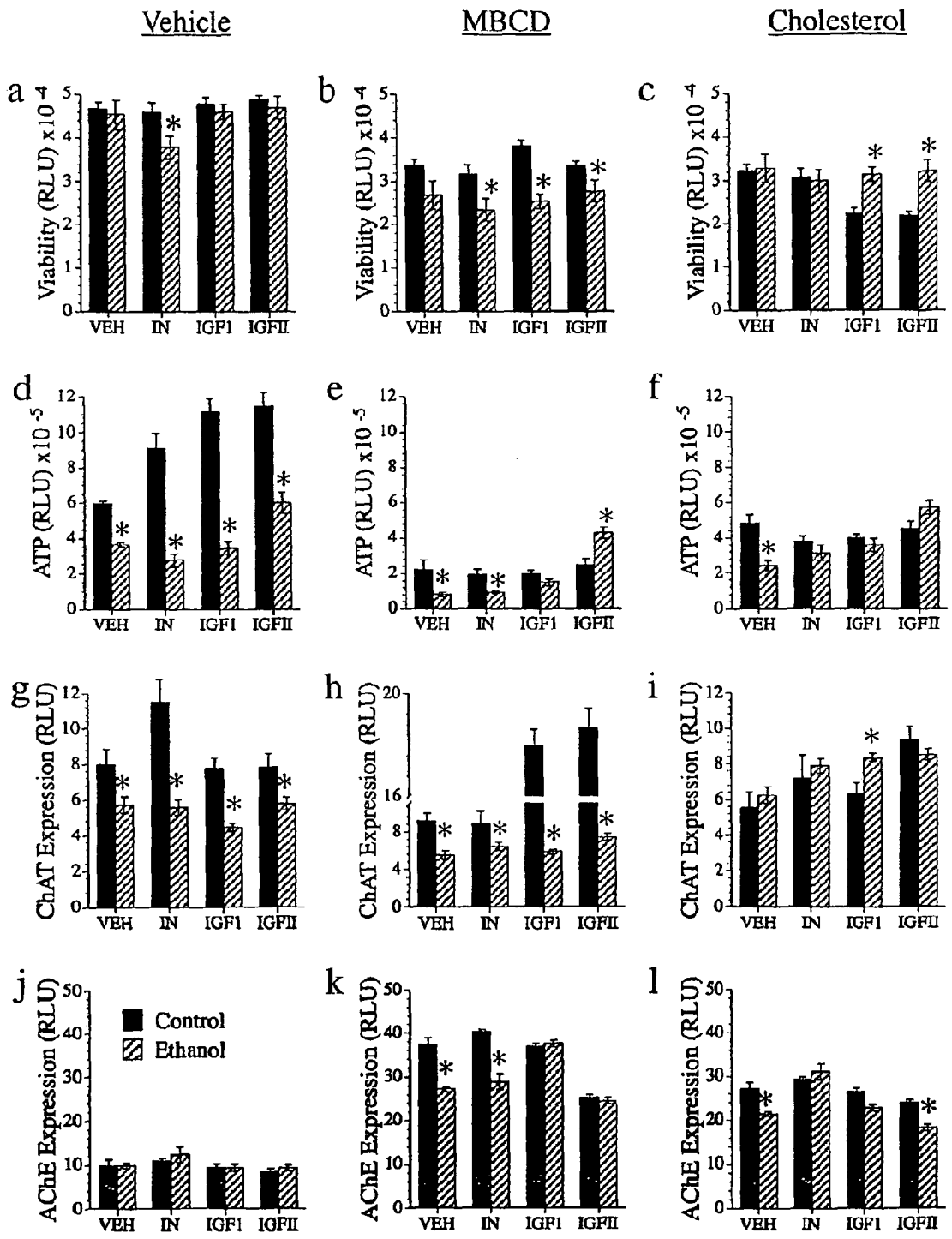

The effects of cholesterol or MβCD treatment on neuronal viability (FIGS. 19A-19C), ATP production (energy metabolism; FIGS. 19D-19F), ChAT (FIGS. 19G-23I) and AChE (FIGS. 19J-19L) immunoreactivity were examined in cells that were treated as described above and stimulated 12 hours with vehicle (control), 10 nM insulin, 10 nM IGF-I, or 25 nM IGF-II in serum-free medium. All assays were performed using 96-well cultures. Viability was measured using the CyQuant assay and ATP content was measured using the ATPLite assay. ChAT and AChE immunoreactivities were measured using the MICE assay (de la Monte et al., *Biotechniques* 26:1073 (1999)) that was modified through the use of luminescence detection reagents (de la Monte et al., *Cell. Mol. Life Sci.* 59:882 (2002); Xu et al., *J. Biol. Chem.* 278: 26929 (2003)). In vehicle-treated cells, neuronal viability was significantly reduced in insulin stimulated, but not in IGF-I or IGF-II stimulated ethanol-exposed cultures (FIG. 19A). However, ATP content was significantly reduced in all ethanol-treated cultures, irrespective of growth factor stimulation (FIG. 19D). MβCD or cholesterol treatment broadly reduced neuronal viability and mitochondrial function in both control and ethanol-exposed cultures, but growth factor stimulated viability and energy metabolism were further reduced in MβCD-treated ethanol-exposed relative to corresponding control cultures (FIGS. 19B, 19C, 19E, 19F). In vehicle-treated control cells, ChAT expression was significantly increased by insulin stimulation, whereas in ethanol-exposed cells, ChAT was not modulated by insulin stimulation, and both basal and growth factor stimulated levels of ChAT were significantly lower than control (FIG. 19G). MβCD-treatment of control cells abolished the insulin-stimulated increases in ChAT, but significantly increased IGF-I- and IGF-II-stimulated ChAT (FIG. 19H). In ethanol-exposed cells, MβCD-treatment was associated with broadly reduced levels of ChAT expression relative to control, independent of growth factor stimulation (FIG. 19). In control cells, cholesterol treatment of control cells muted basal and growth factor stimulated ChAT expression, whereas in the ethanol-exposed cells, cholesterol treatment significantly increased the insulin-, IGF-I-, and IGF-II-stimulated levels of ChAT relative to corresponding vehicle-treated cells, resulting in ChAT expression levels that were similar to or higher than control (FIG. 19). In effect, cholesterol-treatment rescued the ethanol-exposed cells by restoring ChAT expression to control levels in the presence of growth factor stimulation. However, insulin-stimulated ChAT expression in cholesterol-treated, ethanol-exposed cells was still significantly lower than the insulin-stimulated, vehicle-treated control cells (P<0.005), indicating that the cholesterol rescue was only partial. AChE expression was similar in vehicle-treated control and ethanol-exposed neuronal cells, independent of growth factor stimulation (FIG. 19). Treatment with MβCD or cholesterol significantly increased the mean levels of AChE in both control and ethanol-exposed cells, with generally greater effects noted for MβCD than cholesterol (FIG. 19). The only notable inter-group differences were that the AChE levels were significantly lower in ethanol-exposed relative to control MβCD- or cholesterol-treated+un-stimulated, MβCD-treated+insulin-stimulated, and cholesterol-treated+IGF-II-stimulated cultures (FIGS. 19K and 19L).

Since ChAT expression is regulated by insulin and IGF-I stimulation, and acetylcholine is a major neurotransmitter that mediates CNS cognitive and motor functions, it was of interest to determine if the inhibitory effects of ethanol on insulin and IGF-I signaling in the brain impaired acetylcholine homeostasis. The real time quantitative RT-PCR studies demonstrated reduced levels of ChAT and increased levels of AChE gene expression in ethanol-exposed cerebella. In addition, in vitro studies demonstrated that basal, insulin-stimulated, and IGF-I stimulated levels of ChAT immunoreactivity were significantly reduced in cerebellar neuron cultures after 4 days of ethanol exposure, at a time when the cultures were post-mitotic and significant cell loss was not detected. Potential mechanisms by which ethanol exposure leads to reduced ChAT expression include, inhibition of insulin/IGF-I signaling and, with chronic in vivo exposure, impaired survival of ChAT-expressing neurons. The increased AChE expression observed after chronic in utero exposure to ethanol could be explained on the basis astrocytic and microglial cell proliferation and/or activation following death of neurons and oligodendroglia.

Cerebella from rat pups that were chronically exposed to ethanol in utero were found to have significantly reduced levels of membrane cholesterol relative to control cerebella. In addition, membrane cholesterol content was significantly reduced in cerebellar neuron cultures that were subjected to short-term ethanol exposure, indicating that even short-term ethanol exposure can alter the lipid composition of brain cell membranes. In vitro experiments demonstrated that MβCD depletion of membrane cholesterol, significantly inhibited IGF-I and IGF-II binding in control cells and insulin, IGF-I and IGF-II binding in ethanol-exposed cells. Cholesterol treatment, which resulted in increased cholesterol content in cerebellar neuron membranes, also inhibited IGF-I and IGF-II receptor binding in control and ethanol-exposed cells. These findings are consistent with the concept that cholesterol influences ligand-receptor interactions by altering the membrane fluidity or the inter-molecular interactions (Gimpl et al. *Biochemistry* 36:10959 (1997)). However, cholesterol treatment did not impair insulin receptor binding in control cells, and it significantly increased insulin receptor binding in ethanol-exposed cells. The fact that the rescue was incomplete suggests that other lipids depleted by ethanol exposure are also important for mediating insulin receptor binding. These results are consistent with a previous report demonstrating that cholesterol and lipid content and composition in membranes can significantly influence ligand binding to cell surface receptors and attendant downstream intracellular signaling (Meuillet et al., *Biochim. Biophys. Acta* 1454:38 (1999)). The relative preservation of insulin receptor binding in MβCD-treated control cells, and incomplete rescue of insulin receptor binding produced by cholesterol treatment of ethanol-exposed cells suggest that other lipids present in caveolae that are not depleted by MβCD but are reduced by ethanol treatment, may be critical mediators of insulin receptor binding.

Previous studies demonstrated that MβCD treatment, which depletes membrane cholesterol, causes insulin resistance (Le Lay et al., *J. Biol. Chem.* 276:16904 (2001); Parpal et al., *J. Biol. Chem.* 276:9670 (2001)), and that cholesterol addition, which effectively alters membrane lipid composition in otherwise normal cells, also decreases insulin responsiveness (Meuillet et al. *Biochim. Biophys. Acta* 1454:38 (1999)). In neuronal cells, tyrosine kinase receptors are distributed in the low-density membrane fraction corresponding to caveolae (Wu et al. *J. Biol. Chem.* 272:3554 (1997)), and in general, insulin receptors signal within caveolae microdomains. Experimentally, MβCD chelation of cholesterol and attendant disruption of caveolae inhibits insulin receptor tyrosine kinase auto-activation, and insulin stimulated glucose uptake (Gustavsson et al. *FASEB J.* 13:1961 (1999); Cohen et al., *Am. J. Physiol. Endocrinol. Metab.* 285:E1151 (2003)). Further investigations localized a portion of the IRS-1 molecule to caveolae and showed that treatment with relatively low concentrations of MβCD (2 mM), which does not inhibit insulin receptor auto-phosphorylation or IRS-1 tyrosine phosphorylation, disrupts caveolae/lipid rafts and the downstream insulin and IRS-1 signaling mechanisms (Balbis et al., *J. Biol. Chem.* 279:39348 (2004); Karlsson et al., *Eur. J. Biochem.* 271:2471 (2004)), with reduced activation of the IRS-1-PI3 kinase-Akt pathway (McGuire et al.,

*Biochem. Biophys. Res. Commun.* 204:399 (1994)), and in some instances, preservation of MAPK signaling (Parpal et al., *J. Biol. Chem.* 276:9670 (2001)). Therefore, apart from its inhibitory effects on receptor binding, cholesterol depletion may impair insulin signaling downstream of its receptor through PI3 kinase due to disruption of caveolae microdomains.

In previous studies, the inventors demonstrated that ethanol exposure also selectively impairs insulin and IGF-I stimulated PI3 kinase-Akt in immature neurons and the developing brain, suggesting that some of the adverse effects of ethanol on survival signaling and mitochondrial function are mediated through pathological alterations in the cholesterol and lipid composition of caveolae and lipid rafts. However, it is noteworthy that the properties of insulin signaling in relation to its dependence on caveolar integrity can vary with tissue and cell type. For example, in the liver, caveolar gene depletion does not inhibit insulin receptor activation and signaling because ligand-bound receptors can be recruited to lipid rafts to mediate signaling (Vainio et al., *EMBO Rep.* 3:95 (2002). Although IGF-I signaling through IRS-1-Akt is also impaired by cholesterol depletion (Podar et al. *J. Biol. Chem.* 278:5794 (2003)), IGF-I signaling was localized to lipid rafts and determined to be caveolae-independent (Hong et al., *Cell Death Differ.* 11:714 (2004)). The distinct subcellular localizations of insulin and IGF-I signaling in caveolae versus lipid rafts could partially account for the differential effects of insulin and IGF-I stimulation, despite highly overlapping downstream pathways.

The finding that ChAT expression was markedly increased in MβCD-treated IGF-I or IGF-II stimulated control cells, despite significantly reduced binding relative to corresponding vehicle-treated cells provides further evidence that insulin and IGF stimulated functions are not strictly related to binding. Similarly, in ethanol-exposed cells, cholesterol treatment significantly enhanced only insulin receptor binding, yet insulin, IGF-I, and IGF-II stimulated ChAT were all significantly increased relative to corresponding vehicle-treated cells. Therefore, insulin and IGF stimulated ChAT expression are prominently regulated by membrane cholesterol content and lipid composition. In control cells, reducing cholesterol content dramatically increased IGF-I and IGF-II stimulated ChAT, whereas increased cholesterol blunted the insulin-stimulated increase in ChAT. This suggests that in control cells, reduced cholesterol relative to other membrane lipids may enhance acetylcholine biosynthesis through lipid raft but not caveolar-dependent (insulin) signaling mechanisms. In contrast, cholesterol treatment rescued ethanol-exposed neuronal cells by enhancing insulin, IGF-I and IGF-II stimulated ChAT expression. Therefore, membrane lipid and cholesterol content have critical roles in modulating neuronal responses to insulin and IGF stimulated ChAT expression and acetylcholine biosynthesis. The finding of broadly increased levels of AChE expression in MβCD or cholesterol treated control and ethanol-exposed cells was unexpected. However, one potential explanation for this result is that substantial increases or decreases in membrane lipid composition may impair growth factor stimulated energy metabolism. This interpretation is consistent with our finding that either MβCD or cholesterol treatment reduced energy metabolism and viability in neuronal cells, independent of growth factor stimulation (FIG. 19). Impaired energy metabolism could cause oxidative stress, and recent studies demonstrated that oxidative stress increases acetylcholinesterase function (Kaizer et al., *J. Inorg. Biochem.* 99:1865 (2005); Melo et al. *J. Neurosci. Res.* 45:117 (2003)). The results linking ethanol impaired insulin and IGF-I signaling to reduced levels of ChAT and increased levels of AChE, i.e., perturbations in acetylcholine homeostasis, as well as mediators of neuro-inflammation and oxidative stress (impaired energy metabolism, increased microglia and astrocytes) in the brain, suggest important and novel mechanisms by which chronic gestational exposure to ethanol leads to developmental deficits in CNS cognitive and motor functions.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

What is claimed is:

1. A method for treating alcohol-induced cognitive impairment or an alcohol-induced brain disease in an animal, comprising administering to said animal an amount of peroxisome proliferator activated receptor-δ (PPAR-δ) agonist effective to decrease insulin resistance in the brain of said animal, wherein the agonist is:

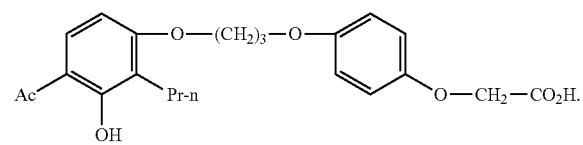

2. The method of claim 1, wherein said brain disease is associated with oxidative stress.

3. The method of claim 1, wherein said brain disease is associated with lipid peroxidation.

4. The method of claim 1, wherein said brain disease is associated with DNA damage.

5. The method of claim 1, wherein said brain disease is produced in the brain of a fetal animal by chronic alcohol intake by the parent.

6. The method of claim 5, wherein said chronic alcohol intake is at least about 0.1 g pure alcohol/kg/day on average.

7. The method of claim 5, wherein said chronic alcohol intake is at least about 0.5 g pure alcohol/kg/day on average.

8. The method of claim 5, wherein said chronic alcohol intake is at least about 1 g pure alcohol/kg/day on average.

* * * * *

SEQUENCE LISTING

```
<160> NUMBER OF SEQ ID NOS: 52

<210> SEQ ID NO 1
<211> LENGTH: 20
<212> TYPE: DNA
<213> ORGANISM: Artificial Sequence
<220> FEATURE:
<223> OTHER INFORMATION: Synthetic rat 18S rRNA primer

<400> SEQUENCE: 1
ggacacggac aggattgaca                                                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic rat 18S rRNA primer

<400> SEQUENCE: 2
acccacggaa tcgagaaaga                                                    20
```

```
<210> SEQ ID NO 3
<211> LENGTH: 23
<212> TYPE: DNA
<213> ORGANISM: Artificial Sequence
<220> FEATURE:
<223> OTHER INFORMATION: Synthetic rat 28S rRNA primer

<400> SEQUENCE: 3
ggtaaacggc gggagtaact atg                                              23

<210> SEQ ID NO 4
<211> LENGTH: 24
<212> TYPE: DNA
<213> ORGANISM: Artificial Sequence
<220> FEATURE:
<223> OTHER INFORMATION: Synthetic rat 28S rRNA primer

<400> SEQUENCE: 4
taggtaggga cagtgggaat ctcg                                             24

<210> SEQ ID NO 5
<211> LENGTH: 22
<212> TYPE: DNA
<213> ORGANISM: Artificial Sequence
<220> FEATURE:
<223> OTHER INFORMATION: Synthetic rat insulin primer

<400> SEQUENCE: 5
ttctacacac ccaagtcccg tc                                               22

<210> SEQ ID NO 6
<211> LENGTH: 22
<212> TYPE: DNA
<213> ORGANISM: Artificial Sequence
<220> FEATURE:
<223> OTHER INFORMATION: Synthetic rat insulin primer

<400> SEQUENCE: 6
atccacaatg ccacgcttct gc                                               22

<210> SEQ ID NO 7
<211> LENGTH: 22
<212> TYPE: DNA
<213> ORGANISM: Artificial Sequence
<220> FEATURE:
<223> OTHER INFORMATION: Synthetic rat insulin receptor primer

<400> SEQUENCE: 7
tgacaatgag gaatgtgggg ac                                               22

<210> SEQ ID NO 8
<211> LENGTH: 24
<212> TYPE: DNA
<213> ORGANISM: Artificial Sequence
<220> FEATURE:
<223> OTHER INFORMATION: Synthetic rat insulin receptor primer

<400> SEQUENCE: 8
gggcaaactt tctgacaatg actg                                             24

<210> SEQ ID NO 9
<211> LENGTH: 23
<212> TYPE: DNA
<213> ORGANISM: Artificial Sequence
<220> FEATURE:
<223> OTHER INFORMATION: Synthetic rat IGF-I primer
```

```
<400> SEQUENCE: 9
gaccaagggg cttttacttc aac                                    23

<210> SEQ ID NO 10
<211> LENGTH: 22
<212> TYPE: DNA
<213> ORGANISM: Artificial Sequence
<220> FEATURE:
<223> OTHER INFORMATION: Synthetic rat IGF-I primer

<400> SEQUENCE: 10
tttgtaggct tcagcggagc ac                                     22

<210> SEQ ID NO 11
<211> LENGTH: 23
<212> TYPE: DNA
<213> ORGANISM: Artificial Sequence
<220> FEATURE:
<223> OTHER INFORMATION: Synthetic rat IGF-I receptor primer

<400> SEQUENCE: 11
gaagtctgcg gtggtgataa agg                                    23

<210> SEQ ID NO 12
<211> LENGTH: 22
<212> TYPE: DNA
<213> ORGANISM: Artificial Sequence
<220> FEATURE:
<223> OTHER INFORMATION: Synthetic rat IGF-I receptor primer

<400> SEQUENCE: 12
tctgggcaca aagatggagt tg                                     22

<210> SEQ ID NO 13
<211> LENGTH: 22
<212> TYPE: DNA
<213> ORGANISM: Artificial Sequence
<220> FEATURE:
<223> OTHER INFORMATION: Synthetic rat IGF-II primer

<400> SEQUENCE: 13
ccaagaagaa aggaagggga cc                                     22

<210> SEQ ID NO 14
<211> LENGTH: 22
<212> TYPE: DNA
<213> ORGANISM: Artificial Sequence
<220> FEATURE:
<223> OTHER INFORMATION: Synthetic rat IGF-II primer

<400> SEQUENCE: 14
ggcggctatt gttgttcaca gc                                     22

<210> SEQ ID NO 15
<211> LENGTH: 24
<212> TYPE: DNA
<213> ORGANISM: Artificial Sequence
<220> FEATURE:
<223> OTHER INFORMATION: Synthetic rat IGF-II receptor primer

<400> SEQUENCE: 15
ttgctattga ccttagtccc ttgg                                   24
```

```
<210> SEQ ID NO 16
<211> LENGTH: 24
<212> TYPE: DNA
<213> ORGANISM: Artificial Sequence
<220> FEATURE:
<223> OTHER INFORMATION: Synthetic rat IGF-II receptor primer

<400> SEQUENCE: 16
agagtgagac ctttgtgtcc ccac                                              24

<210> SEQ ID NO 17
<211> LENGTH: 22
<212> TYPE: DNA
<213> ORGANISM: Artificial Sequence
<220> FEATURE:
<223> OTHER INFORMATION: Synthetic rat AchE primer

<400> SEQUENCE: 17
ttctcccaca cctgtcctca tc                                                22

<210> SEQ ID NO 18
<211> LENGTH: 24
<212> TYPE: DNA
<213> ORGANISM: Artificial Sequence
<220> FEATURE:
<223> OTHER INFORMATION: Synthetic rat AchE primer

<400> SEQUENCE: 18
ttcatagata ccaacacggt tccc                                              24

<210> SEQ ID NO 19
<211> LENGTH: 24
<212> TYPE: DNA
<213> ORGANISM: Artificial Sequence
<220> FEATURE:
<223> OTHER INFORMATION: Synthetic rat ChAT primer

<400> SEQUENCE: 19
tcacagatgc gtttcacaac tacc                                              24

<210> SEQ ID NO 20
<211> LENGTH: 21
<212> TYPE: DNA
<213> ORGANISM: Artificial Sequence
<220> FEATURE:
<223> OTHER INFORMATION: Synthetic rat ChAT primer

<400> SEQUENCE: 20
tgggacacaa cagcaacctt g                                                 21

<210> SEQ ID NO 21
<211> LENGTH: 24
<212> TYPE: DNA
<213> ORGANISM: Artificial Sequence
<220> FEATURE:
<223> OTHER INFORMATION: Synthetic rat Hu primer

<400> SEQUENCE: 21
cactgtgtga gggtccatct tctg                                              24

<210> SEQ ID NO 22
<211> LENGTH: 22
<212> TYPE: DNA
<213> ORGANISM: Artificial Sequence
<220> FEATURE:
<223> OTHER INFORMATION: Synthetic rat Hu primer
```

<400> SEQUENCE: 22
tcaagccatt ccactccatc tg                                              22

<210> SEQ ID NO 23
<211> LENGTH: 22
<212> TYPE: DNA
<213> ORGANISM: Artificial Sequence
<220> FEATURE:
<223> OTHER INFORMATION: Synthetic rat GFAP primer

<400> SEQUENCE: 23
tggtaaagac ggtggagatg cg                                              22

<210> SEQ ID NO 24
<211> LENGTH: 23
<212> TYPE: DNA
<213> ORGANISM: Artificial Sequence
<220> FEATURE:
<223> OTHER INFORMATION: Synthetic rat GFAP primer

<400> SEQUENCE: 24
ggcactaaaa cagaagcaag ggg                                             23

<210> SEQ ID NO 25
<211> LENGTH: 24
<212> TYPE: DNA
<213> ORGANISM: Artificial Sequence
<220> FEATURE:
<223> OTHER INFORMATION: Synthetic rat MAG-1 primer

<400> SEQUENCE: 25
aaccttctgt atcagtgctc ctcg                                            24

<210> SEQ ID NO 26
<211> LENGTH: 23
<212> TYPE: DNA
<213> ORGANISM: Artificial Sequence
<220> FEATURE:
<223> OTHER INFORMATION: Synthetic rat MAG-1 primer

<400> SEQUENCE: 26
cagtcaacca agtctcttcc gtg                                             23

<210> SEQ ID NO 27
<211> LENGTH: 24
<212> TYPE: DNA
<213> ORGANISM: Artificial Sequence
<220> FEATURE:
<223> OTHER INFORMATION: Synthetic rat ET-1 primer

<400> SEQUENCE: 27
ttccaagaga ggttgaggtg ttcc                                            24

<210> SEQ ID NO 28
<211> LENGTH: 25
<212> TYPE: DNA
<213> ORGANISM: Artificial Sequence
<220> FEATURE:
<223> OTHER INFORMATION: Synthetic rat ET-1 primer

<400> SEQUENCE: 28
cagcaagaag aggcaagaga atcac                                           25

<210> SEQ ID NO 29
<211> LENGTH: 20
<212> TYPE: DNA
<213> ORGANISM: Artificial Sequence
<220> FEATURE:
<223> OTHER INFORMATION: Synthetic rat AIF-1 primer

<400> SEQUENCE: 29
ggatgggatc aacaagcact                                                    20

<210> SEQ ID NO 30
<211> LENGTH: 20
<212> TYPE: DNA
<213> ORGANISM: Artificial Sequence
<220> FEATURE:
<223> OTHER INFORMATION: Synthetic rat AIF-1 primer

<400> SEQUENCE: 30
gtttctccag cattcgcttc                                                    20

<210> SEQ ID NO 31
<211> LENGTH: 22
<212> TYPE: DNA
<213> ORGANISM: Artificial Sequence
<220> FEATURE:
<223> OTHER INFORMATION: Synthetic human insulin primer

<400> SEQUENCE: 31
ttctacacac ccaagtcccg tc                                                 22

<210> SEQ ID NO 32
<211> LENGTH: 22
<212> TYPE: DNA
<213> ORGANISM: Artificial Sequence
<220> FEATURE:
<223> OTHER INFORMATION: Synthetic human insulin primer

<400> SEQUENCE: 32
atccacaatg ccacgcttct gc                                                 22

<210> SEQ ID NO 33
<211> LENGTH: 25
<212> TYPE: DNA
<213> ORGANISM: Artificial Sequence
<220> FEATURE:
<223> OTHER INFORMATION: Synthetic human insulin receptor primer

<400> SEQUENCE: 33
ggtagaaacc attactggct tcctc                                              25

<210> SEQ ID NO 34
<211> LENGTH: 25
<212> TYPE: DNA
<213> ORGANISM: Artificial Sequence
<220> FEATURE:
<223> OTHER INFORMATION: Synthetic human insulin receptor primer

<400> SEQUENCE: 34
cgtagagagt gtagttccca tccac                                              25

<210> SEQ ID NO 35
<211> LENGTH: 24
<212> TYPE: DNA
<213> ORGANISM: Artificial Sequence
<220> FEATURE:
<223> OTHER INFORMATION: Synthetic human IGF-I primer

<400> SEQUENCE: 35
cacttctttc tacacaactc gggc                                              24

<210> SEQ ID NO 36
<211> LENGTH: 21
<212> TYPE: DNA
<213> ORGANISM: Artificial Sequence
<220> FEATURE:
<223> OTHER INFORMATION: Synthetic human IGF-I primer

<400> SEQUENCE: 36
cgacttgctg ctgcttttga g                                                 21

<210> SEQ ID NO 37
<211> LENGTH: 25
<212> TYPE: DNA
<213> ORGANISM: Artificial Sequence
<220> FEATURE:
<223> OTHER INFORMATION: Synthetic human IGF-I receptor primer

<400> SEQUENCE: 37
agggcgtagt tgtagaagag tttcc                                             25

<210> SEQ ID NO 38
<211> LENGTH: 22
<212> TYPE: DNA
<213> ORGANISM: Artificial Sequence
<220> FEATURE:
<223> OTHER INFORMATION: Synthetic human IGF-I receptor primer

<400> SEQUENCE: 38
tacttgctgc tgttccgagt gg                                                22

<210> SEQ ID NO 39
<211> LENGTH: 22
<212> TYPE: DNA
<213> ORGANISM: Artificial Sequence
<220> FEATURE:
<223> OTHER INFORMATION: Synthetic human IGF-II primer

<400> SEQUENCE: 39
ctgattgctc tacccaccca ag                                                22

<210> SEQ ID NO 40
<211> LENGTH: 22
<212> TYPE: DNA
<213> ORGANISM: Artificial Sequence
<220> FEATURE:
<223> OTHER INFORMATION: Synthetic human IGF-II primer

<400> SEQUENCE: 40
ttgctcactt ccgattgctg gc                                                22

<210> SEQ ID NO 41
<211> LENGTH: 25
<212> TYPE: DNA
<213> ORGANISM: Artificial Sequence
<220> FEATURE:
<223> OTHER INFORMATION: Synthetic human IGF-II receptor primer

<400> SEQUENCE: 41
cacgacttga agacacgcac ttatc                                             25

```
<210> SEQ ID NO 42
<211> LENGTH: 23
<212> TYPE: DNA
<213> ORGANISM: Artificial Sequence
<220> FEATURE:
<223> OTHER INFORMATION: Synthetic human IGF-II receptor primer

<400> SEQUENCE: 42
gctgctctgg actctgtgat ttg                                              23

<210> SEQ ID NO 43
<211> LENGTH: 20
<212> TYPE: DNA
<213> ORGANISM: Artificial Sequence
<220> FEATURE:
<223> OTHER INFORMATION: Synthetic human IRS-1 primer

<400> SEQUENCE: 43
tgctgggggt ttggagaatg                                                  20

<210> SEQ ID NO 44
<211> LENGTH: 23
<212> TYPE: DNA
<213> ORGANISM: Artificial Sequence
<220> FEATURE:
<223> OTHER INFORMATION: Synthetic human IRS-1 primer

<400> SEQUENCE: 44
ggcactgttt gaagtccttg acc                                              23

<210> SEQ ID NO 45
<211> LENGTH: 19
<212> TYPE: DNA
<213> ORGANISM: Artificial Sequence
<220> FEATURE:
<223> OTHER INFORMATION: Synthetic human IRS-2 primer

<400> SEQUENCE: 45
aaaattggcg gagcaaggc                                                   19

<210> SEQ ID NO 46
<211> LENGTH: 22
<212> TYPE: DNA
<213> ORGANISM: Artificial Sequence
<220> FEATURE:
<223> OTHER INFORMATION: Synthetic human IRS-2 primer

<400> SEQUENCE: 46
atgttcaggc agcagtcgag ag                                               22

<210> SEQ ID NO 47
<211> LENGTH: 22
<212> TYPE: DNA
<213> ORGANISM: Artificial Sequence
<220> FEATURE:
<223> OTHER INFORMATION: Synthetic human IRS-4 primer

<400> SEQUENCE: 47
ccgacacctc attgctcttt tc                                               22

<210> SEQ ID NO 48
<211> LENGTH: 22
<212> TYPE: DNA
<213> ORGANISM: Artificial Sequence
<220> FEATURE:
<223> OTHER INFORMATION: Synthetic human IRS-4 primer
```

```
<400> SEQUENCE: 48
tttcctgctc cgactcgttc tc                                              22

<210> SEQ ID NO 49
<211> LENGTH: 20
<212> TYPE: DNA
<213> ORGANISM: Artificial Sequence
<220> FEATURE:
<223> OTHER INFORMATION: Synthetic human 18S primer

<400> SEQUENCE: 49
ggacacggac aggattgaca                                                 20

<210> SEQ ID NO 50
<211> LENGTH: 20
<212> TYPE: DNA
<213> ORGANISM: Artificial Sequence
<220> FEATURE:
<223> OTHER INFORMATION: Synthetic human 18S primer

<400> SEQUENCE: 50
acccacggaa tcgagaaaga                                                 20

<210> SEQ ID NO 51
<211> LENGTH: 23
<212> TYPE: DNA
<213> ORGANISM: Artificial Sequence
<220> FEATURE:
<223> OTHER INFORMATION: Synthetic human 28S primer

<400> SEQUENCE: 51
ggtaaacggc gggagtaact atg                                             23

<210> SEQ ID NO 52
<211> LENGTH: 24
<212> TYPE: DNA
<213> ORGANISM: Artificial Sequence
<220> FEATURE:
<223> OTHER INFORMATION: Synthetic human 28S primer

<400> SEQUENCE: 52
taggtaggga cagtgggaat ctcg                                            24
```